(12) United States Patent
Bhedi et al.

(10) Patent No.: US 8,981,131 B2
(45) Date of Patent: Mar. 17, 2015

(54) TRICYCLIC COMPOUNDS FOR THE TREATMENT OF INFLAMMATORY DISORDERS

(75) Inventors: Dilip Narayanrao Bhedi, Mumbai (IN); Ram Asrey Vishwakarma, Jammu & Kashmir (IN); Vaishali Deka, Mumbai (IN); Dattatray Maruti More, Dist-Pune (IN); Manivannan Ramalingam, Tamilnadu (IN); Ashish Suthar, Mumbai (IN); Roda Dalal, Mumbai (IN); Sapna Parikh, Mumbai (IN); Aditi Amol Tannu, Mumbai (IN)

(73) Assignee: Piramal Enterprises Limited, Mumbai (IN)

( * ) Notice: Subject to any disclaimer, the term of this patent is extended or adjusted under 35 U.S.C. 154(b) by 688 days.

(21) Appl. No.: 12/670,701

(22) PCT Filed: Jul. 25, 2008

(86) PCT No.: PCT/IB2008/052990
§ 371 (c)(1),
(2), (4) Date: Jan. 26, 2010

(87) PCT Pub. No.: WO2009/016565
PCT Pub. Date: Feb. 5, 2009

(65) Prior Publication Data
US 2011/0009396 A1    Jan. 13, 2011

Related U.S. Application Data
(60) Provisional application No. 60/952,359, filed on Jul. 27, 2007.

(51) Int. Cl.

| | | |
|---|---|---|
| A61K 31/541 | (2006.01) |
| C07D 307/92 | (2006.01) |
| C07D 405/06 | (2006.01) |
| C07D 413/06 | (2006.01) |
| C07D 417/06 | (2006.01) |
| A61K 31/343 | (2006.01) |
| A61K 31/496 | (2006.01) |
| A61K 31/4525 | (2006.01) |
| A61K 31/4155 | (2006.01) |
| A61K 31/4178 | (2006.01) |
| A61K 31/4196 | (2006.01) |
| A61K 31/4025 | (2006.01) |
| A61K 31/5377 | (2006.01) |
| A61P 19/02 | (2006.01) |
| A61P 29/00 | (2006.01) |
| A61P 19/10 | (2006.01) |
| A61P 9/00 | (2006.01) |
| A61P 17/06 | (2006.01) |
| A61P 37/04 | (2006.01) |
| A61P 37/06 | (2006.01) |
| A61P 37/02 | (2006.01) |
| A61P 25/28 | (2006.01) |
| A61P 31/18 | (2006.01) |
| A61P 11/00 | (2006.01) |
| A61P 31/14 | (2006.01) |
| A61P 3/10 | (2006.01) |
| A61P 11/06 | (2006.01) |
| A61P 35/00 | (2006.01) |
| C07D 405/12 | (2006.01) |
| C07H 17/04 | (2006.01) |

(52) U.S. Cl.
CPC ........... *C07D 307/92* (2013.01); *C07D 405/06* (2013.01); *C07D 405/12* (2013.01); *C07D 417/06* (2013.01); *C07H 17/04* (2013.01)
USPC .......... 549/458; 544/375; 544/153; 544/58.7; 546/196; 548/364.4; 548/311.4; 548/266.4; 548/525; 514/228.2; 514/468; 514/254.11; 514/320; 514/406; 514/397; 514/383; 514/422; 514/232.8

(58) Field of Classification Search
None
See application file for complete search history.

(56) References Cited

FOREIGN PATENT DOCUMENTS

IN    WO2006/134609    * 12/2006    ........... A61K 31/541

OTHER PUBLICATIONS

Shekhani et al. in Journal of Natural Products 54(3) 882-885 (1991).*
(Continued)

*Primary Examiner* — Dennis Heyer
(74) *Attorney, Agent, or Firm* — Ladas & Parry LLP

(57) ABSTRACT

The present invention provides compounds represented by formula I:

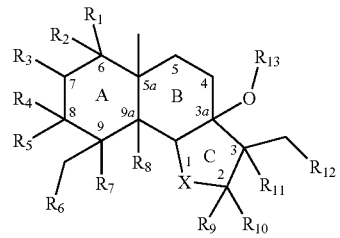

Formula 1 wherein, $R_1$, $R_2$, $R_3$, $R_4$, $R_5$, $R_6$, $R_7$, $R_8$, $R_9$, $R_{10}$, $R_{11}$, $R_{12}$, $R_{13}$ and X are as defined in the specification, in all its stereoisomeric and tautomeric forms and mixtures thereof in all ratios, and its pharmaceutically acceptable salts, pharmaceutically acceptable solvates, pharmaceutically acceptable polymorphs and prodrugs. These compounds are useful for treatment of inflammatory disorders including those caused by elevated levels of proinflammatory cytokines such as Tumor Necrosis Factor (TNF-α and/or interleukins (IL-1β, IL-6, IL-8). The invention also relates to processes for the manufacture of compounds of formula 1 and pharmaceutical compositions containing them.

29 Claims, No Drawings

(56) References Cited

OTHER PUBLICATIONS

Shekhani et al. in Phytochemistry 29(8), 2573-2576 (1990).*
Morissette et al. in Advanced Drug Delivery Reviews 56 (2004) 275-300.*

Vippagunta et al., Crystalline solids, Advanced Drug Delivery Reviews, 48 (2001) 3-26.*
Sohoni et al. in Journal of the Chemical Society, Perkin Transactions Organic and Bio-Organic Chemistry (1972-199) (2), 157-60 (1988) (CA STN Record, Accession No. 1988:164697).*

* cited by examiner

TRICYCLIC COMPOUNDS FOR THE TREATMENT OF INFLAMMATORY DISORDERS

This application is a 371 of International Application PCT/IB2008/052990, filed Jul. 25, 2008, which claims the benefit of U.S. Provisional Patent Application 60/952,359, filed Jul. 27, 2007.

FIELD OF INVENTION

The present invention relates to tricyclic compounds, to processes for their preparation, pharmaceutical compositions containing them, and their use in the treatment of inflammatory disorders, such as those caused by elevated levels of proinflammatory cytokines such as Tumor Necrosis Factor-alpha (TNF-α) and/or interleukins such as IL-1β, IL-6, and IL-8.

BACKGROUND OF INVENTION

Inflammation is the response of a tissue to injury that may be caused by a biological assault such as invading organisms and parasites, ischemia, antigen-antibody reactions or other forms of physical or chemical injury. It is characterized by increased blood flow to the tissue, causing pyrexia, erythema, induration and pain.

Several proinflammatory cytokines, especially TNF-α (tumor necrosis factor-α) and interleukins (IL-1 β, IL-6, IL-8) play an important role in the inflammatory process. Both IL-1 and TNF-α are derived from mononuclear cells and macrophages and in turn induce the expression of a variety of genes that contribute to the inflammatory process. An increase in TNF-α synthesis/release is a common phenomenon during the inflammatory process. Inflammation is an inherent part of various disease states like rheumatoid arthritis, Crohn's disease, septic shock syndrome, atherosclerosis, among other clinical conditions. Tumor Necrosis Factor-α (TNF-α), a pleiotropic cytokine, is produced mainly by macrophages, but other types of cells also produce it. TNF-α demonstrates beneficial as well as pathological activities. It has both growth stimulating effects and growth inhibitory properties, besides being self-regulatory. The beneficial functions of TNF-α include maintaining homeostasis by regulating the body's circadian rhythm, mounting an immune response to bacterial, viral, fungal and parasitic infections, replacing or remodeling injured tissue by stimulating fibroblast growth and, as the name suggests, killing certain tumors. TNF-α has been implicated as a mediator in inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, septic shock, endotoxic shock, atherosclerosis, ischemia-reperfusion injury, coronary heart disease, vasculitis, amyloidosis, multiple sclerosis, sepsis, chronic recurrent uveitis, hepatitis C virus infection, malaria, ulcerative colitis, cachexia, psoriasis, plasmocytoma, endometriosis, Behcet's disease, Wegenrer's granulomatosis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, meningitis, ankylosing spondylitis, skin delayed type hypersensitivity disorders, Alzheimer's disease, systemic lupus erythematosus and allergic asthma. Much research has been conducted to study the effect of TNF-α and anti-TNF-α therapies. Studies in the area of cancer have shown that with TNF-α therapy it is important to balance the cytotoxicity and systemic toxicity of the potential drug candidates.

Rheumatoid arthritis (RA)—an autoimmune disorder, is a chronic, systemic, articular inflammatory disease in which the normally thin synovial lining of joints is replaced by an inflammatory, highly vascularized, invasive fibrocollagenase tissue (pannus), which is destructive to both cartilage and bone. Areas that may be affected include the joints of the hands, wrists, neck, jaw, elbows, feet and ankles. Cartilage destruction in RA is linked to aberrant cytokines and growth factor expression in the affected joints.

Another inflammatory disorder, inflammatory bowel disease (IBD) is a group of disorders that cause inflammation of the intestines. The inflammation lasts for a long time and usually relapses. The two major types of IBD are Crohn's disease and ulcerative colitis.

Crohn's disease occur when the lining and wall of the intestines becomes inflamed resulting in the development of ulcers. Although Crohn's disease can occur in any part of the digestive system, it often occurs in the lower part of the small intestine where it joins the colon.

Ulcerative colitis is a chronic inflammatory disease of unknown etiology afflicting the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Signs and symptoms of the disease include cramping, lower abdominal pain, rectal bleeding, and frequent, loose discharges consisting mainly of blood, pus, and mucus with scanty fecal particles. A total colectomy may be required for acute, severe or chronic, unremitting ulcerative colitis.

Atherosclerosis is another inflammatory disorder, which affects arterial blood vessels. It is a chronic inflammatory response in the walls of arteries, in large part due to the deposition of lipoproteins (plasma proteins that carry cholesterol and triglycerides). It is commonly referred to as "hardening" or "furring" of the arteries. It is caused by the formation of multiple plaques within the arteries resulting in the inflammation of the arteries.

The first line of treatment for inflammatory disorders involves the use of non-steroidal anti-inflammatory drugs (NSAIDs) e.g. ibuprofen, naproxen to alleviate symptoms such as pain. However, despite the widespread use of NSAIDs, many individuals cannot tolerate the doses necessary to treat the disorder over a prolonged period of time as NSAIDs are known to cause gastric erosions. Moreover, NSAIDs merely treat the symptoms of disorder and not the cause. When patients fail to respond to NSAIDs, other drugs such as methotrexate, gold salts, D-penicillamine and corticosteroids are used. These drugs also have significant toxic effects. Monoclonal antibody drugs such as Infliximab, Etanercept and Adalimumab are useful as anti-inflammatory agents, but have drawbacks such as route of administration (only parenteral), high cost, allergy induction, activation of latent tuberculosis, increased risk of cancer and congestive heart disease.

WO 2007036900 (describes a TNF-α inhibitor, 7-hydroxyeudesm-4-en-6,12-olide, which is isolated from the plant *Sphaeranthus indicus*.

WO2006134609 discloses derivatives prepared from 7α-hydroxyeudesm-4-en-6,12-olide (also referred to as 7-hydroxyfrullanolide).

Indian Journal of Chemistry Vol. 33B, 1203-1204, 1994 describes photo-oxidation of 7-hydroxyeudesmanolide.

Indian Journal of Chemistry Vol. 25 B, 233-238, 1986 describes isolation of sesquiterpenoid hydroxy lactones from the plant *Sphaeranthus indicus*. The stereochemistry of these lactones was determined via adduct formation with morpholine.

J. Chem. Soc. Perkin Trans 157-160, 1988 describes derivatives prepared from the sesquiterpene lactone 7α-hydroxyeudesm-4-en-6,12-olide.

SUMMARY OF INVENTION

The present invention relates to derivatives of 7α-hydroxyeudesm-4-en-6,12-olide, processes for their preparation and their use in the treatment of inflammatory disorders, such as those caused by elevated levels of TNF-α and/or interleukins such as IL-1β, IL-6 and IL-8.

Thus according to one aspect of the present invention, there are provided tricyclic compounds of general formula 1 (as provided herein below), as well as stereoisomers, tautomeric forms, pharmaceutically acceptable salts, solvates, polymorphs and prodrugs thereof.

According to a further aspect of the present invention, there are provided processes for producing tricyclic compounds of general formula 1.

According to a further aspect, there is provided the use of tricyclic compounds of general formula 1 in the treatment of inflammatory disorders, such as those caused by elevated levels of proinflammatory cytokines such as TNF-α and/or interleukins such as IL-1β, IL-6, and IL-8.

According to another aspect of the present invention, there are provided pharmaceutical compositions including tricyclic compounds of general formula 1 as active ingredient.

According to another aspect of the present invention, there is provided a method for the treatment of inflammatory disorders, such as those caused by elevated levels of proinflammatory cytokines such as TNF-α, and/or interleukins such as IL-1β, IL-6, and IL-8, the method including administering to a mammal in need thereof a therapeutically effective amount of a compound of general formula 1.

According to another aspect of the present invention, there are provided methods for the manufacture of medicaments including tricyclic compounds of general formula 1 which are useful for the treatment of inflammatory disorders, such as those caused by elevated levels of proinflammatory cytokines such as TNF-α, and/or interleukins such as IL-1β, IL-6, and IL-8.

DETAILED DESCRIPTION OF INVENTION

The present invention provides tricyclic compounds represented by the following general formula 1:

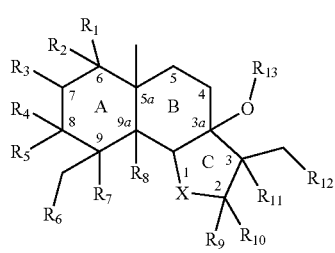

Formula 1 in all its stereoisomeric and tautomeric forms and mixtures thereof in all ratios, and its pharmaceutically acceptable salts, pharmaceutically acceptable solvates, pharmaceutically acceptable polymorphs and prodrugs, wherein $R_1$, $R_2$, $R_3$, $R_4$ and $R_5$ are each independently selected from hydrogen, alkyl, halogen, hydroxy, alkoxy, —OC(O)$R_{14}$, and —C(O)$R_{14}$; optionally $R_1$ is absent and $R_2$ is =O; optionally $R_4$ is absent and $R_5$ is =O;

ring A optionally contains one or two double bonds;

$R_5$ is absent when the double bond is formed between carbon numbers 7 and 8;

$R_6$ is selected from hydrogen, alkyl, cycloalkyl, halogen, hydroxy, alkoxy, —OC(O)$R_{14}$, —C(O)$R_{14}$ and —NR$_{15}$R$_{16}$;

$R_7$ and $R_8$ are hydrogens or may together form an optionally substituted ring, which optionally contains a heteroatom; $R_7$ and $R_8$ are absent when the double bond is formed between carbon numbers 9 and 9a;

ring C optionally contains one double bond between X and carbon number 2;

$R_9$ is absent when the double bond is formed between X and carbon number 2;

$R_9$ and $R_{10}$ are each independently selected from hydrogen, alkyl, halogen, —OR$_{13}$, —NHR$_{14}$ and —SR$_{14}$; or $R_9$ is absent and $R_{10}$ is selected from =O, =NR$_{14}$, and =S;

$R_{11}$ is selected from hydrogen, hydroxy, alkoxy, —OC(O)$R_{14}$, —C(O)$R_{14}$, and —NR$_{15}$R$_{16}$;

$R_{12}$ is selected from alkyl, cycloalkyl, alkoxy, hydroxy, aryl, heterocyclyl, —OC(O)$R_{14}$, —C(O)$R_{14}$, azido, —NR$_{15}$R$_{16}$, —S(O)$_m$R$_{17}$, and —OS(O)$_m$R$_{17}$;

X is selected from O, S, and —NR$_{14}$;

$R_{13}$ is selected from hydrogen, alkyl, and —C(O)$R_{14}$;

$R_{14}$ is selected from hydrogen and alkyl;

$R_{15}$ and $R_{16}$ are each independently selected from hydrogen, alkyl, cycloalkyl, aralkyl, aryl, heterocyclyl, —C(O)$R_{14}$ and —C(S)—NHR$_{14}$; or $R_{15}$ and $R_{16}$, together with the N atom to which they are bonded, form a 5-, 6-, or 7-membered heterocyclic ring, optionally having one or more additional heteroatoms selected from: O, N and S;

$R_{17}$ is selected from hydrogen, alkyl, cycloalkyl, aryl and heterocyclyl;

m is the integer 0, 1 or 2;

where alkyl or cycloalkyl are unsubstituted or substituted by one or two of the same or different groups selected from: alkyl, cycloalkyl, aralkyl, trifluoromethyl, halogen, carboxy, acetoxy, alkoxy, aryloxy, aryl and heterocyclyl;

aryl is unsubstituted or substituted by one or two of the same or different groups selected from: alkyl, trifluoromethyl, hydroxy, alkoxy, halogen, nitro and amino;

heterocyclyl is unsubstituted or substituted by one or two of the same or different groups selected from: alkyl, cycloalkyl, trifluoromethyl, halogen, hydroxy, alkoxy, oxo, amino and aryl;

halogen is selected from fluorine, chlorine, bromine and iodine; and with the proviso that (i) when $R_1$, $R_2$, $R_3$, $R_4$, $R_5$ and $R_6$ are hydrogens; double bond is formed between carbon numbers 9 and 9a, and $R_7$ and $R_8$ are absent; $R_9$ is absent and $R_{10}$ is =O; $R_{11}$ is hydrogen, $R_{12}$ is —NR$_{15}$R$_{16}$; $R_{13}$ is hydrogen; X is O; then $R_{15}$ and $R_{16}$ together with the N atom to which they are bonded do not form piperidine ring which is unsubstituted; and (ii) when $R_1$, $R_2$, $R_3$, $R_4$, $R_5$ and $R_6$ are hydrogens; double bond is formed between carbon numbers 9 and 9a and $R_7$ and $R_8$ are absent; $R_9$ is absent and $R_{10}$ is =O; $R_{11}$ is hydrogen, $R_{12}$ is $-NR_{15}R_{16}$; $R_{13}$ is hydrogen; X is O; then $R_{15}$ and $R_{16}$ together with the N atom to which they are bonded do not form a morpholine ring which is unsubstituted.

Definitions

Listed below are definitions, which apply to the terms as they are used throughout the specification and the appended claims (unless they are otherwise limited in specific instances), either individually or as part of a larger group.

As used herein, the term "alkyl" whether used alone or as part of a substituent group, refers to the radical of saturated aliphatic groups, including straight or branched-chain containing from 1 to 6 carbon atoms. Furthermore, unless stated otherwise, the term "alkyl" includes unsubstituted alkyl groups as well as alkyl groups, which are substituted by one or more different substituents. Suitable alkyl residues contain from 1 to 6 carbon atoms, for example, from 1 to 4 carbon atoms, such as methyl, ethyl, propyl, isopropyl, n-butyl, isobutyl, t-butyl. Unless stated otherwise, alkyl groups can be unsubstituted or substituted by one or more identical or different substituents. Any kind of substituent present in substituted alkyl residues can be present in any desired position provided that the substitution does not lead to an unstable molecule. A substituted alkyl refers to an alkyl residue in which one or more, for example, 1, 2, 3, 4 or 5 hydrogen atoms are replaced with substituents, for example, substituted or unsubstituted forms of alkyl, aryl, halogen, hydroxyl, carbonyl, carboxyl, alkoxyl, cycloalkyl, ester, ether, cyano, amino, amido, imino, alkylthio, thioester, sulfonyl, nitro, fluoroalkyls, aralkyl, acyloxy, heterocyclyl, aryl or heteroaryl group, and the like.

As used herein, the term "alkoxyl" or "alkoxy" refers to an alkyl group having an oxygen radical attached thereto, wherein alkyl is as defined above. The terms include, therefore, alkoxyl or alkoxy groups which are substituted by one or more identical or different groups. Representative alkoxyl groups include methoxy, ethoxy, propoxy, tert-butoxy group.

The term "cycloalkyl" refers to a saturated mono-, bi- or poly-cyclic ring system containing a specified number of carbon atoms. Cycloalkyls have 3, 4, 5, 6 or 7 carbon atoms in each ring structure. Examples of cycloalkyl residues containing 3, 4, 5, 6 or 7 ring carbon atoms are cyclopropyl, cyclobutyl, cyclopentyl, cyclohexyl or cycloheptyl. Furthermore, unless stated otherwise, the term 'cycloalkyl' includes unsubstituted cycloalkyl and cycloalkyl which is substituted by one or more identical or different groups selected from alkyl, aminoalkyl, alkoxy, amino carboxy, carbonyl-substituted alkyl, halo, haloalkyl, fluoroalkyls such as $-CF_3$, aryl, heteroaryl group.

As used herein, the term "acyl" refers to any group or organic radical such as alkyl (which can be further substituted with an alkyl, alkoxy, cycloalkylamino, hydroxy or halo) or cycloalkyl attached to a carbonyl group, wherein alkyl and cycloalkyl are as defined above.

As used herein, the term "aryl" refers to a monocyclic or polycyclic hydrocarbon group having up to 10 ring carbon atoms, in which at least one carbocyclic ring is present that has a conjugated π electron system. Examples of aryl residues include phenyl and naphthyl. Unless stated otherwise, aryl residues, for example phenyl or naphthyl, can be unsubstituted or optionally substituted by one or more substituents, for example, up to five identical or different substituents selected from the group consisting of halogen, alkyl, hydroxyalkyl fluoroalkyl (e.g., $CF_3$), hydroxyl, alkoxy, aryloxy, amino, cyano, nitro, oxime, thiol, imine, amide, carbonyl, sulfonyl, aminoacid ester, carboxylic acid, carboxylic acid alkyl esters, aryl and a heterocyclyl group, which can be saturated, partially unsaturated, or aromatic.

Aryl residues can be bonded via any desired position, and in substituted aryl residues, the substituents can be located in any desired position. For example, in monosubstituted phenyl residues the substituent can be located in the 2-position, the 3-position, the 4-position or the 5-position. If the phenyl group carries two substituents, they can be located in 2,3-position, 2,4-position, 2,5-position, 2,6-position, 3,4-position or 3,5-position.

The term "heteroatom" refers to nitrogen, oxygen and sulfur. It should be noted that any heteroatom with unsatisfied valences is assumed to have a hydrogen atom to satisfy the valences. The ring heteroatoms can be present in any desired number and in any position with respect to each other provided that the resulting heterocyclic system is stable and suitable as a subgroup in a drug substance.

The terms "heterocyclyl", "heterocyclic" "heterocycle" and "heterocyclo" refer to a saturated, partially unsaturated or aromatic monocyclic or polycyclic ring system containing 3, 4, 5, 6, 7, 8, 9, 10, 11, 12, 13 or 14 ring atoms of which 1, 2, 3 or 4 are identical or different heteroatoms selected from: nitrogen, oxygen and sulfur. The heterocyclyl group may, for example, have 1 or 2 oxygen atoms and/or 1 or 2 sulfur atoms and/or 1 to 4 nitrogen atoms in the ring. Monocyclic heterocyclyl groups include 3-membered, 4-membered, 5-membered, 6-membered and 7-membered rings. Suitable examples of such heterocyclyl groups are pyrrolyl, imidazolyl, pyrrolidinyl pyridinyl, pyrazinyl, pyridazinyl, pyrimidinyl, pyrazolyl, triazolyl, tetrazolyl, piperidinyl, piperazinyl, morpholinyl, thiomorpholinyl, tetrahydropyranyl, lactam, azepinyl, diazepinyl, triazinyl.

Polycyclic heterocyclyl groups can include two fused rings (bicyclic), one of which is a 5-, 6- or 7-membered heterocyclic ring and the other of which is a 5-, 6- or 7-membered carbocyclic or heterocyclic ring. Exemplary bicyclic heterocyclic groups include benzoxazolyl, quinolyl, isoquinolyl, indolyl, isoindolyl, and benzofurazanyl. Polycyclic heterocyclyl groups can include three fused rings (tricyclic), at least one of which is a 5-, 6- or 7-membered heterocyclic ring and the other two of which are 5-, 6- or 7-membered carbocyclic or heterocyclic rings. Exemplary tricyclic heterocyclic groups include substituted or unsubstituted naphthofuranyl, benzoindole, pyrroloquinoline, furoquinoline.

Heterocyclyl includes saturated heterocyclic ring systems, which do not contain any double bonds within the rings, as well as unsaturated heterocyclic ring systems which contain one or more, up to 5 double bonds within the rings provided that the resulting system is stable. Unsaturated rings may be non-aromatic or aromatic. Aromatic heterocyclyl groups may also be referred to by the customary term "heteroaryl" for which all the definitions and explanations above and below relating to heterocyclyl apply.

Unless stated otherwise, the heterocyclyl group can be unsubstituted or substituted with one or more (e.g., up to 5), identical or different, substituents. Examples of substituents for the ring carbon and ring nitrogen atoms are: alkyl, alkoxy, halogen, hydroxyl, hydroxyalkyl such as, for example, hydroxyethyl, fluoroalkyl such as $CF_3$, aryloxy, amino, cyano, nitro, thiol, imine, amide, carbonyl, sulfonyl, aminoacid ester, heterocyclyl, aryl and the like. The substituents can be present at one or more positions provided that a stable molecule results.

As used herein the term "aralkyl" refers to an alkyl group substituted with an aryl or heteroaryl group, wherein the terms alkyl, aryl and heteroaryl are as defined above. Exemplary aralkyl groups include $-(CH_2)_p$-phenyl, $-(CH_2)_p$- pyridyl, wherein p is an integer from 1 to 3. The aralkyl group may be further substituted with alkyl, hydroxy, halogen, cyano, nitro, amino, aryl and heteroaryl and the like.

The term "halogen" refers to fluorine, chlorine, bromine or iodine.

The term "amino" refers to unsubstituted, mono-substituted and di-substituted amino groups.

As used herein, the terms mono- or di-substituted amino refer respectively to an amino group substituted by one or two groups which may be the same or different. The substituents on the amino group are independently selected from: alkyl, haloalkyl, hydroxyalkyl, alkoxyalkyl, acyl, haloacyl, heterocyclylalkyl, heteroaryalkyl, aminoalkyl, alkoxyaralkyl and the like. It will be understood by those skilled in the art that the moieties on the amino group can themselves be substituted, if appropriate.

As used herein the term "saturated carbocyclic or heterocyclic ring" refers to a ring which does not contain any double bond.

As used herein the term "partially unsaturated carbocyclic or heterocyclic ring" refers to a ring which contains at least one double bond.

It will be understood that "substitution" or "substituted with" includes the implicit proviso that such substitution is in accordance with permitted valence of the substituted atom and the substituent, as well as results in a stable compound, which does not readily undergo transformation such as by rearrangement, cyclization, elimination, etc.

Embodiments of the Invention

In one embodiment, the present invention provides tricyclic compounds represented by general formula 1,

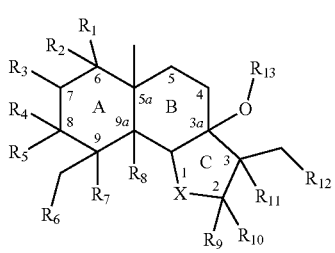

Formula 1 wherein $R_1$, $R_2$, $R_3$, $R_4$ and $R_5$ are each independently selected from hydrogen, alkyl, halogen, hydroxy, alkoxy, —OC(O)$R_{14}$, -and —C(O)$R_{14}$;

optionally $R_1$ is absent and $R_2$ is =O;

optionally $R_4$ is absent and $R_5$ is =O;

ring A optionally contains one or two double bonds;

$R_5$ is absent when a double bond is formed between carbon numbers 7 and 8;

$R_6$ is selected from hydrogen, alkyl, cycloalkyl, halogen, hydroxy, alkoxy, —OC(O)$R_{14}$, —C(O)$R_{14}$ and —NR$_{15}$R$_{16}$;

$R_7$ and $R_8$ are hydrogens or may together form an optionally substituted ring, which optionally contains a heteroatom;

$R_7$ and $R_8$ are absent when a double bond is formed between carbon numbers 9 and 9a;

ring C optionally contains one double bond between X and carbon number 2;

$R_9$ is absent when the double bond is formed between X and carbon number 2;

$R_9$ and $R_{10}$ are each independently selected from hydrogen, alkyl, halogen, —OR$_{13}$, NHR$_{14}$ and SR$_{14}$; or $R_9$ is absent and $R_{10}$ is selected from =O, =NR$_{14}$ and =S;

$R_{11}$ is selected from hydrogen, hydroxy, alkoxy, —OC(O)R$_{14}$, —C(O)R$_{14}$ and —NR$_{15}$R$_{16}$;

$R_{12}$ is selected from alkyl, cycloalkyl, alkoxy, hydroxy, aryl, heterocyclyl, —OC(O)R$_{14}$, —C(O)R$_{14}$, azido, —NR$_{15}$R$_{16}$, —S(O)$_m$R$_{17}$, and —OS(O)$_m$R$_{17}$;

X is selected from O, S, and —NR$_{14}$;

$R_{13}$ is selected from hydrogen, alkyl, and —C(O)R$_{14}$;

$R_{14}$ is selected from hydrogen and alkyl;

$R_{15}$ and $R_{16}$ are each independently selected from hydrogen, alkyl, cycloalkyl, aralkyl, aryl, heterocyclyl, C(O)R$_{14}$ and —C(S)—NHR$_{14}$; or $R_{15}$ and $R_{16}$, together with the N atom to which they are bonded, form a 5-, 6-, or 7-membered heterocyclic ring, optionally having one or more additional heteroatoms selected from: O, N and S;

$R_{17}$ is selected from hydrogen, alkyl, cycloalkyl, aryl and heterocyclyl;

m is an integer from 0 to 2;

where alkyl or cycloalkyl are unsubstituted or substituted by one or two of the same or different groups selected from: alkyl, cycloalkyl, aralkyl, trifluoromethyl, halogen, carboxy, acetoxy, alkoxy, aryloxy, aryl and heterocyclyl;

aryl is unsubstituted or substituted by one or two of the same or different groups selected from: alkyl, trifluoromethyl, hydroxy, alkoxy, halogen, nitro and amino;

heterocyclyl is unsubstituted or substituted by one or two of the same or different groups selected from: alkyl, cycloalkyl, trifluoromethyl, halogen, hydroxy, alkoxy, oxo, amino and aryl;

halogen is selected from fluorine, chlorine, bromine and iodine;

with the proviso that (i) when $R_1$, $R_2$, $R_3$, $R_4$, $R_5$ and $R_6$ are hydrogens; double bond is formed between carbon numbers 9 and 9a, and $R_7$ and $R_8$ are absent; $R_9$ is absent and $R_{10}$ is =O; $R_{11}$ is hydrogen, $R_{12}$ is —NR$_{15}$R$_{16}$; $R_{13}$ is hydrogen; X is O; then $R_{15}$ and $R_{16}$ together with the N atom to which they are bonded do not form piperidine ring which is unsubstituted; and (ii) when $R_1$, $R_2$, $R_3$, $R_4$, $R_5$ and $R_6$ are hydrogens; double bond is formed between carbon numbers 9 and 9a and $R_7$ and $R_8$ are absent; $R_9$ is absent and $R_{10}$ is =O; $R_{11}$ is hydrogen, $R_{12}$ is —NR$_{15}$R$_{16}$; $R_{13}$ is hydrogen; X is O; then $R_{15}$ and $R_{16}$ together with the N atom to which they are bonded do not form morpholine ring which is unsubstituted.

In another embodiment, the present invention provides tricyclic compounds represented by general formula 1, wherein $R_1$, $R_2$, $R_3$, $R_4$, $R_5$ and $R_6$ are each hydrogen;

double bond is formed between carbon numbers 9 and 9a; and $R_7$ and $R_8$ are absent;

$R_9$ is absent and $R_{10}$ is =O;

$R_{11}$ is hydrogen;

$R_{12}$ is selected from alkyl, cycloalkyl, alkoxy, hydroxy, aryl, heterocyclyl, —OC(O)R$_{14}$, —C(O)R$_{14}$, azido, —NR$_{15}$R$_{16}$, —S(O)$_m$R$_{17}$, and —OS(O)$_m$R$_{17}$;

X is selected from O and NR$_{14}$;

$R_{13}$ is selected from hydrogen, alkyl, and —C(O)R$_{14}$;

$R_{14}$ is selected from hydrogen and alkyl;

$R_{15}$ and $R_{16}$ are each independently selected from hydrogen, alkyl, cycloalkyl, aralkyl, aryl, heterocyclyl, —C(O)R$_{14}$, and C(S)—NHR$_{14}$; or $R_{15}$ and $R_{16}$, together with the N atom to which they are bonded, form a 5-, 6-, or 7-membered heterocyclic ring, optionally having one or more additional heteroatoms selected from: O, N and S;

$R_{17}$ is selected from hydrogen, alkyl, cycloalkyl, aryl and heterocyclyl;

m is an integer from 0 to 2;

where alkyl or cycloalkyl are unsubstituted or substituted by one or two of the same or different groups selected from: alkyl, cycloalkyl, aralkyl, trifluoromethyl, halogen, carboxy, acetoxy, alkoxy, aryloxy, aryl and heterocyclyl;

aryl is unsubstituted or substituted by one or two of the same or different groups selected from: alkyl, trifluoromethyl, hydroxy, alkoxy, halogen, nitro and amino;

heterocyclyl is unsubstituted or substituted by one or two of the same or different groups selected from: alkyl, cycloalkyl, trifluoromethyl, halogen, hydroxy, alkoxy, oxo, amino and aryl;

halogen is selected from fluorine, chlorine, bromine and iodine;

with the proviso that
(i) when $R_{12}$ is —$NR_{15}R_{16}$; $R_{13}$ is hydrogen; X is O; then $R_{15}$ and $R_{16}$ together with the N atom to which they are bonded do not form piperidine ring which is unsubstituted; and
(ii) when $R_{12}$ is —$NR_{15}R_{16}$; $R_{13}$ is hydrogen; X is O; then $R_{15}$ and $R_{16}$ together with the N atom to which they are bonded do not form morpholine ring which is unsubstituted.

In another embodiment, the present invention provides tricyclic compounds represented by general formula 1, wherein $R_1$, $R_2$, $R_3$, $R_4$, $R_5$ and $R_6$ are each hydrogen;
double bond is formed between carbon numbers 9 and 9a; and $R_7$ and $R_8$ are absent;
$R_9$ is absent and $R_{10}$ is =O; $R_{11}$ is hydrogen;
$R_{12}$ is selected from alkyl, cycloalkyl, alkoxy, hydroxy, —OC(O)$R_{14}$, —C(O)$R_{14}$, —$NR_{15}R_{16}$, aryl and heterocyclyl;
X is O;
$R_{13}$ is hydrogen;
$R_{14}$ is selected from hydrogen and alkyl;
$R_{15}$ and $R_{16}$ are each independently selected from hydrogen, alkyl, cycloalkyl, aralkyl, aryl, heterocyclyl, —C(O)$R_{14}$, and C(S)—NH$R_{14}$; or $R_{15}$ and $R_{16}$, together with the N atom to which they are bonded, form a 5-, 6-, or 7-membered heterocyclic ring, optionally having one or more additional heteroatoms selected from: O, N and S; and with the provisos that,
(i) when $R_{12}$ is —$NR_{15}R_{16}$; then $R_{15}$ and $R_{16}$ together with the N atom to which they are bonded do not form a piperidine ring which is unsubstituted; and
(ii) when $R_{12}$ is —$NR_{15}R_{16}$; then $R_{15}$ and $R_{16}$ together with the N atom to which they are bonded do not form a morpholine ring which is unsubstituted.

In a further embodiment, the present invention provides tricyclic compounds represented by general formula 1, wherein $R_1$, $R_2$, $R_3$, $R_4$, $R_5$ and $R_6$ are each hydrogen;
double bond is formed between carbon numbers 9 and 9a; and $R_7$ and $R_8$ are absent;
$R_9$ is absent and $R_{10}$ is =O;
$R_{11}$ is hydrogen;
$R_{12}$ is —$NR_{15}R_{16}$;
X is O;
$R_{13}$ is hydrogen; and
$R_{15}$ and $R_{16}$, together with the N atom to which they are bonded, form a 5-, 6- or 7-membered heterocyclyl, optionally having one or more additional heteroatoms selected from: O, N and S; wherein the heterocyclyl is selected from unsubstituted or substituted pyrrolyl, imidazolyl, oxazolyl, isoxazolyl, thiazolyl, isothiazolyl, triazolyl, tetrazolyl, pyrazolyl, pyridinyl, pyrazinyl, pyridazinyl, pyrimidinyl, azepinyl, diazepinyl, triazepinyl, thiomorpholinyl, tetrahydropyranyl, lactam, pyrrolidinyl, azetidinyl, piperazinyl, substituted morpholinyl, and substituted piperidinyl.

In another embodiment, the present invention provides tricyclic compounds represented by general formula 1, wherein $R_1$, $R_2$, $R_3$, $R_4$, $R_5$ and $R_6$ are each hydrogen; double bond is formed between carbon numbers 9 and 9a; and $R_7$ and $R_8$ are absent;
$R_9$ is absent and $R_{10}$ is =O;
$R_{11}$ is hydrogen;
$R_{12}$ is selected from 1H-pyrazol-1-yl, 3,5-dimethyl-1H-pyrazol-1-yl, 2-methyl-1H-imidazol-1-yl, 1H-1,2,4-triazol-1-yl, 2-carboxy-pyrrolidin-1-yl, 4-oxo-piperidin-1-yl, 4-hydroxy piperidin-1-yl, 1,4'bipiperidin-1-yl, thiomorpholin-4-yl, and 1-oxo-thiomorpholin-4-yl;
X is O; and
$R_{13}$ is hydrogen.

In a further embodiment, the present invention provides tricyclic compounds represented by general formula 1, wherein $R_1$, $R_2$, $R_3$, $R_4$, $R_5$ and $R_6$ are each hydrogen;
double bond is formed between carbon numbers 9 and 9a; and $R_7$ and $R_8$ are absent;
$R_9$ is absent and $R_{10}$ is =O;
$R_{11}$ is hydrogen;
$R_{12}$ is unsubstituted or substituted piperazinyl;
X is O; and
$R_{13}$ is hydrogen.

In a further embodiment, the present invention provides tricyclic compounds represented by general formula 1, wherein $R_1$, $R_2$, $R_3$, $R_4$, $R_5$ and $R_6$ are each hydrogen;
double bond is formed between carbon numbers 9 and 9a, and $R_7$ and $R_8$ are absent;
$R_9$ is absent and $R_{10}$ is =O;
$R_{11}$ is hydrogen;
$R_{12}$ is selected from piperazin-1-yl, 4-methylpiperazin-1-yl, 4-benzylpiperazin-1-yl, 4-(2,6-dimethylbenzyl)piperazin-1-yl, 4-(3,5-dimethoxy-2-methylbenzyl)piperazin-1-yl, 4-(2-(hydroxymethyl)-3,5-dimethoxy-6-methylbenzyl)piperazin-1-yl, 4-(2-fluorobenzyl)piperazin-1-yl, 4-(perfluorobenzyl)piperazin-1-yl, 4-(2-chloro-6-fluorobenzyl)piperazin-1-yl, 4-(2-fluoro-6-(trifluoromethyl)benzyl)piperazin-1-yl, 4-(benzo[d][1,3]dioxol-4-ylmethyl) piperazin-1-yl, 4-(2-(hydroxymethyl)-3,5-dimethoxybenzyl)piperazin-1-yl, 4-phenethyl piperazin-1-yl, 4-acetylpiperazin-1-yl, 4-phenylpiperazin-1-yl, 4-o-tolylpiperazin-1-yl, 4-(2-methoxyphenyl)piperazin-1-yl, 4-(2-chlorophenyl)piperazin-1-yl, 4-(pyridin-2-yl)piperazin-1-yl, and groups of the formula:

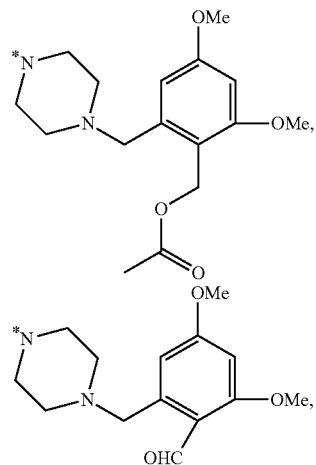

-continued

[chemical structures]

* indicates point of attachment

X is O; and

R$_{13}$ is hydrogen.

In a further embodiment, the present invention provides tricyclic compounds represented by general formula 1, wherein R$_1$, R$_2$, R$_3$, R$_4$, R$_5$ and R$_6$ are each hydrogen;

double bond is formed between carbon numbers 9 and 9a, and R$_7$ and R$_8$ are absent;

R$_9$ is absent and R$_{10}$ is =O;

R$_{11}$ is hydrogen;

R$_{12}$ is —NR$_{15}$R$_{16}$;

R$_{13}$ is hydrogen;

X is O;

R$_{15}$ is selected from hydrogen and alkyl; and

R$_{16}$ is selected from unsubstituted or substituted alkyl, cycloalkyl, aralkyl and aryl.

In a further embodiment, the present invention provides tricyclic compounds represented by general formula 1, wherein R$_1$, R$_2$, R$_3$, R$_4$, R$_5$ and R$_6$ are each hydrogen;

double bond is formed between carbon numbers 9 and 9a, and R$_7$ and R$_8$ are absent;

R$_9$ is absent and R$_{10}$ is =O;

R$_{11}$ is hydrogen;

R$_{12}$ is —NR$_{15}$R$_{16}$;

R$_{13}$ is hydrogen;

R$_{15}$ is selected from hydrogen and methyl;

R$_{16}$ is selected from the groups of formula:

[chemical structures]

and

* indicates point of attachment

X is O;

In a further embodiment, the present invention provides tricyclic compounds represented by general formula 1, wherein R$_1$, R$_2$, R$_3$, R$_4$, R$_5$ and R$_6$ are each hydrogen;

double bond is formed between carbon numbers 9 and 9a, and R$_7$ and R$_8$ are absent;

R$_9$ is absent and R$_{10}$ is =O;

R$_{11}$ is hydrogen;

R$_{12}$ is —NR$_{15}$R$_{16}$;

R$_{13}$ is hydrogen;

R$_{14}$ is selected from hydrogen and alkyl;

R$_{15}$ is selected from alkyl, —C(O)R$_{14}$, and —C(S)—NHR$_{14}$;

R$_{16}$ is a group of formula:

[chemical structure]

and

* indicates point of attachment

X is O;

In a further embodiment, the present invention provides tricyclic compounds represented by general formula 1, wherein R$_1$, R$_2$, R$_3$, R$_4$, R$_5$ and R$_6$ are each hydrogen;

double bond is formed between carbon numbers 9 and 9a, and R$_7$ and R$_8$ are absent;

R$_9$ is absent and R$_{10}$ is =O;

R$_{11}$ is hydrogen;

R$_{12}$ is —NR$_{15}$R$_{16}$;

$R_{13}$ is hydrogen;
$R_{15}$ is selected from —C(O)CH$_3$ and —C(S)—NHCH$_2$CH$_3$;
$R_{16}$ is a group of formula:

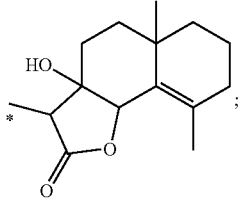

and
* indicates point of attachment
X is O;
In a further embodiment, the present invention provides tricyclic compounds represented by general formula 1,
wherein
$R_1$, $R_2$, $R_3$, $R_4$, $R_5$ and $R_6$ are each hydrogen;
double bond is formed between carbon numbers 9 and 9a, and $R_7$ and $R_8$ are absent;
$R_9$ is absent and $R_{10}$ is =O;
$R_{11}$ is hydrogen;
$R_{12}$ is —S(O)$_m$R$_{17}$;
X is O;
$R_{13}$ is hydrogen;
$R_{17}$ is selected from hydrogen, alkyl, cycloalkyl, aryl and heterocyclyl; and
m is an integer from 0 to 2.
In a further embodiment, the present invention provides tricyclic compounds represented by general formula 1,
wherein $R_1$, $R_2$, $R_3$, $R_4$, $R_5$ and $R_6$ are each hydrogen;
double bond is formed between carbon numbers 9 and 9a, and $R_7$ and $R_8$ are absent;
$R_9$ is absent and $R_{10}$ is =O;
$R_{11}$ is hydrogen;
$R_{12}$ is selected from —S—CH$_2$COOH and —S—C$_6$H$_5$;
X is O; and
$R_{13}$ is hydrogen.
In a further embodiment, the present invention provides tricyclic compounds represented by general formula 1,
wherein $R_1$, $R_2$, $R_3$, $R_4$, $R_5$ and $R_6$ are each hydrogen;
$R_7$ and $R_8$ together form an optionally substituted ring, which optionally contains a heteroatom;
$R_9$ is absent and $R_{10}$ is =O;
$R_{11}$ is hydrogen;
$R_{12}$ is —NR$_{15}$R$_{16}$;
X is O;
$R_{13}$ is hydrogen; and
$R_{15}$ and $R_{16}$ are each independently selected from hydrogen, alkyl, cycloalkyl, aralkyl, aryl or heterocyclyl, or $R_{15}$ and $R_{16}$, together with the N atom to which they are bonded, form a 5-, 6- or 7-membered heterocyclyl, optionally having one or more additional heteroatoms selected from: O, N and S, wherein the heterocyclyl group is selected from unsubstituted or substituted pyrrolyl, pyrazolyl, pyrazinyl, morpholinyl, thiomorpholinyl, pyrrolidinyl, piperidinyl and piperazinyl.
In a further embodiment, the present invention provides tricyclic compounds represented by general formula 1,
wherein $R_1$, $R_2$, $R_3$, $R_4$, $R_5$ and $R_6$ are each hydrogen;
$R_7$ and $R_8$ together form an optionally substituted ring containing an oxygen atom;
$R_9$ is absent and $R_{10}$ is =O;
$R_{11}$ is hydrogen;
$R_{12}$ is —NR$_{15}$R$_{16}$;
X is O;
$R_{13}$ is hydrogen; and
$R_{15}$ and $R_{16}$ are each independently selected from hydrogen, alkyl, cycloalkyl, aralkyl, aryl or heterocyclyl, or $R_{15}$ and $R_{16}$, together with the N atom to which they are bonded, form a 5-, 6- or 7-membered heterocyclyl, optionally having one or more additional heteroatoms selected from: O, N and S, wherein the heterocyclyl group is selected from unsubstituted or substituted pyrrolyl, pyrazolyl, pyrazinyl, morpholinyl, thiomorpholinyl, pyrrolidinyl, piperidinyl and piperazinyl.
In a further embodiment, the present invention provides tricyclic compounds represented by general formula 1,
wherein $R_1$, $R_2$, $R_3$, $R_4$, $R_5$ and $R_6$ are each hydrogen;
$R_7$ and $R_8$ together form an epoxide ring;
$R_9$ is absent and $R_{10}$ is =O;
$R_{11}$ is hydrogen;
$R_{12}$ is piperidine;
X is O; and
$R_{13}$ is hydrogen.
In another embodiment, the present invention provides tricyclic compounds represented by general formula 1,
wherein
$R_1$, $R_2$, $R_3$, $R_4$, $R_5$ and $R_6$ are each hydrogen;
double bond is formed between carbon numbers 9 and 9a, and $R_7$ and $R_8$ are absent;
$R_9$ is absent and $R_{10}$ is =O;
$R_{11}$ is hydroxy;
$R_{12}$ is selected from alkyl, cycloalkyl, alkoxy, hydroxy, aryl, heterocyclyl, —OC(O)R$_{14}$, —C(O)R$_{14}$, azido, —NR$_{15}$R$_{16}$, —S(O)$_m$R$_{17}$, and —OS(O)$_m$R$_{17}$;
X is O;
$R_{13}$ is hydrogen;
$R_{14}$ is selected from hydrogen and alkyl;
$R_{15}$ and $R_{16}$ are each independently selected from hydrogen, alkyl, cycloalkyl, aralkyl, aryl, heterocyclyl, —C(O)R$_{14}$ and —C(S)—NHR$_{14}$; or $R_{15}$ and $R_{16}$, together with the N atom to which they are bonded, form a 5-, 6-, or 7-membered heterocyclic ring, optionally having one or more additional heteroatoms selected from: O, N and S;
$R_{17}$ is selected from hydrogen, alkyl, cycloalkyl, aryl and heterocyclyl; and
m is an integer from 0 to 2.
In a further embodiment, the present invention provides tricyclic compounds represented by general formula 1,
wherein, $R_1$, $R_2$, $R_3$, $R_4$, $R_5$ and $R_6$ are each hydrogen;
double bond is formed between carbon numbers 9 and 9a, and $R_7$ and $R_8$ are absent;
$R_9$ is absent and $R_{10}$ is =O;
$R_{11}$ is hydroxy;
$R_{12}$ is selected from hydroxy, —OC(O)CH$_3$, —OS(O)$_2$—C$_6$H$_5$-4-CH$_3$, azido, piperazin-1-yl, and a group of formula:

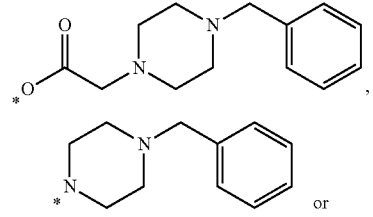

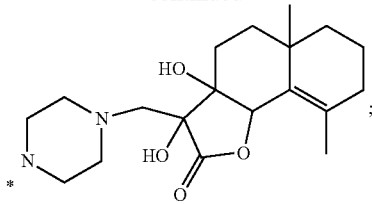

* indicates point of attachment
X is O; and
$R_{13}$ is hydrogen.

In another embodiment, the present invention provides tricyclic compounds represented by general formula 1,
wherein $R_1$, $R_2$, $R_3$, $R_4$, $R_5$, $R_6$, $R_7$ and $R_8$ are each hydrogen;
$R_9$ is absent and $R_{10}$ is =O;
$R_{11}$ is hydrogen;
$R_{12}$ is —$NR_{15}R_{16}$;
X is O;
$R_{13}$ is hydrogen; and
$R_{15}$ and $R_{16}$, together with the N atom to which they are bonded, form a 5-, 6- or 7-membered heterocyclyl, optionally having one or more additional heteroatoms selected from: O, N and S; wherein the heterocyclyl is selected from unsubstituted or substituted pyrrolyl, imidazolyl, oxazolyl, isoxazolyl, thiazolyl, isothiazolyl, triazolyl, tetrazolyl, pyrazolyl, pyridinyl, pyrazinyl, pyridazinyl, pyrimidinyl, azepinyl, diazepinyl, triazepinyl, thiomorpholinyl, tetrahydropyranyl, lactam, pyrrolidinyl, azetidinyl, piperazinyl, morpholinyl, and piperidinyl.

In a further embodiment, the present invention provides tricyclic compounds represented by general formula 1,
wherein
$R_1$, $R_2$, $R_3$, $R_4$, $R_5$, $R_6$, $R_7$ and $R_8$ are each hydrogen;
$R_9$ is absent and $R_{10}$ is =O;
$R_{11}$ is hydrogen;
$R_{12}$ is selected from piperazinyl and morpholinyl;
X is O; and
$R_{13}$ is hydrogen;

In another embodiment, the present invention provides tricyclic compounds represented by general formula 1,
wherein $R_1$, $R_2$, $R_3$, $R_4$, $R_5$ and $R_6$ are each hydrogen;
double bond is formed between carbon numbers 9 and 9a, and $R_7$ and $R_8$ are absent;
$R_9$ is hydrogen and $R_{10}$ is selected from hydrogen, hydroxy and —OC(O)$R_{14}$;
$R_{11}$ is hydrogen;
$R_{12}$ is —$NR_{15}R_{16}$;
X is O;
$R_{13}$ is hydrogen;
$R_{14}$ is selected from hydrogen and alkyl; and
$R_{15}$ and $R_{16}$, together with the N atom to which they are bonded, form a 5-, 6- or 7-membered heterocyclyl, optionally having one or more additional heteroatoms selected from: O, N and S; wherein the heterocyclyl is selected from unsubstituted or substituted pyrrolyl, imidazolyl, oxazolyl, isoxazolyl, thiazolyl, isothiazolyl, triazolyl, tetrazolyl, pyrazolyl, pyridinyl, pyrazinyl, pyridazinyl, pyrimidinyl, azepinyl, diazepinyl, triazepinyl, thiomorpholinyl, tetrahydropyranyl, lactam, pyrrolidinyl, azetidinyl, piperazinyl, morpholinyl, and piperidinyl.

In a further embodiment, the present invention provides tricyclic compounds represented by general formula 1,
wherein $R_1$, $R_2$, $R_3$, $R_4$, $R_5$ and $R_6$ are each hydrogen;
double bond is formed between carbon numbers 9 and 9a, and $R_7$ and $R_8$ are absent;
$R_9$ is hydrogen and $R_{10}$ is selected from hydrogen, hydroxy and —OC(O)$R_{14}$;
$R_{11}$ is hydrogen;
$R_{12}$ is substituted piperazinyl;
X is O;
$R_{13}$ is hydrogen; and
$R_{14}$ is selected from hydrogen and alkyl.

Compounds of the present invention are selected from but not limited to:
(5aR,9bS)-3,3a-Dihydroxy-3-(hydroxymethyl)-5a,9-dimethyl-3,3a,4,5,5a,6,7,8-octahydronaphtho[1,2-b]furan-2(9bH)-one;
((5aR,9bS)-3,3a-Dihydroxy-5a,9-dimethyl-2-oxo-2,3,3a,4,5,5a,6,7,8,9b-decahydronaphtho[1,2-b]furan-3-yl)methyl acetate;
((5aR,9bS)-3,3a-dihydroxy-5a,9-dimethyl-2-oxo-2,3,3a,4,5,5a,6,7,8,9b-decahydronaphtho[1,2-b]furan-3-yl)methyl 2-(4-benzylpiperazin-1-yl)acetate;
((5aR,9bS)-3,3a-Dihydroxy-5a,9-dimethyl-2-oxo-2,3,3a,4,5,5a,6,7,8,9b-decahydro naphtho[1,2-b]furan-3-yl)methyl 4-methylbenzenesulfonate;
(5aR,9bS)-3-(Azidomethyl)-3,3a-dihydroxy-5a,9-dimethyl-3,3a,4,5,5a,6,7,8-octahydronaphtho[1,2-b]furan-2(9bH)-one;
(5aR,9bS)-3,3a-Dihydroxy-5a,9-dimethyl-3-(piperidin-1-ylmethyl)-3,3a,4,5,5a,6,7,8-octahydronaphtho[1,2-b]furan-2(9bH)-one;
(5aR,9bS)-3-((4-Benzylpiperazin-1-yl)methyl)-3,3a-dihydroxy-5a,9-dimethyl-3,3a,4,5,5a,6,7,8-octahydronaphtho[1,2-b]furan-2(9bH)-one;
(5aS,9bS)-3-((4-(((5aR,9bS)-3,3a-dihydroxy-5a,9-dimethyl-2-oxo-2,3,3a,4,5,5a,6,7,8,9b-decahydronaphtho[1,2-b]furan-3-yl)methyl)piperazin-1-yl)methyl)-3,3a-dihydroxy-5a,9-dimethyl-3,3a,4,5,5a,6,7,8-octahydronaphtho[1,2-b]furan-2(9bH)-one;
(5aR,9bS)-3a-Hydroxy-5a,9-dimethyl-3-(phenylthiomethyl)-3,3a,4,5,5a,6,7,8-octahydronaphtho[1,2-b]furan-2(9bH)-one;
2-(((5aR,9bS)-3a-Hydroxy-5a,9-dimethyl-2-oxo-2,3,3a,4,5,5a,6,7,8,9b-decahydronaphtho[1,2-b]furan-3-yl)methylthio)acetic acid;
(5aR,9bS)-3-((1H-Pyrazol-1-yl)methyl)-3a-hydroxy-5a,9-dimethyl-3,3a,4,5,5a,6,7,8-octahydronaphtho[1,2-b]furan-2(9bH)-one;
(5aR,9bS)-3-((3,5-Dimethyl-1H-pyrazol-1-yl)methyl)-3a-hydroxy-5a,9-dimethyl-3,3a,4,5,5a,6,7,8-octahydronaphtho[1,2-b]furan-2(9bH)-one;
(5aR,9bS)-3a-Hydroxy-5a,9-dimethyl-3-((2-methyl-1H-imidazol-1-yl)methyl)-3,3a,4,5,5a,6,7,8-octahydronaphtho[1,2-b]furan-2(9bH)-one;
(5aR,9bS)-3-((1H-1,2,4-Triazol-1-yl)methyl)-3a-hydroxy-5a,9-dimethyl-3,3a,4,5,5a,6,7,8-octahydronaphtho[1,2-b]furan-2(9bH)-one;
1-(((5aR,9bS)-3a-Hydroxy-5a,9-dimethyl-2-oxo-2,3,3a,4,5,5a,6,7,8,9b-decahydronaphtho[1,2-b]furan-3-yl)methyl)pyrrolidine-2-carboxylic acid;
13-(Piperidin-1-yl)-4,5-epoxy-7-hydroxyeudesm-6,12-olide;
1-(((5aR,9bS)-3a-Hydroxy-5a,9-dimethyl-2-oxo-2,3,3a,4,5,5a,6,7,8,9b-decahydronaphtho[1,2-b]furan-3-yl)methyl)piperidin-4-one;

(5aR,9bS)-3a-Hydroxy-3-((4-hydroxypiperidin-1-yl)methyl)-5a,9-dimethyl-3,3a, 4,5,5a,6,7,8-octahydronaphtho[1,2-b]furan-2(9bH)-one;

(5aR,9bS)-3-(1,4'-Bipiperidin-1'-ylmethyl)-3a-hydroxy-5a,9-dimethyl-3,3a,4,5,5a,6,7,8-octahydronaphtho[1,2-b]furan-2(9bH)-one;

(5aR,9bS)-3a-hydroxy-5a,9-dimethyl-3-morpholinomethyl)decahydronaphtho[1,2-b]furan-2(9bH)-one;

(5aR,9bS)-3a-Hydroxy-5a,9-dimethyl-3-(thiomorpholinomethyl)-3,3a,4,5,5a,6,7,8-octahydronaphtho[1,2-b]furan-2(9bH)-one;

(5aR,9bS)-3a-Hydroxy-5a,9-dimethyl-3-(thiomorpholino-1-oxide-methyl)-3,3a,4,5,5a,6,7,8-octahydronaphtho[1,2-b]furan-2(9bH)-one;

(5aR,9bS)-3a-hydroxy-5a,9-dimethyl-3-((4-methylpiperazin-1-yl)methyl)-3,3a,4,5,5a,6,7,8-octahydronaphtho[1,2-b]furan-2(9bH)-one hydrochloride;

(5aR,9bS)-3-((4-Benzylpiperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3a-hydroxy-5a,9-dimethyl-3-(piperazin-1-ylmethyl)-3,3a,4,5,5a,6,7,8-octahydronaphtho[1,2-b]furan-2(9bH)-one;

(5aR,9bS)-3a-hydroxy-5a,9-dimethyl-3-(piperazin-1-ylmethyl)decahydronaphtho[1,2-b]furan-2(9bH)-one;

(5aR,9bS)-3-((4-(2,6-dimethylbenzyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3-((4-(3,5-dimethoxy-2-methylbenzyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3a-hydroxy-3-((4-(2-(hydroxymethyl)-3,5-dimethoxy-6-methylbenzyl)piperazin-1-yl)methyl)-5a,9-dimethyl-3,3a,4,5,5a,6,7,8-octahydronaphtho[1,2-b]furan-2(9bH)-one;

(5aR,9bS)-3-((4-(2-fluorobenzyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3a-hydroxy-5a,9-dimethyl-3-((4-(perfluorobenzyl)piperazin-1-yl)methyl)-3,3a,4,5,5a,6,7,8-octahydronaphtho[1,2-b]furan-2(9bH)-one;

(5aR,9bS)-3-((4-(2-chloro-6-fluorobenzyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3-((4-(2-fluoro-6-(trifluoromethyl)benzyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3-((4-(benzo[d][1,3]dioxol-4-ylmethyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3a-hydroxy-3-((4-(2-(hydroxymethyl)-3,5-dimethoxybenzyl)piperazin-1-yl)methyl)-5a,9-dimethyl-3,3a,4,5,5a,6,7,8-octahydronaphtho[1,2-b]furan-2(9bH)-one 2-((4-(((5aR,9bS)-3a-hydroxy-5a,9-dimethyl-2-oxo-2,3,3a,4,5,5a,6,7,8,9b-decahydronaphtho[1,2-b]furan-3-yl)methyl)piperazin-1-yl)methyl)-4,6-dimethoxybenzyl acetate;

2-((4-(((5aR,9bS)-3a-hydroxy-5a,9-dimethyl-2-oxo-2,3,3a,4,5,5a,6,7,8,9b-decahydronaphtho[1,2-b]furan-3-yl)methyl)piperazin-1-yl)methyl)-4,6-dimethoxybenzaldehyde oxime;

2-((4-(((5aR,9bS)-3α-hydroxy-5a,9-dimethyl-2-oxo-2,3,3a,4,5,5a,6,7,8,9b-decahydronaphtho[1,2-b]furan-3-yl)methyl)piperazin-1-yl)methyl)-4,6-dimethoxybenzaldehyde;

2-((4-(((5aR,9bS)-3a-hydroxy-5a,9-dimethyl-2-oxo-2,3,3a,4,5,5a,6,7,8,9b-decahydronaphtho[1,2-b]furan-3-yl)methyl)piperazin-1-yl)methyl)-4,6-dimethoxybenzoic acid;

(5aR,9bS)-3-((4-benzylpiperazin-1-yl)methyl)-5a,9-dimethyl-2,3,3a,4,5,5a,6,7,8,9b-decahydronaphtho[1,2-b]furan-2,3a-diol;

(5aR,9bS)-3-((4-benzylpiperazin-1-yl)methyl)-3a-hydroxy-5a,9-dimethyl-2,3,3a,4,5,5a,6,7,8,9b-decahydronaphtho[1,2-b]furan-2-yl acetate;

(5aR,9bS)-3a-hydroxy-5a,9-dimethyl-3-((4-phenethylpiperazin-1-yl)methyl)-3,3a,4,5,5a,6,7,8-octahydronaphtho[1,2-b]furan-2(9bH)-one;

(5aR,9bS)-3-((4-benzylpiperazin-1-yl)methyl)-5a,9-dimethyl-2,3,3a,4,5,5a,6,7,8,9b-decahydronaphtho[1,2-b]furan-3a-ol;

(5aR,9bS)-3-((4-Acetylpiperazin-1-yl)methyl)-3a-hydroxy-5a,9-dimethyl-3,3a,4,5,5a,6,7,8-octahydronaphtho[1,2-b]furan-2(9bH)-one;

Ethyl 4-(((5aR,9bS)-3a-hydroxy-5a,9-dimethyl-2-oxo-2,3,3a,4,5,5a,6,7,8,9b-decahydronaphtho[1,2-b]furan-3-yl)methyl)piperazine-1-carboxylate hydrochloride;

(5aR,9bS)-3a-Hydroxy-5a,9-dimethyl-3-((4-phenylpiperazin-1-yl)methyl)-3,3a,4,5,5a,6,7,8-octahydronaphtho[1,2-b]furan-2(9bH)-one;

(5aR,9bS)-3a-Hydroxy-5a,9-dimethyl-3-((4-o-tolylpiperazin-1-yl)methyl)-3,3a,4,5,5a,6,7,8-octahydronaphtho[1,2-b]furan-2(9bH)-one hydrochloride;

(5aR,9bS)-3a-Hydroxy-3-((4-(2-methoxyphenyl)piperazin-1-yl)methyl)-5a,9-dimethyl-3,3a,4,5,5a,6,7,8-octahydronaphtho[1,2-b]furan-2(9bH)-one;

(5aR,9bS)-3-((4-(2-Chlorophenyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3a-Hydroxy-5a,9-dimethyl-3-((4-(pyridin-2-yl)piperazin-1-yl)methyl)-3,3a,4,5,5a,6,7,8-octahydronaphtho[1,2-b]furan-2(9bH)-one;

(5aS,9bS)-3a-Hydroxy-3-((4-(((5aR,9bS)-3a-hydroxy-5a,9-dimethyl-2-oxo-2,3,3a,4,5,5a,6,7,8,9b-decahydronaphtho[1,2-b]furan-3-yl)methyl)piperazin-1-yl)methyl)-5a,9-dimethyl-3,3a,4,5,5a,6,7,8-octahydronaphtho[1,2-b]furan-2(9bH)-one;

(5aS,9bR)-3a-Hydroxy-3-((((5aR,9bS)-3a-hydroxy-5a,9-dimethyl-2-oxo-2,3,3a,4,5,5a,6,7,8,9b-decahydronaphtho[1,2-b]furan-3-yl)methylamino)methyl)-5a,9-dimethyl-3,3a,4,5,5a,6,7,8-octahydronaphtho[1,2-b]furan-2(9bH)-one hydrochloride;

N-(((5aR,9bS)-3a-Hydroxy-5a,9-dimethyl-2-oxo-2,3,3a,4,5,5a,6,7,8,9b-decahydronaphtho[1,2-b]furan-3-yl)methyl)-N-(((5aS,9bR)-3a-hydroxy-5a,9-dimethyl-2-oxo-2,3,3a,4,5,5a,6,7,8,9b-decahydronaphtho[1,2-b]furan-3-yl)methyl)acetamide;

3-Ethyl-1-(((5aR,9bS)-3a-hydroxy-5a,9-dimethyl-2-oxo-2,3,3a,4,5,5a,6,7,8,9b-decahydronaphtho[1,2-b]furan-3-yl)methyl)-1-(((5aS,9bR)-3a-hydroxy-5a,9-dimethyl-2-oxo-2,3,3a,4,5,5a,6,7,8,9b-decahydronaphtho[1,2-b]furan-3-yl)methyl)thiourea;

Methyl 2-(((5aR,9bS)-3a-hydroxy-5a,9-dimethyl-2-oxo-2,3,3a,4,5,5a,6,7,8,9b-decahydro naphtho[1,2-b]furan-3-yl)methylamino)acetate;

(5aR,9bS)-3a-Hydroxy-5a,9-dimethyl-3-(((2R)-2,4,5-trihydroxy-6-(hydroxymethyl)tetrahydro-2H-pyran-3-ylamino)methyl)-3,3a,4,5,5a,6,7,8-octahydronaphtho[1,2-b]furan-2(9bH)-one;

(5aR,9bS)-3a-Hydroxy-3-(((2-hydroxy-2-(4-hydroxyphenyl)ethyl)(methyl)amino)methyl)-5a,9-dimethyl-3,3a,4,5,5a,6,7,8-octahydronaphtho[1,2-b]furan-2(9bH)-one;

(5aR,9bS)-3a-hydroxy-3-(((2-hydroxy-2-(3-hydroxyphenyl)ethyl)(methyl)amino)methyl)-5a,9-dimethyl-3,3a,4,5,5a,6,7,8-octahydronaphtho[1,2-b]furan-2(9bH)-one; and 4-(1-Acetoxy-2-((((5aR,9bS)-3a-hydroxy-5a,9-dimethyl-2-oxo-2,3,3a,4,5,5a,6,7,8,9b-decahydronaphtho[1,2-b]furan-3-yl)methyl)(methyl)amino)ethyl)phenyl acetate;

The representative compounds of the present invention are useful in the treatment of inflammatory disorders.

The compounds of the present invention also include all stereoisomeric forms and mixtures thereof and their pharmaceutically acceptable salts, solvates and polymorphs. Furthermore, all the compounds of the present invention are a subject of the present invention in the form of their prodrugs and derivatives.

According to another aspect of present invention, the tricyclic compounds of general formula 1 can be prepared in a number of ways using methods well known to the person skilled in the art. Examples of methods to prepare the present compounds are described below and illustrated in Schemes 1 to 6 but not limited thereto. It will be appreciated by persons skilled in the art that within certain of the processes described herein, the order of the synthetic steps employed may be varied and will depend inter alia on factors such as the nature of functional groups present in a particular substrate and the protecting group strategy (if any) to be adopted. Clearly, such factors will also influence the choice of reagent to be used in the synthetic steps.

The reagents, reactants and intermediates used in the following processes are either commercially available or can be prepared according to standard literature procedures known in the art. The starting compounds and the intermediates used for the synthesis of compounds of the present invention, are referred to with general symbols namely (A), (A 1), (A 2), (A 3), (B 1), (B 2), (C), (D), (E), (F), (G), (H), (I), (J), (K), (L), (M), (N), (O), (P), (Q), (R), (S 1), (S 2), (S 3).

Throughout the process description, the corresponding substituent groups in the various formulae representing starting compounds and intermediates have the same meanings as that for the compounds of formula 1 unless stated otherwise.

The processes used in various schemes of the present invention, are referred to with general symbols namely 1a, 1b, 1c, 1d, 1e, 2a, 2b, 2c, 2d, 3a, 3b, 3c, 3d, 3e, 3f, 4a, 4b, 5a, 5b, 5c, 6a, 6b, 6c, 6d.

Processes for the preparation of compounds of the present invention are set forth in the following schemes:

The compound 7α-hydroxyeudesm-4-en-6,12-olide, (which can be isolated from a plant such as *Sphaeranthus indicus*, as described in Example 1 Step 2), which is referred to hereinafter in the schemes as compound (A), and is used as starting material for all the processes described in the following Schemes 1 to 6.

Scheme 1

Process 1: Preparation of Compounds of Formula (A 2)

Step 1

Preparation of Compound of Formula (A 1)

The compound (A) is subjected to an epoxidation reaction (Reaction 1a) in presence of metachloroperbenzoic acid and a chlorinated solvent such as chloroform or dichloromethane resulting in the formation of compound of formula (A 1). The reaction mixture is kept at a temperature in the range of 0° C.-5° C. over a time period ranging from 48 hours to 60 hours.

Step 2

Preparation of Compounds of Formula (A 2)

The compound (A 1) on treatment with an amine (Reaction 1b) selected from unsubstituted and substituted pyrazole, imidazole, triazole, tetrazole, piperazine, piperidine, morpholine, thiomorpholine, optionally in presence of a base such as triethylamine, sodium carbonate, potassium carbonate results in formation of compounds of formula (A 2) (wherein $R_{12}$ is —$NR_{15}R_{16}$; $R_{15}$ and $R_{16}$ have same meanings as described herein above). The solvent used for this reaction is an alcohol such as methanol, ethanol or propanol, or any polar solvent. The reactions are carried out at a temperature in the range of 20° C. to 30° C. under stirring.

The reaction is carried over a time period ranging from 2 hours to 20 hours.

Scheme 1

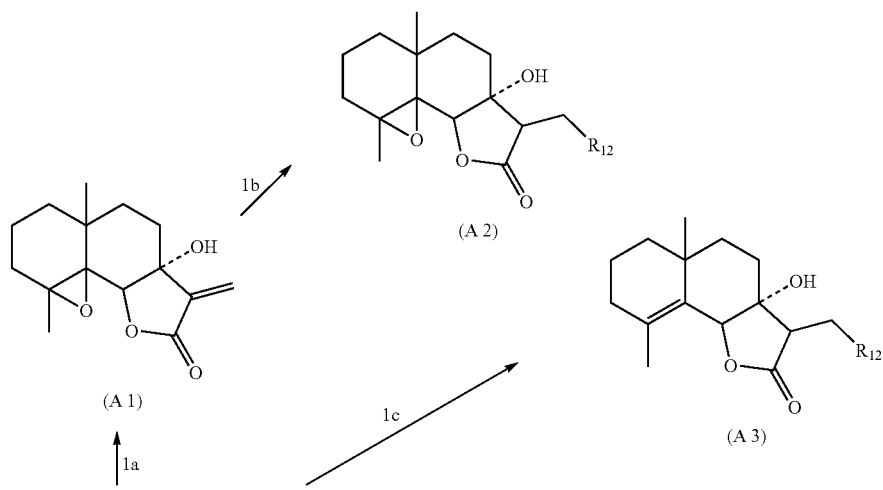

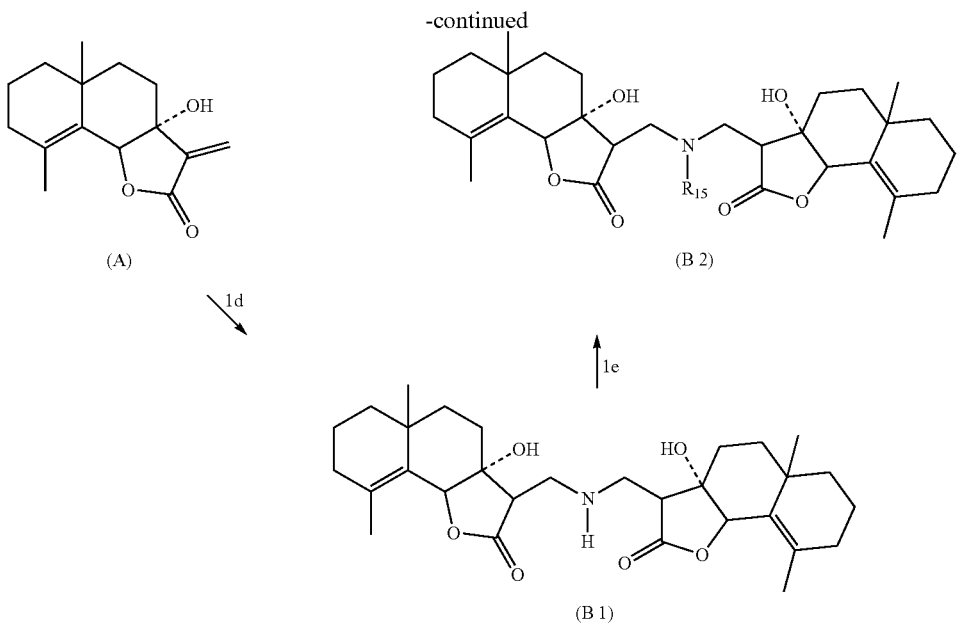

Process 2: Preparation of Compound of Formula (A 3)

The compound (A) is subjected to a reaction with an amine (Reaction 1c) selected from unsubstituted and substituted pyrazole, imidazole, triazole, tetrazole, piperazine, piperidine, morpholine, thiomorpholine, in presence of a base such as triethylamine, sodium carbonate or potassium carbonate in an alcoholic solvent such as methanol, ethanol or propanol. The reactions are carried out at a temperature in the range of 20° C. to 30° C. under stirring over a time period ranging from 2 hours to 20 hours. The reaction results in formation of compounds of general formula (A 3) (wherein $R_{12}$ is —$NR_{15}R_{16}$; $R_{15}$ and $R_{16}$ have same meanings as described herein above).

The compound (A) is subjected to a reaction with a sulfur compound (Reaction 1c) such as thiophenol or thioglycolic acid, in presence of a base such as triethylamine, sodium carbonate or potassium carbonate, in an alcoholic solvent such as methanol, ethanol or propanol. The reaction is out at a temperature in the range of 20° C. to 30° C. under stirring over a time period ranging from 3 hours to 10 hours. The reaction results in formation of compounds of formula (A 3) (wherein $R_{12}$ is —$S(O)_mR_{17}$; $R_{17}$ is selected from hydrogen, alkyl, cycloalkyl, aryl, and heterocyclyl; m is 0, 1 or 2).

Process 3: Preparation of Compounds of Formula (B 2)

Step 1

Preparation of Compound of Formula (B 1)

The compound (A) is subjected to a reaction with primary amine (Reaction 1d) such as ethanolic ammonia, in presence of an alcoholic solvent such as methanol, ethanol or propanol, resulting in formation of compound of formula (B 1). The reaction is carried out at a temperature in the range of 20° C. to 30° C. under stirring over a time period ranging from 3 hours to 10 hours.

Step 2

Preparation of Compounds of Formula (B 2)

The compound of formula (B 1) is reacted with reagents such as acetic anhydride or ethyl isothiocyanate or isocyanates or alkyl halides (Reaction 1e), in presence of a base such as pyridine, triethylamine, sodium carbonate or potassium carbonate, and a solvent such as acetonitrile, tetrahydrofuran or dioxane resulting in formation of compounds of formula (B 2) (wherein $R_{15}$ is selected from alkyl, —$C(O)R_{14}$, and —$C(S)$—$NHR_{14}$). The reaction is carried out at a temperature in the range of 20° C. to 30° C. under stirring over a time period ranging from 2 hours to 20 hours.

Scheme 2

Process 4: Preparation of Compounds of Formula (F)

Step 1

Preparation of Compound of Formula (C)

The compound (A) is reacted with selenium dioxide in ethanol or dioxane (Reaction 2a) resulting in the formation of compound of formula (C). The reaction is carried out over a temperature ranging from room temperature (25° C.) to reflux temperatures of the solvent used in the reaction. The time required for the reaction ranges from 3 hours to 10 hours.

Scheme 2

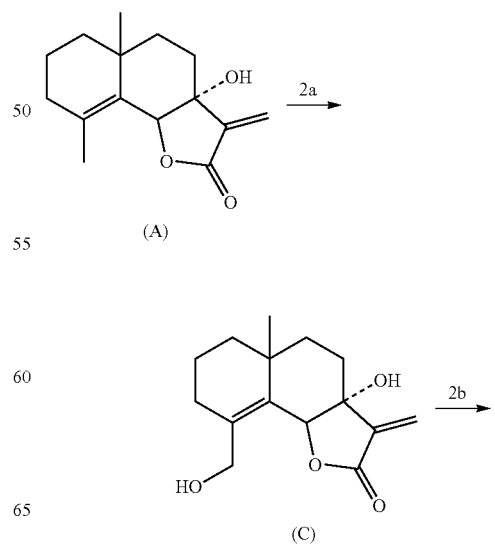

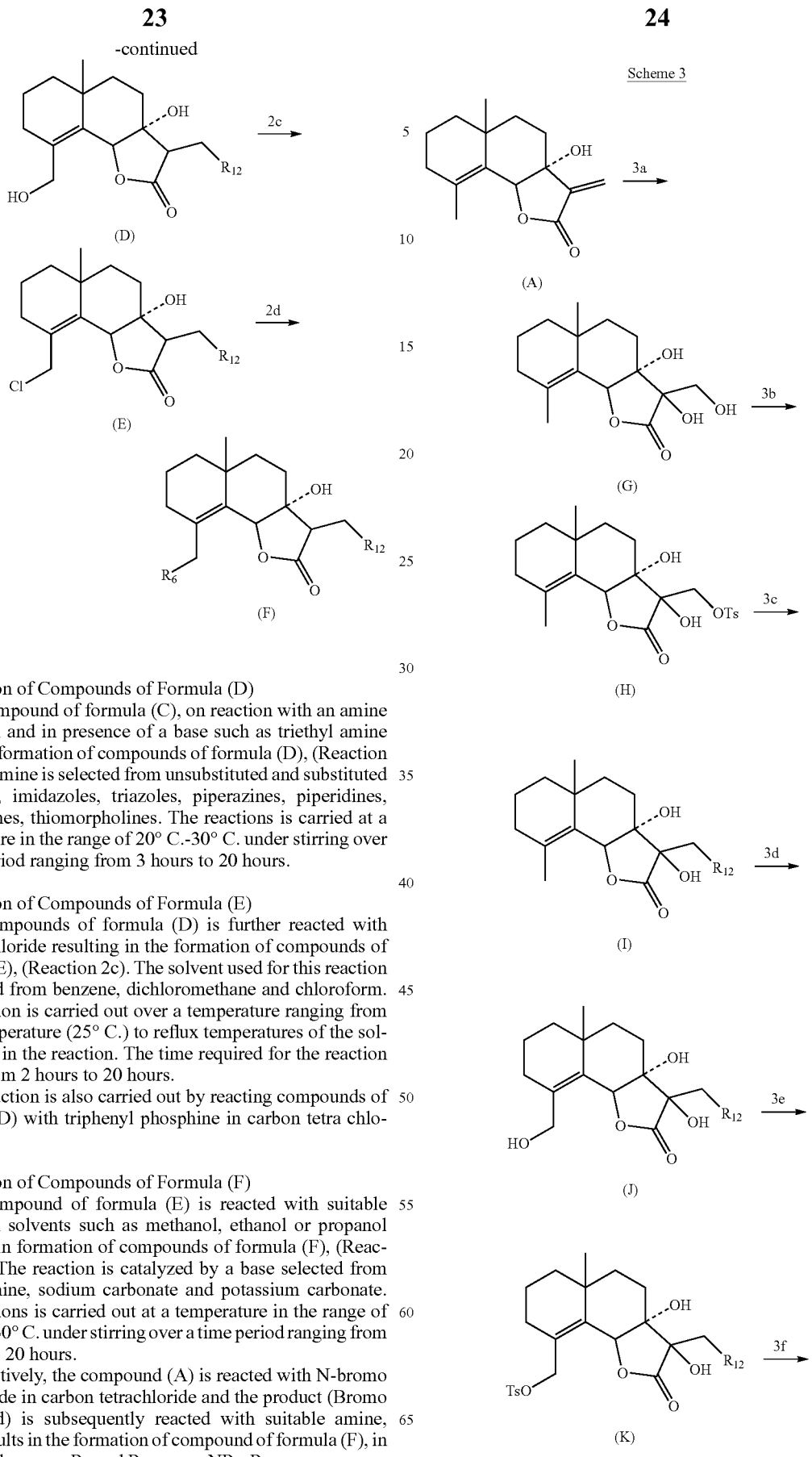

Scheme 3

Step 2
Preparation of Compounds of Formula (D)

The compound of formula (C), on reaction with an amine in ethanol and in presence of a base such as triethyl amine results in formation of compounds of formula (D), (Reaction 2b). The amine is selected from unsubstituted and substituted pyrazoles, imidazoles, triazoles, piperazines, piperidines, morpholines, thiomorpholines. The reactions is carried at a temperature in the range of 20° C.-30° C. under stirring over a time period ranging from 3 hours to 20 hours.

Step 3
Preparation of Compounds of Formula (E)

The compounds of formula (D) is further reacted with thionyl chloride resulting in the formation of compounds of formula (E), (Reaction 2c). The solvent used for this reaction is selected from benzene, dichloromethane and chloroform. The reaction is carried out over a temperature ranging from room temperature (25° C.) to reflux temperatures of the solvent used in the reaction. The time required for the reaction ranges from 2 hours to 20 hours.

The reaction is also carried out by reacting compounds of formula (D) with triphenyl phosphine in carbon tetra chloride.

Step 4
Preparation of Compounds of Formula (F)

The compound of formula (E) is reacted with suitable amines in solvents such as methanol, ethanol or propanol resulting in formation of compounds of formula (F), (Reaction 2d). The reaction is catalyzed by a base selected from triethylamine, sodium carbonate and potassium carbonate. The reactions is carried out at a temperature in the range of 20° C. to 30° C. under stirring over a time period ranging from 3 hours to 20 hours.

Alternatively, the compound (A) is reacted with N-bromo succinimide in carbon tetrachloride and the product (Bromo compound) is subsequently reacted with suitable amine, which results in the formation of compound of formula (F), in which both groups $R_6$ and $R_{12}$ are —$NR_{15}R_{16}$.

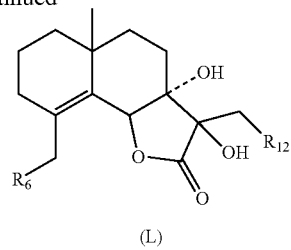

(L)

Scheme 3
Process 5: Preparation of Compounds of Formula (L)
Step 1
Preparation of Compound of Formula (G)

The compound (A) is reacted with N-methylmorpholine-N-oxide (NMO) and osmium tetraoxide in presence of a solvent such as acetone resulting in the formation of compound of formula (G), (Reaction 3a). The reaction is carried out at a temperature in the range of 20° C. to 30° C. under stirring over a time period ranging from 3 hours to 20 hours.

Step 2
Preparation of Compound of Formula (H)

The compound of formula (G) is reacted with tosyl chloride in presence of a solvent such as dichloromethane, resulting in formation of compound of formula (H), (Reaction 3b). The reaction is catalyzed by a base such as pyridine and 4-(Dimethylamino)pyridine (DMAP). The reaction is carried out at a temperature in the range of 20° C. to 30° C. under stirring over a time period ranging from 20 hours to 80 hours.

Step 3
Preparation of Compounds of Formula (I)

The compound of formula (H) is reacted with an amine selected from unsubstituted and substituted pyrazole, imidazole, triazole, piperazine, piperidine, morpholine, and thiomorpholine resulting in formation of compounds of formula (I), (Reaction 3c). The reaction is catalyzed by a base such as triethylamine. The reaction is carried out at a temperature in the range of 20° C. to 30° C. under stirring over a time period ranging from 3 hours to 20 hours.

Step 4
Preparation of Compounds of Formula (J)

The compound of formula (I) is treated with selenium dioxide in a solvent such as benzene, toluene or dioxane resulting in formation of compounds of formula (J), (Reaction 3d). The reaction is carried out over a temperature ranging from room temperature (25° C.) to reflux temperatures of the solvent used in the reaction. The time required for the reaction ranges from 3 hours to 10 hours.

Step 5
Preparation of Compounds of Formula (K)

The compound of formula (J) is reacted with tosyl chloride in presence of a solvent such as dichloromethane or chloroform or benzene, resulting in formation of compounds of formula (K), (Reaction 3e). The reaction is carried out at a temperature ranging from 20° C. to 30° C. under stirring over a time period ranging from 3 hours to 20 hours.

Step 6
Preparation of Compounds of Formula (L)

The compound of formula (K) is reacted with an amine selected from unsubstituted and substituted pyrazole, imidazole, triazole, piperazine, piperidine, morpholine and thiomorpholine, resulting in formation of compounds of formula (L), (Reaction 3f). The reaction is carried out at suitable temperatures ranging from 20° C. to 30° C. under stirring over a time period ranging from 3 hours to 20 hours.

Scheme 4

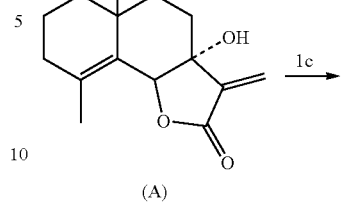

(A)

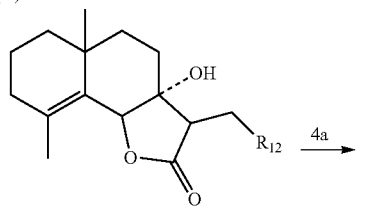

(A 3)

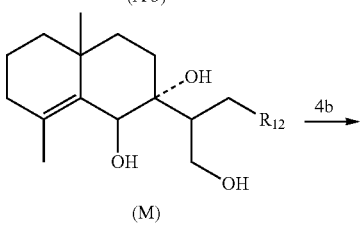

(M)

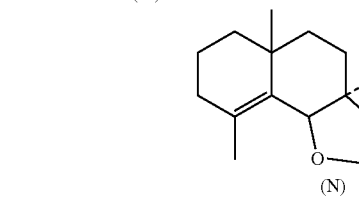

(N)

Scheme 4
Process 6: Preparation of Compounds of Formula (N)
Step 1
Preparation of Compounds of Formula (A 3)

Compound (A) is reacted with an amine (Reaction 1c) selected from substituted and unsubstituted imidazole, triazole, piperazine, piperidine, morpholine, thiomorpholine and other substituted heterocycles, in presence of a base such as triethylamine, sodium carbonate, potassium carbonate, in an alcoholic solvent such as methanol, ethanol or propanol, resulting in the formation of compounds of formula (A 3) (wherein $R_{12}$ is $-NR_{15}R_{16}$). The reaction is carried out at a temperature in the range of 20° C. to 30° C. under stirring over a time period ranging from 3 hours to 20 hours.

Step 2
Preparation of Compounds of Formula (M)

The compound of formula (A 3) is reacted with lithium aluminium hydride (LAH) in presence of a solvent such as tetrahydrofuran or ether, resulting in the formation of compounds of formula (M), (Reaction 4a). The reaction is carried out over a temperature ranging from room temperature (25° C.) to reflux temperatures of the solvent used in the reaction. The time required for the reaction ranges from 3 hours to 10 hours.

Step 3
Preparation of Compounds of Formula (N)

Compound of formula (M) is reacted with methane sulphonyl chloride in presence of a base such as pyridine resulting in the formation of compounds of formula (N), (Reaction 4b).

The reaction is carried out over temperature ranging from room temperature (25° C.) to reflux temperatures of the solvent used in the reaction. The time required for the reaction ranges from 15 hours to 30 hours.

Scheme 5

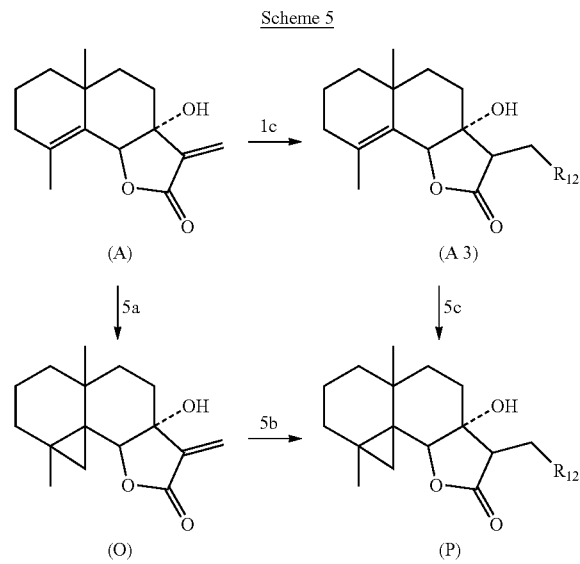

Scheme 5
Process 7: Preparation of Compounds of Formula (P)
Step 1
The compound (A) is treated with Zn (Cu) in presence of a solvent such as dichloromethane or diiodomethane or under Simmons-Smith reaction (Simmons-Smith Methylenation) conditions resulting in the formation of compound of formula (O), (Reaction 5a).
Step 2
Compound of formula (O) is reacted with an amine (Reaction 5b) selected from substituted and unsubstituted imidazole, triazole, piperazine. piperidine, morpholine, thiomorpholine, in presence of a base such as triethylamine, sodium carbonate, potassium carbonate, in an alcoholic solvent such as methanol, ethanol or propanol resulting in the formation of compounds of formula (P) (wherein $R_{12}$ is —$NR_{15}R_{16}$). The reaction is carried out at a temperature in the range of 20° C. to 30° C. under stirring over time period ranging from 3 hours to 20 hours.

The compounds of formula (P) can also be obtained by the following alternative route.
Step 1
Compound (A) is reacted with an amine (Reaction 1c) selected from substituted and unsubstituted imidazole, triazole, piperazine, piperidine, morpholine, thiomorpholine in presence of a base such as triethylamine, sodium carbonate, potassium carbonate, in an alcoholic solvent such as methanol, ethanol or propanol resulting in the formation of compounds of formula (A 3) (wherein $R_{12}$ is —$NR_{15}R_{16}$). The reaction is carried out at a temperature in the range of 20° C. to 30° C. under stirring over time period ranging from 3 hours to 20 hours.
Step 2
Preparation of Compounds of Formula (P);
The compound of formula (A 3) is treated with Zn (Cu) in presence of a solvent such as dichloromethane or diiodomethane or under Simmons-Smith reaction (Simmons-Smith Methylenation) conditions to result in formation of compounds of formula (P) (Reaction 5c).
Scheme 6
Process 8: Preparation of Compounds of Formula (Q)
Compound (A) is reacted with Lawesson's reagent in presence of an inert solvent such as toluene, tetrahydrofuran or dioxane resulting in formation of the compound of formula (Q), (Reaction 6a). The reaction is carried out over a temperature ranging from room temperature to reflux temperatures of the solvent used in the reaction. The time required for the reaction ranges from 2 hours to 10 hours.
Process 9: Preparation of Compounds of Formula (S 1), (S 2) and (S 3)
Step 1
Compound (A) is reacted with an amine (Reaction 1c) selected from substituted and unsubstituted imidazole, triazole, piperazine, piperidine, morpholine, thiomorpholine in presence of a base such as triethylamine, sodium carbonate, potassium carbonate, in an alcoholic solvent such as methanol, ethanol or propanol, resulting in the formation of compounds of formula (A 3) (wherein $R_{12}$ is —$NR_{15}R_{16}$). The reaction is carried out at a temperature in the range of 20° C. to 30° C. under stirring over time period ranging from 3 hours to 20 hours.

Scheme 6

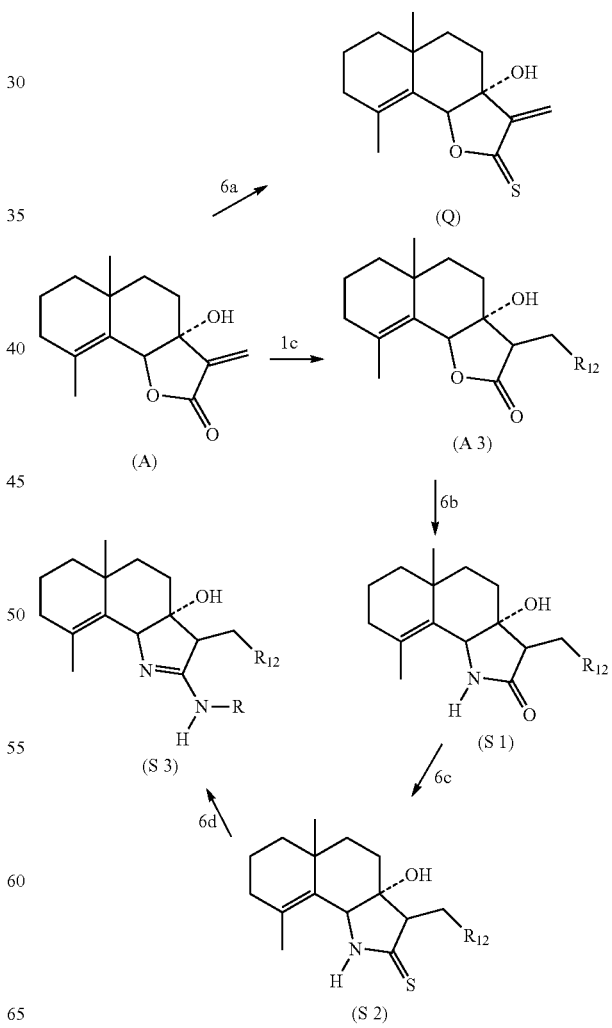

Step 2

The compound of formula (A 3) is reacted with ethanolic ammonia in a steel bomb, resulting in the formation of compound of formula (S 1), (Reaction 6b). The reaction is carried out at a temperature in the range of 70° C. to 90° C.

Step 3

The compound of formula (S 1) is treated with Lawesson's reagent in presence of a solvent such as toluene, tetrahydrofuran or dioxane, resulting in the formation of compound of formula (S 2), (Reaction 6c). The reaction is carried out at a temperature ranging from room temperature to reflux temperatures of the solvent used in the reaction. The time required for the reaction ranges from 2 hours to 10 hours.

Alternately, the compound of formula (S 1) is reacted with phosphorous pentasulphide in toluene, resulting in the formation of compound of formula (S 2), (Reaction 6c). The reaction is carried out over a temperature ranging from room temperature (25° C.) to reflux temperatures of the solvent used in the reaction. The time required for the reaction ranges from 2 hours to 10 hours.

Step 4

The compound of formula (S 2) is treated with an alkyl halide such as methyl bromide, methyl iodide or ethyl iodide in a solvent such as ethanol resulting in formation of corresponding quaternary S-alkyl salt. The reaction is carried out at a temperature ranging from 20° C. to 30° C. under stirring over time period ranging from 3 hours to 15 hours. The quaternary S-alkyl salt is reacted with an amine in a solvent such as ethanol, resulting in the formation of compound of formula (S 3), (Reaction 6d). The reaction is carried out at a temperature ranging from room temperature to reflux temperatures of the solvent used in the reaction, under stirring over time period ranging from 2 hours to 10 hours.

It will be appreciated by those skilled in the art that the compounds of the present invention can also be utilized in the form of their pharmaceutically acceptable salts or solvates thereof. The pharmaceutically acceptable salts of the compounds of the present invention are in particular salts which are non-toxic, or which is used physiologically.

With respect to the compounds of general formula 1 the present invention also includes all stereoisomeric forms and mixtures thereof in all ratios and their pharmaceutically acceptable salts.

The compounds of the present invention can subsequently be converted into their organic or inorganic salts, like the methane sulfonic acid salts, by treatment with methane sulfonic acid in a dry solvent like ethyl acetate, dioxane, diethyl ether, methanol, ethanol or any other suitable solvent and processed in a manner known to one skilled in the art.

Thus, when the compounds of the present invention represented by the general formula 1 contain one or more basic groups, i.e. groups which can be protonated, they can form an addition salt with a suitable inorganic or organic acid. Examples of suitable inorganic acids include: boric acid, perchloric acid, hydrochloric acid, hydrobromic acid, hydrofluoric acid, sulfuric acid, sulfamic acid, phosphoric acid, nitric acid and other inorganic acids known to the person skilled in the art. Examples of suitable organic acids include: acetic acid, propionic acid, succinic acid, glycolic acid, stearic acid, lactic acid, malic acid, tartaric acid, citric acid, ascorbic acid, pamoic acid, maleic acid, hydroxymaleic acid, fumaric acid, phenylacetic acid, glutamic acid, benzoic acid, salicylic acid, sulfanilic acid, 2-acetoxybenzoic acid, toluenesulfonic acid, methanesulfonic acid, benzenesulfonic acid, ethane disulfonic acid, oxalic acid, isethionic acid, ketoglutaric acid, glycerophosphoric acid, aspartic acid, picric acid, lauric acid, palmitic acid, cholic acid, pantothenic acid, alginic acid, naphthoic acid, mandelic acid, tannic acid, camphoric acid and other organic acids known to the person skilled in the art.

The present invention furthermore includes solvates of the compounds of general formula 1, for example hydrates and the solvates formed with other solvents of crystallization, such as alcohols, ethers, ethyl acetate, dioxane, dimethylformamide or a lower alkyl ketone such as acetone, or mixtures thereof.

The present invention furthermore includes polymorphs of the compounds of general formula 1. Polymorphs may be obtained by heating or melting the compounds of present invention followed by gradual or fast cooling. The presence of polymorphs may be determined by IR spectroscopy, solid probe NMR spectroscopy, differential scanning calorimetry, powder X-ray diffraction or such other techniques.

The present invention also includes prodrugs of the compounds of general formula 1, for example esters, amides and other physiologically acceptable derivatives.

The expression "prodrug" refers to compounds that are drug precursors, which following administration, release the drug in vivo via a chemical or physiological process e.g., a prodrug on being brought to the physiological pH or through an enzyme action is converted to the desired drug form.

The compounds of the present invention are TNF-α inhibitors and find use in therapies for disorders associated with abnormal TNF-α activity, including: inflammatory bowel disease, inflammation, rheumatoid arthritis, juvenile rheumatoid arthritis, psoriatic arthritis, osteoarthritis, refractory rheumatoid arthritis, chronic non-rheumatoid arthritis, osteoporosis/bone resorption, Crohn's disease, septic shock, endotoxic shock, atherosclerosis, ischemia-reperfusion injury, coronary heart disease, vasculitis, amyloidosis, multiple sclerosis, sepsis, chronic recurrent uveitis, hepatitis C virus infection, malaria, ulcerative colitis, cachexia, psoriasis, plasmocytoma, endometriosis, Behcet's disease, Wegener's granulomatosis, meningitis, AIDS, HIV infection, autoimmune disease, immune deficiency, common variable immunodeficiency (CVID), chronic graft-versus-host disease, trauma and transplant rejection, adult respiratory distress syndrome, pulmonary fibrosis, recurrent ovarian cancer, lymphoproliferative disease, refractory multiple myeloma, myeloproliferative disorder, diabetes, juvenile diabetes, ankylosing spondylitis, skin delayed-type hypersensitivity disorders, Alzheimer's disease, systemic lupus erythematosus, and allergic asthma.

In certain embodiments, the compounds of the present invention are interleukin (IL-1β, IL-6, IL-8) inhibitors and find use in therapies for disorders associated with abnormal interleukin (IL-1β, IL-6, IL-8) activity, including: rheumatoid arthritis, osteoarthritis and other autoimmune conditions.

Representative compounds useful in the treatment of inflammatory disorders in accordance with the present invention include:

(5aR,9bS)-3a-Hydroxy-5a,9-dimethyl-3-(piperidin-1-ylmethyl)-3,3a,4,5,5a,6,7,8-octahydronaphtho[1,2-b]furan-2 (9bH)-one; and (5aR,9bS)-3a-Hydroxy-5a,9-dimethyl-3-(morpholinomethyl)-3,3a,4,5,5a,6,7,8-octahydronaphtho[1,2-b]furan-2 (9bH)-one.

According to an embodiment, the present invention provides a method for the treatment of inflammatory disorders, such as those caused by elevated levels of Tumor Necrosis Factor-alpha (TNF-α), and interleukins (IL-1β, IL-6, IL-8), including administering to a mammal in need thereof a therapeutically effective amount of a compound of formula 1.

According to another aspect of the present invention, there are provided pharmaceutical compositions including therapeutically effective amount of compounds of general formula 1 as active ingredient and pharmaceutically acceptable carrier, useful in the treatment of inflammatory disorders, such as those caused by elevated levels of proinflammatory cytokines such as Tumor Necrosis Factor-alpha (TNF-α and/or interleukins (IL-1 β, IL-6, IL-8).

By "pharmaceutically acceptable" is meant that the carrier, diluent, excipients, and/or salt must be compatible with the other ingredients of the formulation, and not deleterious to the recipient thereof.

The term "pharmaceutically acceptable carrier" as used herein means a non-toxic, inert, solid, semi-solid, diluent, encapsulating material or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose and cellulose acetate; malt; gelatin; talc; as well as other non-toxic compatible lubricants such as sodium lauryl sulfate and magnesium stearate, as well as coloring agents, releasing agents, coating agents, sweetening, flavoring and perfuming agents; preservatives and antioxidants can also be present in the composition, according to the judgment of the formulator.

The term, "therapeutically effective amount" as used herein means an amount of compound or composition (e.g. compound of formula 1) sufficient to significantly induce a positive modification in the condition to be regulated or treated, but low enough to avoid side effects if any (at a reasonable benefit/risk ratio), within the scope of sound medical judgment. The therapeutically effective amount of the compound or composition will vary with the particular condition being treated, the age and physical condition of the end user, the severity of the condition being treated/prevented, the duration of the treatment, the nature of concurrent therapy, the specific compound or composition employed, the particular pharmaceutically acceptable carrier utilized, and like factors. As used herein, all percentages are by weight unless otherwise specified.

According to another aspect of present invention, there are provided methods of treatment of inflammatory disorders, such as those caused by elevated levels of proinflammatory cytokines such as Tumor Necrosis Factor-alpha (TNF-α) and/or interleukins (IL-1β, IL-6, IL-8) using these compositions as described herein above.

The term "inflammatory disorder" as used herein refers to a disease or a condition characterized by chronic inflammation including but not limited to rheumatoid arthritis, osteoarthritis, juvenile rheumatoid arthritis, psoriatic arthritis, refractory rheumatoid arthritis, chronic non-rheumatoid arthritis, osteoporosis/bone resorption, coronary heart disease, atherosclerosis, vasculitis, ulcerative colitis, psoriasis, Crohn's disease, adult respiratory distress syndrome, delayed-type hypersensitivity in skin disorders, septic shock syndrome, inflammatory bowel disease and the like.

The term "abnormal" as used herein and in the appended claims in the context of proinflammatory cytokines Tumor Necrosis Factor-alpha (TNF-α) and/or interleukins (IL-1β, IL-6, IL-8) refers to elevated or increased levels of the proinflammatory cytokines.

According to another aspect of present invention there are provided methods for manufacture of medicaments including compounds of general formula 1, which are useful for the treatment of inflammatory disorders caused by elevated levels of proinflammatory cytokines such as Tumor Necrosis Factor-alpha (TNF-α and/or interleukins (IL-1β, IL-6, IL-8).

The pharmaceutical compositions according to the present invention are prepared in a manner known per se and familiar to one skilled in the art. Pharmaceutically acceptable inert inorganic and/or organic carriers and/or additives can be used in addition to the compound(s) of the general formula 1, and/or its physiologically tolerable salts and/or its prodrugs. For the production of pills, tablets, coated tablets and hard gelatin capsules it is possible to use, for example, lactose, corn starch or derivatives thereof, gum arabic, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, physiological sodium chloride solution or alcohols, for example, ethanol, propanol or glycerol, sugar solutions, such as glucose solutions or mannitol solutions, or a mixture of the various solvents which have been mentioned.

In addition to the active ingredients of the compound of general formula 1, and/or its physiologically acceptable salts and/or prodrugs and carrier substances, the pharmaceutical compositions can contain additives such as, for example, fillers, antioxidants, dispersants, emulsifiers, defoamers, flavors, preservatives, solubilizers or colorants. The pharmaceutical compositions of the present invention can also contain two or more compounds of the general formula 1 and/or its physiologically tolerable salts and/or their prodrugs. Furthermore, in addition to at least one compound of the general formula 1, and/or its physiologically tolerable salts and/or its prodrugs, the pharmaceutical compositions can also contain one or more other therapeutically or prophylactically active ingredients.

The pharmaceutical compositions normally contain about 1 to 99%, for example, about 5 to 70%, or about 10 to about 30% by weight of the compounds of general formula 1 or their physiologically tolerable salts or their prodrugs. The amount of the active ingredient of general formula 1, and/or its physiologically tolerable salts and/or its prodrugs in the pharmaceutical compositions can, for example, be from about 5 to 500 mg. The dose of the compounds of this invention, which is to be administered, can cover a wide range. The dose to be administered daily is to be selected to suit the desired effect. A dosage of about 0.001 to 100 mg/kg/day of the compound of general formula 1 or a prodrug thereof may be administered per day. If required, higher or lower daily doses can also be administered.

Actual dosage levels of the active ingredients in the pharmaceutical compositions of this invention can be varied so as to obtain an amount of the active ingredient, which is effective to achieve the desired therapeutic response for a particular patient, composition, and mode of administration without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular compounds employed, the age, sex, weight, condition, general health and prior medical history of the patient being treated, and like factors well known in the medical arts. The pharmaceutical compositions according to the present invention can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or transdermal patches, or in other ways, for example in the form of aerosols or nasal sprays.

It is understood that modifications that do not substantially affect the activity of the various embodiments of this invention are included within the invention disclosed herein. Accordingly, the following examples are intended to illustrate but not to limit the present invention.

The invention is explained in detail in the examples given below and should not be construed to limit the scope of the invention:

EXAMPLES

List of Abbreviations

TEA: Triethylamine
DCM: Dichloromethane
DMAP: 4-(Dimethylamino)pyridine
DMSO: Dimethyl sulphoxide
DMF: Dimethylformamide
DIBAL: Diisobutylaluminium hydride
FBS: Fetal Bovine Serum
LAH: Lithium Aluminum Hydride
NaClO: Sodium hypochlorite
NaClO$_2$: Sodium chlorite
TEMPO: 2,2,6,6-tetramethyl-1-piperidine-N-oxyl
MTS: (3-(4,5-Dimethylthiazol-2-yl)-5-(3-carboxymethoxyphenyl)-2-(4-sulfonyl)-2H-tetrazolium)
RPMI: Roswell Park Memorial Institute
atm: atmosphere

Example 1

Isolation of 7α-hydroxyeudesm-4-en-6,12-olide from the Plant Extract of *Sphaeranthus indicus* and Stereochemistry Assignment for the Compound Step 1
Preparation of Petroleum Ether Extract of *Sphaeranthus Indicus*

The flowering and fruiting heads of *Sphaeranthus indicus* were collected from Krishna District, Andhra Pradesh, India.

Dried flowering and fruiting heads of *Sphaeranthus indicus* (1 Kg) were pulverized. The powdered material was extracted using petroleum ether (6 L) by stirring at 40° C. for 6 hours. The extract was filtered using vacuum. This extraction process was repeated two more times. The extracts were combined and concentrated.

Yield: 35 g (3.5% w/w).
Step 2
Isolation and Characterization of 7α-hydroxyeudesm-4-en-6,12-olide The petroleum ether extract (10 g) as obtained in step 1, was purified by column chromatography (silica gel, ethyl acetate in petroleum ether). The crude product (4.5 g) was purified further by crystallization using ethyl acetate/petroleum ether.

Yield: 1.2 g; mp: 63-65° C.; IR cm$^{-1}$ (KBr): 939, 1190, 1291, 1749, 2937, 3545;
1H NMR (CDCl$_3$, 300 MHz): δ 1.09 (s, 3H), 1.36-1.55 (m, 4H), 1.65-1.70 (m, 3H), 1.79-1.81 (m, 4H), 1.94-2.07 (m, 1H), 2.09-2.19 (m, 2H), 5.03 (s, 1H), 5.82 (s, 1H), 6.26 (s, 1H); MS: m/e (ES) 247.1 (M−1);

Compound was characterized as 7α-hydroxyeudesm-4-en-6,12-olide by comparing the melting point and spectral data. (Indian Journal of Chemistry, Vol. 25B, 233-238, (1986));

This compound obtained in Example 1 step 2 is referred to hereinafter as compound of example 1
Step 3
Stereochemistry Assignment of Compound of Step 2

The stereochemistry of this compound was further established by comparing melting point and spectral data of epoxide of compound of example 1 and epoxide of 7α-hydroxyeudesm-4-en-6,12-olide as reported in the reference. (J. Chem. Soc. Perkin Trans. 1:(2), 157-160, (1988).)
Preparation of Epoxide of Product Obtained in Step 2

The solution of m-chloroperbenzoic acid (9.3 g, 53.9 mmol) in dichloromethane (160 mL) was added dropwise to a solution of compound of example 1 (as obtained in step 2), (3.4 g, 13.70 mmol) in dichloromethane (350 mL) at 0° C. Reaction mixture was kept at 0° C. for 48 hours. The reaction mixture was washed with sodium bicarbonate and with water. Dichloromethane layer was dried over sodium sulfate. The solvent was removed by concentration and the epoxide was obtained by trituration with cold petroleum ether.

Yield: 1.36 g (37.7%); mp: 155-158° C.; $^1$H NMR (CDCl$_3$, 300 MHz): δ 1.11 (s, 3H), 1.26-1.33 (m, 1H), 1.37 (s, 3H), 1.59-1.76 (m, 4H), 1.77-1.93 (m, 4H), 1.95-2.1 (m, 2H), 3.9 (s, 1H), 5.83 (s, 1H), 6.24 (s, 1H);
MS: m/e 265 (M+1).

The melting point of compound of step 3 (epoxide): 155-158° C. (observed);

The melting point of 4α, 5α-epoxy-7α-hydroxyeudesm-4-en-6,12-olide: 155-157° C. (reported in literature); (J. Chem. Soc. Perkin Trans. 1, 157-160, (1988)).

This establishes the structure and stereochemistry of compound of step 2 as 7α-hydroxyeudesm-4-en-6,12-olide.

Example 2

(5aR,9bS)-3,3a-Dihydroxy-3-(hydroxymethyl)-5a,9-dimethyl-3,3a,4,5,5a,6,7,8-octahydronaphtho[1,2-b]furan-2(9bH)-one N-Methylmorpholine-N-oxide (320 mg, 2.74 mmol) and osmium tetroxide (OsO$_4$) (3.1 mg, 0.012 mmol) were added to the solution of compound of example 1 (309 mg, 1.24 mmol) dissolved in acetone (3 mL) and water (6 mL). Reaction mixture was stirred for 2 hours. Reaction mixture was extracted using ethyl acetate (3×100 mL). The ethyl acetate layer was washed with saturated sodium bisulfate solution. The ethyl acetate layer was washed with water and brine and was dried over sodium sulfate. The solvent was removed and crude product was purified by column chromatography (silica gel, 50% ethyl acetate in petroleum ether) to obtain the title compound.

Yield: 240 mg (68%); $^1$H NMR (CDCl$_3$, 300 MHz): δ 0.92 (s, 3H), 1.24-1.58 (m, 7H), 1.68 (s, 3H), 1.73 (m, 1H), 2.02 (m, 2H), 3.58 (d, 2H,), 4.67 (t, 1H,), 4.90 (1H, s), 5.07 (s, 1H), 5.73 (s, 1H); MS: m/e ESI (+) 304.98 (M+Na$^+$).

Example 3

((5aR,9bS)-3,3a-Dihydroxy-5a,9-dimethyl-2-oxo-2, 3,3a,4,5,5a,6,7,8,9b-decahydronaphtho[1,2-b]furan-3-yl)methyl acetate Compound of example 2 (150 mg, 0.531 mmole) was dissolved in dichloromethane (10 mL). Acetic anhydride (54.25 mg, 0.531 mmole), pyridine (84 mg, 1.062 mmole) and 4-(dimethylamino)-pyridine (DMAP) (2 mg) were added to this solution and reaction mixture was stirred for 30 minutes. Reaction mixture was extracted with dichloromethane (3×100 mL). The dichloromethane layer was washed with water and brine and was dried over sodium sulfate. The solvent was removed and crude product was purified by crystallization using ethyl acetate/petroleum ether to obtain the title compound.

Yield: 120 mg (69.62%); $^1$H NMR (CDCl$_3$, 300 MHz): δ 0.96 (s, 3H), 1.28-1.40 (m, 3H), 1.52-1.59 (m, 3H), 1.66-1.74 (m, 4H), 1.76-1.80 (m, 1H), 1.96-2.00 (m, 1H), 2.04 (s, 3H), 2.08-2.11 (m, 1H), 4.23 (d, 1H,), 4.39 (d, 1H,), 5.15 (s, 1H); MS: m/e 323 (M−1).

Example 4

((5aR,9bS)-3,3a-dihydroxy-5a,9-dimethyl-2-oxo-2,3, 3a,4,5,5a,6,7,8,9b-decahydronaphtho[1,2-b]furan-3-yl)methyl 2-(4-benzylpiperazin-1-yl)acetate Step 1
((5aR,9bS)-3,3a-dihydroxy-5a,9-dimethyl-2-oxo-2,3,3a,4,5, 5a,6,7,8,9b-decahydronaphtho[1,2-b]furan-3-yl)methyl 2-chloroacetate Compound of example 2 (300 mg, 1.06 mmol) was dissolved in DCM (10 mL). To it was added chloroacetyl chloride (132.16 mg, 1.17 mmol), TEA (130.21 mg, 1.28 mmol) and was stirred at room temperature (25° C.) for 4 hours. Reaction mixture was diluted with cold water and was extracted with DCM (3×50 mL). The organic layer was dried on sodium sulphate, concentrated and purified by silica gel column chromatography (silica gel, 5-10% ethyl acetate in petroleum ether) to obtain the compound of step 1.

Yield: 300 mg (78.94%); $^1$HNMR (CDCl$_3$, 300 MHz): δ 1.04 (s, 3H), 1.25-1.67 (m, 8H), 1.79 (s, 3H), 2.03-2.16 (m, 3H), 4.16 (s, 2H), 4.34 (d, 1H), 4.74 (d, 1H), 5.25 (s, 1H).
Step 2
A solution of compound of step 1 (150 mg, 0.41 mmol) and N-benzyl piperazine (73.74 mg, 0.41 mmol) in DCM (10 mL) & TEA (84.43 mg, 0.83 mmol) was stirred at room temperature (25° C.) for 24 hours. Water was added to the reaction mixture and was extracted by DCM (3×50 mL), dried over sodium sulphate and was concentrated to obtain the title compound.

Yield: 100 mg (47.92%); $^1$H NMR (CDCl$_3$, 300 MHz): δ 1.2 (s, 3H), 1.30-1.49 (m, 4H), 1.63-1.68 (m, 4H), 1.80 (s, 3H), 2.05-2.12 (m, 2H), 2.54 (bs, 4H), 2.67 (bs, 4H), 3.30 (s, 2H), 3.54 (s, 2H), 4.30 (d, 1H), 4.69 (d, 1H), 5.26 (s, 1H), 7.28-7.33 (m, 5H); MS m/e: 499.28 (M+1).

Example 5

((5aR,9bS)-3,3a-Dihydroxy-5a,9-dimethyl-2-oxo-2, 3,3a,4,5,5a,6,7,8,9b-decahydronaphtho[1,2-b]furan-3-yl)methyl 4-methylbenzenesulfonate Compound of example 2 (126.6 mg, 0.449 mmol) was dissolved in dichloromethane (5 mL). Tosyl chloride (427.9 mg, 2.24 mmole), pyridine (355.05 mg, 4.48 mmole) and DMAP (2 mg) were added to this solution and reaction mixture was stirred for 72 hours. Reaction mixture was extracted with dichloromethane (5 mL). Dichloromethane was removed and crude product was purified by column chromatography (silica gel, 5-10% ethyl acetate in petroleum ether) to obtain the title compound.

Yield: 160 mg (82%); $^1$H NMR (CDCl$_3$, 300 MHz): δ 1.05 (s, 3H), 1.37-1.53 (m, 4H), 1.58-1.78 (m, 4H), 1.79 (s, 3H), 2.03-2.19 (m, 2H), 2.49 (s, 3H), 4.25-4.35 (q, 2H), 5.25 (s, 1H), 7.40 (d, 2H), 7.84 (d, 2H); MS: m/e 437 (M+1).

Example 6

(5aR,9bS)-3-(Azidomethyl)-3,3a-dihydroxy-5a,9-dimethyl-3,3a,4,5,5a,6,7,8-octahydronaphtho[1,2-b]furan-2(9bH)-one Sodium azide (32.5 mg, 0.5 mmol) was added to the solution of compound of example 5 (218 mg, 0.5 mmol) in dimethylformamide (DMF) (2 mL) and stirred at 50° C. under nitrogen atmosphere for 24 hours. The reaction mixture was concentrated, dried and was dissolved in water (25 mL) and was extracted with ethyl acetate (3×50 mL). The ethyl acetate layer was washed with water and brine and was dried over sodium sulfate. Solvent was removed and crude product was washed with petroleum ether, to obtain the title compound.

Yield: 112 mg (72.9%); $^1$H NMR (CDCl$_3$, 300 MHz): δ 1.05 (s, 3H), 1.27-1.67 (m, 6H), 1.81-1.91 (m, 5H), 2.05-2.24 (m, 3H), 3.53 (d, 1H), 3.85 (d, 1H), 5.25 (s, 1H); MS m/e: 306 (M−1)

Example 7

(5aR,9bS)-3,3a-Dihydroxy-5a,9-dimethyl-3-(piperidin-1-ylmethyl)-3,3a,4,5,5a,6,7,8-octahydronaphtho[1,2-b]furan-2(9bH)-one Piperidine (70.59 mg, 0.829 mmol) was added to compound of example 5 (180 mg, 0.412 mmol) dissolved in ethanol (5 mL) and reaction mixture was stirred for 24 hours. Saturated sodium bicarbonate solution was added, and reaction mixture was extracted with dichloromethane (3×50 mL). Dichloromethane layer was washed with water and brine and was dried over sodium sulfate. Solvent was removed and the crude product was purified by column chromatography (silica gel, 5-10% ethyl acetate in petroleum ether) to obtain the title compound.

Yield: 90 mg (62.5%); $^1$H NMR (DMSO-d6, 300 MHz): δ 0.85 (s, 3H), 1.15-1.21 (m, 2H), 1.25-1.34 (m, 3H), 1.37-1.37 (m, 2H), 1.39-1.50 (m, 6H), 1.58-1.60 (m, 1H), 1.63 (s, 3H), 1.92-2.04 (m, 2H), 2.42-2.48 (m, 3H), 2.54-2.59 (m, 3H), 5.1 (s, 1H); MS: m/e 350 (M+1);

Example 8

(5aR,9bS)-3-((4-Benzylpiperazin-1-yl)methyl)-3,3a-dihydroxy-5a,9-dimethyl-3,3a,4,5,5a,6,7,8-octahydronaphtho[1,2-b]furan-2(9bH)-one Benzyl piperazine (190 mg, 1.078 mmol) was added to the solution of compound of example 5 (470 mg, 1.078 mmol) in ethanol (15 mL), and stirred at 50° C. under nitrogen atmosphere for 6 hours. The reaction mixture was concentrated, and dissolved in water (25 mL) and was extracted using ethyl acetate (3×50 mL). Ethyl acetate layer was washed with water and brine, dried over sodium sulfate. Solvent was removed and crude product was purified by column chromatography (silica gel, using 12.5% ethyl acetate in petroleum ether). Semi-pure product was crystallized using ethyl acetate/petroleum ether to obtain the title compound.

Yield: 130 mg (27.4%); $^1$H NMR (CDCl$_3$, 300 MHz): δ 0.99 (s, 3H), 1.22-1.62 (m, 8H), 1.81-1.91 (m, 4H), 1.98-

2.18 (m, 3H), 2.47-2.82 (8H), 2.98 (bs, 2H), 3.48 (dd, 2H), 5.16 (s, 1H), 7.23-7.27 (m, 5H); MS m/e: 441 (M+1)

Example 9

(5aS,9bS)-3-((4-(((5aR,9bS)-3,3a-dihydroxy-5a,9-dimethyl-2-oxo-2,3,3a,4,5,5a,6,7,8,9b-decahydronaphtho[1,2-b]furan-3-yl)methyl)piperazin-1-yl) methyl)-3,3a-dihydroxy-5a,9-dimethyl-3,3a,4,5,5a,6, 7,8-octahydronaphtho[1,2-b]furan-2(9bH)-one A solution of compound of example 5 (400 mg, 0.91 mmol) and piperazine (39.51 mg, 0.45 mmol) in methanol (5 mL) was stirred for 24 hours at 45° C. Reaction mixture was concentrated, and to it water (50 mL) and saturated sodium bicarbonate solution were added. Reaction mixture was extracted with DCM (3×50 mL). The reaction mixture was concentrated and crude product was purified by column chromatography (silica gel, 0.2% methanol in chloroform) to obtain the title compound.

Yield: 200 mg (35.50%); $^1$H NMR (CDCl$_3$, 300 MHz): δ 0.99 (s, 6H), 1.35-1.60 (m, 16H), 1.77 (m, 6H), 2.00-2.12 (m, 4H), 2.40-2.53 (m, 4H), 2.86-3.01 (m, 4H), 3.01-3.45 (m, 4H), 5.17 (s, 2H); MS: m/e 615.3 (M+1).

Example 10

(5aR,9bS)-3a-Hydroxy-5a,9-dimethyl-3-(phenylthiomethyl)-3,3a,4,5,5a,6,7,8-octahydronaphtho[1,2-b] furan-2(9bH)-one Thiophenol (132 mg, 1.2 mmol) and triethylamine (TEA) (30 mg, 0.3 mmol) were added to the solution of compound of example 1 (248 mg, 1 mmol) in ethanol (10 mL). Reaction mixture was stirred for 3 hours at room temperature (25° C.). The reaction mixture was concentrated. The crude product was triturated with diethyl ether to obtain the title compound.

Yield: 130 mg (36.31%); $^1$H NMR (CDCl$_3$, 300 MHz): δ 1.07 (s, 3H), 1.35-1.51 (m, 3H), 1.6-1.7 (m, 3H), 1.59-1.76 (s, 3H), 1.84-2.06 (m, 2H), 2.08-2.17 (m, 2H), 2.29-3.11 (m, 2H), 3.54-3.58 (dd, 1H), 5.0 (s, 1H), 7.2-7.5 (m, 5H); MS: m/e 359.1 (M+1).

Example 11

2-(((5aR,9bS)-3a-Hydroxy-5a,9-dimethyl-2-oxo-2,3, 3a,4,5,5a,6,7,8,9b-decahydro naphtho[1,2-b]furan-3-yl)methylthio)acetic acid Thioglycolic acid (110 mg, 1.2 mmol) and TEA (61 mg, 0.6 mmol) were added to the solution of compound of example 1 (248 mg, 1 mmol) in ethanol (15 mL). Reaction mixture was stirred for 4 hours at room temperature (25° C.). The reaction mixture was concentrated and the crude product was purified by column chromatography (silica gel, 6% methanol in CHCl$_3$) to obtain the title compound.

Yield: 102 mg (30.0%); $^1$H NMR (CDCl$_3$, 300 MHz): δ 1.05 (s, 3H), 1.38-1.53 (m, 3H), 1.58-1.70 (m, 3H), 1.72-1.75 (m, 1H), 1.81 (s, 3H), 1.82-1.91 (m, 2H), 2.07-2.20 (m, 2H), 2.87-2.92 (m, 1H), 3.10-3.13 (m, 1H), 3.21-3.25 (m, 1H), 3.35-3.38 (d, 1H,), 3.45-3.48 (d, 1H,), 5.04 (s, 1H); MS m/e: 339.1 (M−1).

Example 12

(5aR,9bS)-3-((1H-Pyrazol-1-yl)-methyl)-3a-hydroxy-5a,9-dimethyl-3,3a,4,5,5a,6,7,8-octahydronaphtho[1,2-b]furan-2(9bH)-one TEA (36.36 mg 0.36 mmole) was added to the solution of compound of example 1 (248 mg, 1 mmol) and pyrazole (81.69 mg, 1.2 mmol) in ethanol (5 mL). The reaction mixture was stirred for 48 hours, was concentrated and crude product was purified by column chromatography (silica gel, 5% ethyl acetate in petroleum ether) to obtain the title compound.

Yield: 140 mg (44.3%); $^1$H NMR (CDCl$_3$, 300 MHz): δ 1.1 (s, 3H), 1.3-1.6 (m, 8H), 1.79 (s, 3H), 2.09-2.17 (m, 3H), 3.21-3.25 (m, 1H), 4.33-4.42 (m, 1H), 4.46-4.69 (m, 1H), 5.08 (s, 1H), 6.28 (t, 1H), 7.5-7.53 (m, 2H); MS: m/e 317 (M+1).

Example 13

(5aR,9bS)-3-((3,5-Dimethyl-1H-pyrazol-1-yl)methyl)-3a-hydroxy-5a,9-dimethyl-3,3a,4,5,5a,6,7,8-octahydronaphtho[1,2-b]furan-2(9bH)-one TEA (61.08 mg, 0.60 mmole) was added to the solution of compound of example 1 (500 mg, 2.016 mmol) and 2,5-dimethylpyrazole (232 mg, 2.41 mmol) in ethanol (10 mL). The reaction mixture was stirred for 48 hours, was concentrated and crude product was purified by column chromatography (silica gel, 5% ethyl acetate in petroleum ether) to obtain the title compound.

Yield: 300 mg (43.26%); $^1$H NMR (CDCl$_3$, 300 MHz): δ 1.08 (s, 3H), 1.3-1.7 (m, 8H), 1.81-1.84 (m, 4H), 2.15 (s, 3H), 2.33 (s, 3H), 3.31 (dd, 1H), 4.129 (q, 1H), 4.51 (d, 1H), 4.54 (d, 1H), 5.15 (s, 1H), 5.86 (s, 1H); MS: m/e 345 (M+1).

Example 14

(5aR,9bS)-3a-Hydroxy-5a,9-dimethyl-3-((2-methyl-1H-imidazol-1-yl)methyl)-3,3a,4,5,5a,6,7,8-octahydronaphtho[1,2-b]furan-2(9bH)-one 2-Methyl imidazole (232 mg, 2.8 mmol) and TEA (61 mg, 0.6 mmol) were added to the solution of compound of example 1 (500 mg, 2.016 mmol) in ethanol (10 mL). Reaction mixture was stirred for 50 hours at room temperature (25° C.). The reaction mixture was concentrated and crude product was purified by trituration with ethyl acetate. Non-polar impurities were removed by washing the product with diethyl ether and with small amount of petroleum ether. The product was crystallized using ethyl acetate/methanol to obtain the title compound.

Yield: 90 mg (13.41%); $^1$H NMR (CDCl$_3$, 300 MHz): δ 1.06 (s, 3H), 1.35-1.44 (m, 3H), 1.50-1.75 (m, 6H), 1.77 (s, 3H), 2.02-2.25 (m, 2H), 2.31 (s, 3H), 3.2 (t, 1H), 4.15-4.27 (m, 2H), 5.18 (s, 1H), 6.745 (bs, 1H), 7.13 (s, 1H); MS m/e: 331.2 (M+1).

Example 15

(5aR,9bS)-3-((1H-1,2,4-Triazol-1-yl)methyl)-3a-hydroxy-5a,9-dimethyl-3,3a,4,5,5a,6,7,8-octahydronaphtho[1,2-b]furan-2(9bH)-one TEA (36.7 mg, 0.36 mmol) and 1,2,4-triazole (105.2 mg, 1.52 mmol) were added to the solution of compound of example 1 (300 mg, 1.2 mmol) in ethanol (5 mL). The reaction mixture was stirred at room temperature (25° C.) for 15 hours. Reaction mixture was concentrated and crude product was purified by column chromatography (silica gel, 2% methanol in chloroform) to obtain the title compound.

Yield: 220 mg (57.83%); $^1$H NMR (CDCl$_3$, 300 MHz): δ 1.08 (s, 3H), 1.45-1.54 (m, 3H), 1.64-1.92 (m, 9H), 2.11-2.19 (m, 2H), 3.17-3.22 (dd, 1H), 4.34-4.41 (m, 1H), 4.81-4.86 (dd, 1H), 5.10 (s, 1H), 8.02 (s, 1H), 8.23 (s, 1H); MS: m/e 318.16 (M+1).

Example 16

1-(((5aR,9bS)-3a-Hydroxy-5a,9-dimethyl-2-oxo-2,3,3a,4,5,5a,6,7,8,9b-decahydronaphtho[1,2-b]furan-3-yl)methyl)pyrrolidine-2-carboxylic acid L-Proline (278.3 mg, 2.42 mmol) and TEA (61.1 mg, 0.61 mmol) were added to the solution of compound of example 1 (500 mg, 2.016 mmol) in ethanol (10 mL). The reaction mixture was stirred at room temperature (25° C.) for 7 hours. The reaction mixture was concentrated to dryness. The crude product was purified by washing with ether to remove non-polar impurities and then was washed with distilled water to remove the unreacted L-proline, to obtain the title compound.

Yield: 125 mg (17.08%); $^1$H NMR (CDCl$_3$, 300 MHz): δ 0.9 (s, 3H), 1.2-1.45 (m, 3H), 1.53-1.72 (m, 9H), 1.78-2.10 (m, 5H), 2.75-2.77 (m, 1H), 3.07-3.28 (m, 4H), 3.41-3.6 (m, 3H), 5.05 (s, 1H); MS: m/e 364.2 (M+1).

Example 17

(5aR,9bS)-3a-Hydroxy-5a,9-dimethyl-3-(piperidin-1-ylmethyl)-3,3a,4,5,5a,6,7,8-octahydronaphtho[1,2-b]furan-2(9bH)-one Compound of example 1 (2.5 g, 10 mmol) was added to piperidine (1 mL). The mixture was stirred at room temperature (25° C.) for 1 hour. Excess piperidine was removed using vacuum. Product was crystallized using diethyl ether to obtain the title compound.

Yield: 1.6 g (47.61%); $^1$H NMR (CDCl$_3$, 300 MHz): δ 1.05 (s, 3H), 1.35-1.70 (m, 12H), 1.78 (s, 3H), 1.86 (m, 2H), 2.11 (m, 2H), 2.33 (m, 2H), 2.65 (m, 2H), 2.79 (d, 2H,), 3.05 (dd, 1H), 5.00 (s, 1H); MS: m/e 334 (M+1).

Example 18

13-(Piperidin-1-yl)-4,5-epoxy-7-hydroxyeudesm-6,12-olide

Step 1
4α,5α-epoxy-7α-hydroxyeudesmanolide

Compound of example 1 (50 mg, 0.20 mmol) was dissolved in chloroform (5 mL). metachloroperbenzoic acid (138 mg, 0.80 mmol) was added to it at 0° C. and kept for 48 hours. Dichloromethane (100 mL) was added to the reaction mixture and was washed with saturated sodium bicarbonate solution and water. Solvent was removed and crude product was purified by column chromatography (silica gel, 25% ethyl acetate in petroleum ether) to obtain the epoxide.

Yield: 45 mg (85%); $^1$H NMR (CDCl$_3$, 300 MHz): δ 1.11 (s, 3H), 1.26-1.33 (m, 1H), 1.37 (s, 3H), 1.59-1.76 (m, 4H), 1.77-1.93 (m, 4H), 1.95-2.1 (m, 2H), 3.9 (s, 1H), 5.83 (s, 1H), 6.24 (s, 1H); MS: m/e 265 (M+1).
Step 2
Product obtained in step 1 (70 mg, 0.26 mmol) and piperidine (26 μL) were mixed and the mixture was stirred at room temperature (25° C.) for 1 hour. Excess piperidine was removed using vacuum. Petroleum ether (10 mL) was added to the mixture, product was separated, which corresponds to title compound.

Yield: 67 mg (74%); $^1$H NMR (CDCl$_3$, 300 MHz): δ 1.08 (s, 3H), 1.25 (m, 1H), 1.35 (s, 3H), 1.45-2.01 (m, 16H), 2.33 (m, 2H), 2.64 (m, 2H), 2.78 (d, 2H), 3.03 (dd, 1H), 3.95 (s, 1H); MS: m/e 350 (M+1).

Example 19

1-(((5aR,9bS)-3a-Hydroxy-5a,9-dimethyl-2-oxo-2,3,3a,4,5,5a,6,7,8,9b-decahydronaphtho[1,2-b]furan-3-yl)methyl)piperidin-4-one TEA (319 mg, 3.15 mmole) was added to a stirred solution of compound of example 1 (400 mg, 1.613 mmol) and 4-piperidone hydrochloride (331 mg, 2.43 mmol) in ethanol (10 mL). The reaction mixture was stirred for 15 hours. Reaction mixture was concentrated and crude product was purified by column chromatography (silica gel, 2% methanol in chloroform) to obtain the title compound.

Yield: 240 mg (42.88%); $^1$H NMR (CDCl$_3$, 300 MHz): δ 1.08 (s, 3H), 1.2-1.5 (m, 4H), 1.6-1.77 (m, 3H), 1.79 (s, 3H), 2.0-2.16 (m, 2H), 2.45-2.62 (m, 4H), 2.82-2.95 (m, 2H), 2.9-3.2 (m, 6H), 4.09 (q, 1H), 5.05 (s, 1H); MS: m/e 348 (M+1).

Example 20

(5aR,9bS)-3a-Hydroxy-3-((4-hydroxypiperidin-1-yl)methyl)-5a,9-dimethyl-3,3a,4,5,5a,6,7,8-octahydronaphtho[1,2-b]furan-2(9bH)-one 4-Hydroxy piperidine (196 mg, 1.94 mmol) and TEA (49 mg, 0.49 mmol) were added to the solution of compound of example 1 (400 mg, 1.612 mmol) in ethanol (10 mL). The reaction mixture was stirred for 14 hours at room temperature (25° C.). The reaction mixture was concentrated and the crude product was purified by column chromatography (silica gel, 30% ethyl acetate in petroleum ether). The title compound was obtained by crystallization using ethyl acetate/petroleum ether.

Yield: 88 mg (15.68%); $^1$H NMR (CDCl$_3$, 300 MHz): δ 1.06 (s, 3H), 1.35-1.44 (m, 3H), 1.54-1.73 (m, 5H), 1.78 (s, 3H), 1.78-1.83 (m, 2H), 1.89-2.26 (m, 5H), 2.55 (bs, 1H), 2.75-2.77 (m, 1H), 2.80-2.93 (m, 2H), 3.04-3.14 (m, 2H), 3.79 (s, 1H), 5.01 (s, 1H); MS m/e: 350.2 (M+1).

Example 21

(5aR,9bS)-3-(1,4'-Bipiperidin-1'-ylmethyl)-3a-hydroxy-5a,9-dimethyl-3,3a,4,5,5a,6,7,8-octahydronaphtho[1,2-b]furan-2(9bH)-one The solution of compound of example 1 (200 mg, 0.81 mmol) and 4-piperidino piperidine (149.28 mg, 0.88 mmol) in ethanol (5 mL) was stirred for 1 hour, reaction mixture was concentrated under vacuum and the title compound was obtained by crystallization using ethyl acetate/petroleum ether.

Yield: 250 mg (74.52%); $^1$H NMR (CDCl$_3$, 300 MHz): δ 1.05 (s, 3H), 1.38-1.42 (m, 6H), 1.58-1.65 (m, 4H), 1.79-1.82 (m, 4H), 1.86.-1.94 (m, 3H), 2.07-2.09 (m, 2H), 2.26-2.34 (m, 4H), 2.55 (bs, 5H), 2.77-2.84 (m, 2H), 2.88 (m, 1H), 3.03-3.08 (dd, 1H), 3.20 (d, 1H), 3.53 (s, 2H), 5.01 (s, 1H); MS: m/e 417 (M+1).

Example 22

(5aR,9bS)-3a-Hydroxy-5a,9-dimethyl-3-(morpholinomethyl)-3,3a,4,5,5a,6,7,8-octahydronaphtho[1,2-b]furan-2(9bH)-one Morpholine (52 μL) was added to compound of example 1 (150 mg, 0.60 mmol) and the mixture was stirred at room temperature (25° C.) for 1 hour. Excess morpholine was removed using vacuum. The title compound was crystallized using diethyl ether.

Yield: 100 mg (49.35%); $^1$H NMR (CDCl$_3$, 300 MHz): δ 1.05 (s, 3H), 1.39-1.65 (m, 7H), 1.79 (s. 3H), 1.89 (m, 1H), 2.08 (m, 2H), 2.44 (m, 2H), 2.72 (m, 2H), 2.85 (d, 2H), 3.06 (t, 1H), 3.71 (m, 4H), 5.01 (s, 1H); MS: m/e 336 (M+1).

Example 23

(5aR,9bS)-3a-hydroxy-5a,9-dimethyl-3-morpholinomethyl)decahydronaphtho[1,2-b]furan-2(9bH)-one Compound of example 22 (140 mg, 0.42 mmol) was dissolved in methanol (10 mL) and 10% Pd(OH)$_2$/C was added to it. The reaction mixture was hydrogenated (hydrogen pressure, 1 atm) for 2 hours. The reaction mixture was filtered over celite and concentrated to obtain the title compound.

Yield: 130 mg (92%); $^1$H NMR (CDCl$_3$, 300 MHz): δ 1.11-1.17 (d, 6H), 1.27-1.68 (m, 9H), 1.72-2.05 (m, 3H), 2.42-2.46 (m, 1H), 2.64-3.09 (m, 6H), 3.89 (s, 4H), 5.36 (s, 1H);
MS: m/e 336.2 (M−1).

Example 24

(5aR,9bS)-3a-Hydroxy-5a,9-dimethyl-3-(thiomorpholinomethyl)-3,3a,4,5,5a,6,7,8-octahydronaphtho[1,2-b]furan-2(9bH)-one Thiomorpholine (0.1 mL) was added to compound of example 1 (250 mg, 1.0 mmol) and the mixture was stirred at room temperature (25° C.) for 1 hour. Excess thiomorpholine was removed using vacuum. Title compound separated out on addition of diethyl ether.

Yield: 240 mg (68%); $^1$H NMR (CDCl$_3$, 300 MHz): δ 1.03 (s, 3H), 1.35-1.73 (m, 7H), 1.77 (s, 3H), 1.86 (m, 1H), 2.11 (m, 2H), 2.60-2.93 (m, 8H), 3.02 (m, 2H), 3.10 (dd, 1H), 3.53 (s, 1H), 5.00 (s, 1H); MS: m/e 351.19 (M$^+$).

Example 25

(5aR,9bS)-3a-Hydroxy-5a,9-dimethyl-3-(thiomorpholino-1-oxide-methyl)-3,3a,4,5,5a,6,7,8-octahydronaphtho[1,2-b]furan-2(9bH)-one Compound of example 24 (190 mg, 0.54 mmol) was dissolved in methanol (5 mL) and mixture was cooled to 0° C. Sodium periodate (139 mg, 0.65 mmol) in water (1 mL) was added to it and the reaction mixture was kept at 0° C. for 15 hours. Reaction mixture was extracted with ethyl acetate (3×100 mL) and ethyl acetate layer was washed with water and brine. The ethyl acetate was dried over sodium sulfate. Solvent was removed and the crude product was purified by column chromatography (silica gel, 10% methanol in dichloromethane) to obtain the title compound.

Yield: 150 mg (75%); $^1$H NMR (CDCl$_3$, 300 MHz): δ 1.04 (s, 3H), 1.25-1.68 (m, 7H), 1.78 (s, 3H), 1.88 (m, 1H), 2.11 (m, 2H), 2.70-3.17 (m, 11H), 3.32 (t, 1H), 5.00 (s, 1H); MS: m/e 368 (M+1).

Example 26

(5aR,9bS)-3a-hydroxy-5a,9-dimethyl-3-((4-methylpiperazin-1-yl)methyl)-3,3a,4,5,5a,6,7,8-octahydronaphtho[1,2-b]furan-2(9bH)-one hydrochloride Step 1
(5aR,9bS)-3a-hydroxy-5a,9-dimethyl-3-((4-methylpiperazin-1-yl)methyl)-3,3a,4,5,5a,6,7,8-octahydronaphtho[1,2-b]furan-2(9bH)-one N-Methyl piperazine (242 mg, 2.424 mmol) and TEA (61.21 mg, 0.606 mmol) were added to the solution of compound of example 1 (500 mg, 2.016 mmol) in ethanol (10 mL). Reaction mixture was stirred for 20 hours at room temperature (25° C.). The reaction mixture was concentrated and the crude product was purified by column chromatography (silica gel, 2% methanol in chloroform).

Yield: 84 mg, (11.97%)

Step 2
Preparation of Hydrochloride

Compound obtained in step 1 was dissolved in dry methanol (3 mL) and to it methanolic hydrochloric acid was added till pH was about 4. Reaction mixture was concentrated and the residue was washed with dry diethyl ether to obtain the title compound.

Yield: 63 mg, (67.96%); $^1$H NMR (CDCl$_3$, 300 MHz): δ 0.95 (s, 3H), 1.17-1.56 (m, 6H), 1.67-1.73 (bs, 5H), 2.04-2.09 (m, 2H), 2.49-2.50 (m, 4H), 2.8 (s, 3H), 3.07-3.98 (m, 6H), 5.1 (s, 1H); MS: m/e 348.2 (M+).

Example 27

(5aR,9bS)-3-((4-Benzylpiperazin-1-yl)methyl)-3a-hydroxy-5a,9-dimethyl-3,3a,4,5,5a,6,7,8-octahydronaphtho[1,2-b]furan-2(9bH)-one The solution of compound of example 1 (300 mg, 1.20 mmol) and N-benzyl piperazine (276 mg, 1.57 mmol) in ethanol (5 mL) was stirred for 2 hours. Reaction mixture was concentrated and crude product was purified by column chromatography (silica gel, 15% ethyl acetate in petroleum ether) to obtain the title compound.

Yield: 350 mg (68.35%); $^1$H NMR (CDCl$_3$, 300 MHz): δ 1.06 (s, 3H), 1.40-1.48 (m, 4H), 1.63-1.68 (m, 4H), 1.80-1.88 (m, 4H), 2.08-2.19 (m, 2H), 2.52 (bs, 8H), 2.85-2.90 (m, 2H), 3.02-3.15 (m, 1H), 3.53 (s, 2H), 5.03 (s, 1H), 7.28-7.35 (m, 5H); MS: m/e 425 (M+1).

Example 28

(5aR,9bS)-3a-hydroxy-5a,9-dimethyl-3-(piperazin-1-ylmethyl)-3,3a,4,5,5a,6,7,8-octahydronaphtho[1,2-b]furan-2(9bH)-one Compound of example 27 (100 mg, 0.24 mmol) was dissolved in ethanol (10 mL) and to it 10% Pd/C & 10% aqueous HCl (0.1 mL) was added. The reaction mixture was stirred under hydrogen pressure for 30 hours at room temperature (25° C.). The reaction mixture was filtered over celite and concentrated under reduced pressure to obtain the title compound.

Example 29

(5aR,9bS)-3a-hydroxy-5a,9-dimethyl-3-(piperazin-1-ylmethyl)decahydronaphtho[1,2-b]furan-2(9bH)-one Compound of example 27 (100 mg, 0.47 mmol) was dissolved in methanol (10 mL) and 10% Pd(OH)$_2$/C was added to it. The reaction mixture was hydrogenated (hydrogen pressure, 1 atm) for 30 hours. The reaction mixture was filtered over celite and concentrated to obtain the title compound
Yield: 100 mg (95%); $^1$H NMR (CDCl$_3$, 300 MHz): δ 1.02 (s, 3H), 1.16 (s, 3H), 1.41-1.70 (m, 11H), 2.11-2.12 (m, 2H), 2.43-2.9 (m, 11H), 5.43 (s, 1H). MS: m/e 335.2 (M−1).

Example 30

(5aR,9bS)-3-((4-(2,6-dimethylbenzyl)piperazin-1-yl)methyl)-3a-hydroxy-5a,9-dimethyl-3,3a,4,5,5a,6,7,8-octahydronaphtho[1,2-b]furan-2(9bH)-one 1-(2,6-dimethylbenzyl)piperazine (244.8 mg, 1.2 mmol) was added to the solution of compound of example 1 (248 mg, 1 mmol) in ethanol (10 mL) and reaction mixture was stirred at room temperature (25° C.) for 15 hours. The reaction mixture was concentrated, the crude product was purified silica gel column chromatography (silica gel, 15% ethyl acetate in petroleum ether) to obtain the compound.
Yield: 190 mg (42%); $^1$H NMR (CDCl$_3$, 300 MHz): δ 1.05 (s, 3H), 1.25-1.72 (m, 8H), 1.79-2.31 (m, 5H), 2.46-2.77 (m, 14H), 2.79-3.05 (m, 3H), 3.46 (s, 2H), 5.01 (s, 1H), 6.98-7.07 (m, 3H); MS m/e: 453 (M+1).

Example 31

(5aR,9bS)-3-((4-(3,5-dimethoxy-2-methylbenzyl)piperazin-1-yl)methyl)-3a-hydroxy-5a,9-dimethyl-3,3a,4,5,5a,6,7,8-octahydronaphtho[1,2-b]furan-2(9bH)-one 1-(3,5-Dimethoxy-2-methylbenzyl)piperazine (300 mg, 1.2 mmol) was added to the solution of compound of example 1 (248 mg, 1 mmol) in ethanol (20 mL) and reaction mixture was stirred at room temperature (25° C.) for 15 hours. The reaction mixture was concentrated, dried and the compound was purified by column chromatography (silica gel, 15% ethyl acetate in petroleum ether) to obtain the compound.
Yield: 180 mg (36.14%); $^1$HNMR (CDCl$_3$, 300 MHz): δ 0.97 (s, 3H), 1.25-2.15 (m, 17H), 2.3-2.6 (bs, 6H), 2.74-2.87 (m, 3H), 3.42 (s, 2H), 3.78-3.79 (d, 6H), 5.01 (s, 1H), 6.384 (d, 1H,), 6.465 (d, 1H,); MS m/e: 499 (M+1).

Example 32

(5aR,9bS)-3a-hydroxy-3-((4-(2-(hydroxymethyl)-3,5-dimethoxy-6-methylbenzyl)piperazin-1-yl)methyl)-5a,9-dimethyl-3,3a,4,5,5a,6,7,8-octahydronaphtho[1,2-b]furan-2(9bH)-one (4,6-dimethoxy-3-methyl-2-(piperazin-1-ylmethyl)phenyl)methanol (180 mg, 0.64 mmol) was added to the solution of compound of example 1 (145 mg, 0.58 mmol) in ethanol (15 mL) and reaction mixture was stirred at room temperature (25° C.) for 36 hours. The reaction mixture was concentrated, dried and the compound was purified by column chromatography (silica gel, 15% ethyl acetate in petroleum ether) as eluant to obtain the compound.
Yield: 120 mg (38.87%); $^1$HNMR (CDCl$_3$, 300 MHz): δ 1.2-1.3 (m, 5H), 1.35-1.5 (m, 5H), 1.7-1.86 (m, 4H), 2.24-2.27 (m, 5H), 2.74-2.82 (m, 11H), 3.67 (s, 2H), 3.821-3.825 (d, 6H), 4.65 (s, 2H), 4.98 (s, 1H), 6.44 (s, 1H); MS m/e: 529 (M+1).

Example 33

(5aR,9bS)-3-((4-(2-fluorobenzyl)piperazin-1-yl)methyl)-3a-hydroxy-5a,9-dimethyl-3,3a,4,5,5a,6,7,8-octahydronaphtho[1,2-b]furan-2(9bH)-one 1-(2-Fluoro-benzyl)-piperazine (233.1 mg, 1.2 mmol) was added to the solution of compound of example 1 (248 mg, 1 mmol) in ethanol (10 mL), and was stirred at room temperature for 4 hours. The reaction mixture was concentrated, crude product was purified by column chromatography (silica gel, 25% ethyl acetate in petroleum ether to obtain the title compound.
Yield: 220 mg (49.7%); $^1$H NMR (CDCl$_3$, 300 MHz): δ 1.04 (s, 3H), 1.37-1.44 (m, 6H), 1.78-1.87 (m, 5H), 2.06-2.83 (m, 8H), 2.85-3.07 (m, 5H), 3.58 (s, 2H), 5.00 (s, 1H), 6.99-7.34 (m, 4H); MS m/e: 443 (M+1).

Example 34

(5aR,9bS)-3a-hydroxy-5a,9-dimethyl-3-((4-(perfluorobenzyl)piperazin-1-yl)methyl)-3,3a,4,5,5a,6,7,8-octahydronaphtho[1,2-b]furan-2(9bH)-one A solution of compound of example 1 (300 mg, 1.20 mmol) and 1-(perfluorobenzyl)piperazine (351.4 mg, 1.32 mmol) in ethanol (10 mL) was stirred at room temperature (25° C.) for 12 hours. Reaction mixture was concentrated and was purified by column chromatography (silica gel, 12% ethyl acetate in petroleum ether) to obtain the title compound.
Yield: 250 mg (40%); $^1$H NMR (CDCl$_3$, 300 MHz): δ 1.04 (s, 3H), 1.25-1.71 (m, 8H), 1.78 (s, 3H), 2.00-2.18 (m, 2H), 2.44-2.74 (m, 8H), 2.78-2.87 (m, 2H), 2.98-3.08 (m, 1H), 3.73 (s, 2H), 4.99 (s, 1H); MS: m/e 515.23 (M+1).

Example 35

(5aR,9bS)-3-((4-(2-chloro-6-fluorobenzyl)piperazin-1-yl)methyl)-3a-hydroxy-5a,9-dimethyl-3,3a,4,5,5a,6,7,8-octahydronaphtho[1,2-b]furan-2(9bH)-one A solution of compound of example 1 (250 mg, 1.21 mmol) and 1-(2-chloro-6-fluorobenzyl)piperazine (228.69 mg, 1.33 mmol) in ethanol (10 mL) was stirred at room temperature (25° C.) for 12 hours. Reaction mixture was concentrated and purified by column chromatography (silica gel, 20% ethyl acetate in petroleum ether) to obtain the title compound.
Yield: 300 mg (52%); $^1$H NMR (CDCl$_3$, 300 MHz): δ 1.01 (s, 3H), 1.20-1.35 (m, 2H), 1.36-1.50 (m, 4H), 1.62-1.71 (m, 2H), 1.77 (s, 3H), 2.08-2.11 (m, 2H), 2.79-3.01 (m, 8H), 3.15-3.22 (m, 1H), 3.34-3.38 (m, 2H), 3.74 (s, 2H), 5.06 (s, 1H), 6.95-7.01 (m, 1H), 7.18-7.25 (m, 2H); MS: m/e 477.2 (M+1).

Example 36

(5aR,9bS)-3-((4-(2-fluoro-6-(trifluoromethyl)benzyl) piperazin-1-yl)methyl)-3a-hydroxy-5a,9-dimethyl-3, 3a,4,5,5a,6,7,8-octahydronaphtho[1,2-b]furan-2 (9bH)-one A solution of compound of example 1 (250 mg, 1.01 mmol) and 1-(2-fluoro-6-(trifluoromethyl)benzyl)piperazine (290.8 mg, 1.11 mmol) in ethanol (10 mL) was stirred at room temperature (25° C.) for 12 hours. Reaction mixture was concentrated and purified by column chromatography (silica gel, 12% ethyl acetate in petroleum ether) to obtain the title compound.

Yield: 325 mg (63%); $^1$H NMR (CDCl$_3$, 300 MHz): δ 1.04 (s, 3H), 1.25-1.75 (m, 8H), 1.78 (s, 3H), 1.83-2.00 (m, 2H), 2.32-2.72 (m, 8H), 2.75-2.89 (m, 3H), 3.66 (s, 2H), 5.01 (s, 1H), 6.95-7.01 (m, 1H), 7.18-7.25 (m, 2H); MS: m/e 511.25 (M+1).

Example 37

(5aR,9bS)-3-((4-(benzo[d][1,3]dioxol-4-ylmethyl) piperazin-1-yl)methyl)-3a-hydroxy-5a,9-dimethyl-3, 3a,4,5,5a,6,7,8-octahydronaphtho[1,2-b]furan-2 (9bH)-one A solution of compound of example 1 (200 mg, 0.81 mmol) and 1-(benzo[d][1,3]dioxol-4-ylmethyl)piperazine (195.40 mg, 0.88 mmol) in ethanol (10 mL) was stirred at room temperature (25° C.) for 2 hours. Reaction mixture was concentrated and was purified by column chromatography (silica gel, 25% ethyl acetate in petroleum ether to obtain the title compound.

Yield: 200 mg (53%); $^1$H NMR (CDCl$_3$, 300 MHz): δ 1.05 (s, 3H), 1.23-1.27 (m, 2H), 1.38-1.44 (m, 2H), 1.61-1.74 (m, 4H), 1.78 (s, 3H), 2.04-2.08 (m, 2H), 2.62 (m, 6H), 2.91-3.03 (m, 5H), 3.47 (s, 2H), 5.03 (s, 1H), 5.94 (s, 2H), 6.73-6.83 (m, 3H); MS: m/e 469.3 (M+1).

Example 38

(5aR,9bS)-3a-hydroxy-3-((4-(2-(hydroxymethyl)-3, 5-dimethoxybenzyl)piperazin-1-yl)methyl)-5a,9-dimethyl-3,3a,4,5,5a,6,7,8-octahydronaphtho[1,2-b] furan-2(9bH)-one A solution of compound of example 1 (250 mg, 1.01 mmol) and (2,4-dimethoxy-6-(piperazin-1-ylmethyl)phenyl)methanol (295.26 mg, 1.11 mmol) in ethanol (10 mL) was stirred at room temperature (25° C.) for 12 hours, concentrated and purified by column chromatography (silica gel 60% ethyl acetate in petroleum ether). Crude product was crystallised from ethyl acetate and petroleum ether (7:3) to obtain the title compound.

Yield: 250 mg (48%); $^1$H NMR (CDCl$_3$, 300 MHz): δ 1.04 (s, 3H), 1.37-1.46 (m, 4H), 1.57-1.64 (m, 4H), 1.78 (s, 3H), 1.82-1.88 (m, 2H), 2.08-2.11 (m, 2H), 2.3-2.7 (m, 8H), 2.76-2.82 (m, 2H), 2.99-3.02 (m, 1H), 3.53 (s, 2H), 3.79 (s, 3H), 3.82 (s, 3H), 4.65 (s, 2H), 4.99 (s, 1H), 6.35 (d, 1H), 6.45 (d, 1H); MS m/e 515 (M+1).

Example 39

2-((4-(((5aR,9bS)-3a-hydroxy-5a,9-dimethyl-2-oxo-2,3,3a,4,5,5a,6,7,8,9b-decahydro naphtho[1,2-b] furan-3-yl)methyl)piperazin-1-yl)methyl)-4,6-dimethoxybenzyl acetate Compound of example 38 (200.0 mg, 0.39 mmol) was dissolved in DCM (10 mL). To it was added acetic anhydride (43.86 mg, 0.43 mmol), pyridine (61.70 mg, 0.78 mmol) and DMAP (2 mg) and reaction mixture was stirred at room temperature (25° C.) for 2 hours. Reaction mixture was diluted with water and extracted with DCM (3×50 mL). The crude product was purified by column chromatography (silica gel, 40% ethyl acetate in petroleum ether) to obtain the title compound.

Yield: 110 mg (51%); $^1$H NMR (CDCl$_3$, 300 MHz): δ 1.16 (s, 3H), 1.37-1.49 (m, 4H), 1.55-1.74 (m, 4H), 1.78 (s, 3H), 2.04 (s, 3H), 2.11-2.18 (m, 2H), 2.28-2.41 (m, 6H), 2.70-2.89 (m, 5H), 3.54 (s, 2H), 3.80 (s, 3H), 3.81 (s, 3H), 5.0 (s, 1H), 5.25 (s, 2H), 6.41 (d, 1H), 6.48 (d, 1H); MS: m/e 557.3 (M+1).

Example 40

2-((4-(((5aR,9bS)-3a-hydroxy-5a,9-dimethyl-2-oxo-2,3,3a,4,5,5a,6,7,8,9b-decahydronaphtho[1,2-b]furan-3-yl)methyl)piperazin-1-yl)methyl)-4,6-dimethoxybenzaldehyde oxime To the solution of compound of example 1 (48.3 mg, 0.195 mmol) in ethanol (5 mL), 2,4-dimethoxy-6-(piperazin-1-ylmethyl)benzaldehyde oxime (60 mg, 0.215 mmol) and TEA (6 mg, 0.06 mmol) were added successively and stirred at room temperature (25° C.) for 15 hours. The reaction mixture was concentrated, dried and purified by silica gel preparative TLC plate using 90% ethyl acetate in petroleum ether solvent system, to obtain the title compound.

Yield: 6 mg (5.8%); MS: m/e 528.3 (M+1).

Example 41

2-((4-(((5aR,9bS)-3a-hydroxy-5a,9-dimethyl-2-oxo-2,3,3a,4,5,5a,6,7,8,9b-decahydronaphtho[1,2-b]furan-3-yl)methyl)piperazin-1-yl)methyl)-4,6-dimethoxybenzaldehyde 2,4-Dimethoxy-6-(piperazin-1-ylmethyl)benzaldehyde (639 mg, 2.42 mmol) was added to the solution of compound of example 1 (500 mg, 2.02 mmol) in ethanol (30 mL) and reaction mixture was stirred at room temperature (25° C.) for 15 hours. The reaction mixture was concentrated, dried and the compound was purified by column chromatography (silica gel, 25% ethyl acetate in petroleum ether) to obtain the title compound.

Yield: 500 mg (48.5%); $^1$HNMR (CDCl$_3$, 300 MHz): δ 1.05 (s, 3H), 1.25-1.5 (m, 7H), 1.78 (s, 3H), 2.06-2.13 (m, 2H), 2.27-2.43 (bs, 8H), 2.44-2.65 (m, 3H), 2.81-2.93 (m, 3H), 3.80-3.88 (d, 6H), 5.01 (s, 1H), 6.372-6.379 (d, 1H), 6.826-6.828 (d, 1H), 10.43 (s, 1H);

MS m/e: 513 (M+1).

Example 42

2-((4-(((5aR,9bS)-3a-hydroxy-5a,9-dimethyl-2-oxo-2,3,3a,4,5,5a,6,7,8,9b-decahydro naphtho[1,2-b] furan-3-yl)methyl)piperazin-1-yl)methyl)-4,6-dimethoxybenzoic acid Ethyl acetate (10 mL) was added to a mixture of compound of example 38 (150 mg, 0.29 mol) and KBr in water (0.5 M, 0.24 mL), followed by addition of TEMPO (3.12 mg, 0.02 mmol). A solution of 12% NaClO in water (27 mg, 0.36 mmol) was added dropwise to the mixture over 30 minutes at 5° C. at pH of 8.0-10.0. Stirring was continued for 30 minutes at room temperature (25° C.). Then, the pH was adjusted to 5.0 by addition of 35% hydrochloric acid, followed by addition of 25% NaClO$_2$ in water (32.8 mg, 0.36 mmol) over 30 minutes maintaining the temperature of 27-33° C. Stirring was continued for 3 hours at room temperature (25° C.). The product was extracted with ethyl acetate (3×50 mL), washed with brine, followed by concentration to obtain the title compound.

Yield: 40 mg (25.9%); $^1$H NMR (CDCl$_3$, 300 MHz): δ 1.02 (s, 3H), 1.25-1.32 (m, 4H), 1.62-1.70 (m, 4H), 1.76 (s, 3H), 2.06-2.08 (m, 2H), 2.7-3.1 (m, 11H), 3.62 (s, 2H), 3.82 (s, 3H), 3.85 (s, 3H), 5.05 (s, 1H), 6.39 (s, 1H), 6.47 (s, 1H); MS m/e 529.28 (M+1).

Example 43

(5aR,9bS)-3-((4-benzylpiperazin-1-yl)methyl)-5a,9-dimethyl-2,3,3a,4,5,5a,6,7,8,9b-decahydronaphtho[1,2-b]furan-2,3a-diol Compound of example 27 (200 mg, 0.47 mmol) was dissolved in anhydrous DCM and toluene (1:1) (2 mL) and solution was cooled to −78° C. DIBAL in toluene (1.0 M, 1.4 mL, 1.2 equivalents) was added dropwise at −78° C. and mixture was stirred for 3 hours. Saturated sodium sulphate solution was added and reaction mixture was extracted by DCM (3×50 mL), dried over sodium sulphate and was concentrated to obtain the title compound.

Yield: 190 mg (95%); $^1$H NMR (CDCl$_3$, 300 MHz): δ 1.11 (s, 3H), 1.16-1.74 (m, 8H), 1.74 (s, 3H), 2.04-2.10 (m, 2H), 2.40-2.59 (m, 11H), 3.54 (m, 2H), 4.5 (s, 1H), 5.39 (d, 1H), 7.26-7.29 (m, 5H); MS: m/e 427.3 (M+1).

Example 44

(5aR,9bS)-3-(4-benzylpiperazin-1-yl)methyl)-3a-hydroxy-5a,9-dimethyl-2,3,3a,4,5,5a,6,7,8,9b-decahydronaphtho[1,2-b]furan-2-yl acetate Compound of example 27 (1000 mg, 2.35 mmole) was dissolved in anhydrous DCM and toluene (1:1) (20 mL) and this solution was cooled to −78° C. DIBAL in toluene (1.0 M, 1006 mg, 7.07 mmol) was added dropwise at −78° C. and mixture was stirred for 3 hours. To this mixture was added, pyridine (652.9 mg, 8.25 mmol), acetic anhydride (962.9 mg, 9.43 mmol) and DMAP (345.6 mg, 2.82 mmol) were added and reaction mixture was stirred for 3 hours at −78° C., followed by stirring for 12 hours at room temperature (25° C.). Reaction was quenched with 15 mL of saturated ammonium chloride solution. The organic layer was washed with brine, concentrated and was purified by column chromatography (silica gel, 50% ethyl acetate in petroleum ether) to obtain the title compound.

Yield: 400 mg (36.26%). $^1$H NMR (CDCl$_3$, 300 MHz); δ 1.15 (s, 3H), 1.27-1.70 (m, 8H), 1.78 (s, 3H), 1.85-2.04 (m, 2H), 2.08 (s, 3H), 2.39-2.51 (bm, 10H), 2.68-2.72 (m, 1H), 3.51-3.52 (m, 2H), 4.87 (s, 1H), 5.89 (d, 1H), 7.28-7.36 (m, 5H); MS: m/e 469.3 (M+1).

Example 45

(5aR,9bS)-3a-hydroxy-5a,9-dimethyl-3-((4-phenethylpiperazin-1-yl)methyl)-3,3a,4,5,5a,6,7,8-octahydronaphtho[1,2-b]furan-2(9bH)-one A solution of compound of example 1 (300 mg, 1.2 mmol) and 1-phenethylpiperazine (252 mg, 1.33 mmol) in ethanol (5 mL) was stirred for 12 hours. Reaction mixture was concentrated and purified by column chromatography (silica gel, 15% ethyl acetate in petroleum ether). Product was crystallised using ethyl acetate and petroleum ether (7:3) to obtain the title compound.

Yield: 175 mg (33%); $^1$H NMR (CDCl$_3$, 300 MHz): δ 1.02 (s, 3H), 1.33-1.47 (m, 4H), 1.53-1.71 (m, 4H), 1.76 (m, 3H), 1.98-2.05 (m, 2H), 2.37-2.60 (m, 8H), 2.74-2.89 (m, 7H), 4.99 (s, 1H), 7.15-7.31 (m, 5H); MS: m/e 439.3 (M+1).

Example 46

(5aR,9bS)-3-((4-benzylpiperazin-1-yl)methyl)-5a,9-dimethyl-2,3,3a,4,5,5a,6,7,8,9b-decahydronaphtho[1,2-b]furan-3a-ol Step 1

(1S,4aR)-2-(1-(4-benzylpiperazin-1-yl)-3-hydroxypropan-2-yl)-4a,8-dimethyl-1,2,3,4,4a,5,6,7-octahydronaphthalene-1,2-diol To the solution of compound of example 27 (424 mg, 1 mmol) in THF (20 mL) under stirring to 0° C., under nitrogen, was added LAH (132.8 mg, 3.5 mmol) and stirred at room temperature (25° C.) for 15 hours. The reaction mixture was quenched with water (3×50 mL), stirred for 10-15 minutes and added ethyl acetate (3×100 mL). The separated ethyl acetate layer was dried over sodium sulphate. The product was obtained by concentrating the ethyl acetate portion. It was dried under vacuum. Crude product was washed with petroleum ether which was crystallized using ethyl acetate (2 mL) and petroleum ether (5-6 drops) to obtain the title compound.

Yield: 250 mg (58.4%); $^1$H NMR (DMSO-d$_6$, 300 MHz): δ 1.1 (s, 3H), 1.15-1.3 (m, 3H), 1.5-2.3 (m, 16H), 2.7-2.8 (m, 1H), 3.2 (m, 1H), 3.42-3.43 (m, 2H), 3.61-3.64 (m, 1H), 3.86 (s, 1H), 4.13 (s, 1H), 4.52 (s, 1H), 5.78 (s, 1H), 7.2-7.3 (m, 5H); MS: m/e 429 (M+1).

Step 2

(5aR,9bS)-3-((4-benzylpiperazin-1-yl)methyl)-5a,9-dimethyl-2,3,3a,4,5,5a,6,7,8,9b-decahydronaphtho[1,2-b]furan-3a-ol To the solution of compound of step 1 (200 mg, 0.46 mmol) in pyridine (4 mL), p-toluene sulphonylchloride (61 mg, 0.32 mmol) was added and stirred at 80° C. for 360 hours. The reaction mixture was concentrated, dried and added (3×50 mL), ethylacetate and washed with water (3×50 mL). Organic layer was separated, dried and concentrated. The compound was purified by column chromatography (silica gel, 10% ethyl acetate in petroleum ether) to obtain the compound.

Yield: 100 mg, (52.08%); $^1$HNMR (CDCl$_3$, 300 MHz): δ 0.96 (s, 3H), 1.31-1.42 (m, 5H), 1.46-1.74 (m, 6H), 1.84-2.04 (m, 2H), 2.3-2.7 (m, 11H), 3.39-3.46 (m, 4H), 3.87-3.90 (m, 1H), 4.27 (s, 1H), 7.23-7.30 (m, 5H); MS: m/e 411 (M+1).

Example 47

(5aR,9bS)-3-((4-Acetylpiperazin-1-yl)methyl)-3a-hydroxy-5a,9-dimethyl-3,3a,4,5,5a,6,7,8-octahydronaphtho[1,2-b]furan-2(9bH)-one The solution of compound of example 1 (400 mg, 1.612 mmol) and N-acetyl piperazine (227 mg, 1.774 mmol) in ethanol (5 mL) was stirred for 15 hours. Reaction mixture was concentrated and crude product was purified by column chromatography (silica gel, 50% ethyl acetate in petroleum ether). The title compound was obtained by crystallization using ethyl acetate/petroleum ether.

Yield: 180 mg (29.68%); $^1$H NMR (CDCl$_3$, 300 MHz): δ 1.018 (s, 3H), 1.32-1.46 (m, 3H), 1.53-1.66 (m, 3H), 1.75 (bs, 4H), 1.82-1.91 (m, 1H) 1.98-2.16 (m, 6H), 2.35-2.4 (m, 2H), 2.6-2.71 (m, 2H), 2.75-2.84 (m, 2H), 3.02-3.07 (m, 1H), 3.35-3.48 (m, 2H), 3.51-3.56 (m, 2H), 4.98 (s, 1H); MS: m/e 377 (M+1).

Example 48

Ethyl 4-(((5aR,9bS)-3a-hydroxy-5a,9-dimethyl-2-oxo-2,3,3a,4,5,5a,6,7,8,9b-decahydronaphtho[1,2-b]furan-3-yl)methyl)piperazine-1-carboxylate hydrochloride Step 1
Ethyl 4-(((5aR,9bS)-3a-hydroxy-5a,9-dimethyl-2-oxo-2,3,3a,4,5,5a,6,7,8,9b-decahydronaphtho[1,2-b]furan-3-yl)methyl)piperazine-1-carboxylate Ethyl-1-piperazine carboxylate (459 mg, 2.9 mmol) and TEA (73 mg, 0.73 mmol) were added to the solution of compound of example 1 (600 mg, 2.42 mmol) in ethanol (10 mL). The reaction mixture was stirred for 4 hours at room temperature (25° C.). The reaction mixture was concentrated and crude product was purified by column chromatography (silica gel, 20% ethyl acetate in petroleum ether) to obtain free base.

Yield: 536 mg (54.52%); MS: m/e 406.2 (M+).
Step 2
Preparation of Hydrochloride

The product (450 mg) obtained in step 1 was dissolved in dry methanol (5 mL) and to it methanolic hydrochloric acid was added till pH was about 4, under stirring for 15 minutes. Reaction mixture was concentrated and crude product was washed with diethyl ether.

Yield: 450 mg (91.85%); $^1$H NMR (CDCl$_3$, 300 MHz): δ 1.019 (s, 3H), 1.20-1.67 (m, 8H), 1.79 (bs, 4H), 2.08-2.17 (m, 4H), 2.91 (bs, 2H), 3.18 (m, 1H), 3.74-4.08 (m, 6H) 4.18 (q, 4H), 5.15 (s, 1H), 5.67 (s, 1H), 11.61 (bs, 1H); MS: m/e 407.2 (M+1).

Example 49

(5aR,9bS)-3a-Hydroxy-5a,9-dimethyl-3-((4-phenylpiperazin-1-yl)methyl)-3,3a,4,5,5a,6,7,8-octahydronaphtho[1,2-b]furan-2(9bH)-one The solution of compound of example 1 (500 mg, 2.016 mmol) and 1-phenyl piperazine (425 mg, 2.62 mmol) in ethanol (5 mL) was stirred and TEA (61.0 mg, 0.6 mmole) was added. The reaction mixture was stirred for 4 hours, concentrated and crude product was purified by column chromatography (silica gel, 10% ethyl acetate in petroleum ether) to obtain title compound.

Yield: 450 mg (54.43%); $^1$H NMR (CDCl$_3$, 300 MHz): δ 1.1 (s, 3H), 1.39-1.46 (m, 4H), 1.63-1.72 (m, 4H), 1.79 (s, 3H), 2.07-2.09 (m, 3H), 2.71-2.73 (m, 2H), 2.95-3.02 (m, 4H), 3.19-3.28 (m, 5H), 5.05 (s, 1H), 6.89-6.93 (m, 3H), 7.25-7.30 (m, 2H); MS: m/e 411 (M+1).

Example 50

(5aR,9bS)-3a-Hydroxy-5a,9-dimethyl-3-((4-o-tolylpiperazin-1-yl)methyl)-3,3a,4,5,5a,6,7,8-octahydronaphtho[1,2-b]furan-2(9bH)-one hydrochloride Step 1
(5aR,9bS)-3a-Hydroxy-5a,9-dimethyl-3-((4-o-tolylpiperazin-1-yl)methyl)-3,3a,4,5,5a,6,7,8-octahydronaphtho[1,2-b]furan-2(9bH)-one 1-(Methylphenyl)piperazine (354 mg, 2.01 mmol) and TEA (60.6 mg, 0.606 mmol) were added to the solution of compound of example 1 (500 mg, 2.016 mmol) in ethanol (10 mL). The reaction mixture was stirred at room temperature (25° C.) for 15 hours. The reaction mixture was concentrated. The crude product was purified by column chromatography (silica gel, 6% ethyl acetate in petroleum ether) to obtain the free base.

Yield: 120 mg (14%); MS: m/e 405 (M−18)
Step 2
Preparation of Hydrochloride

The compound obtained in step 1 was dissolved in dry methanol (3 mL) and methanolic hydrochloric acid was added till pH was about 4, under stirring. Mixture was concentrated and product was washed with dry diethylether to obtain the title compound.

Yield: 130 mg (99.77%); $^1$H NMR (CDCl$_3$, 300 MHz): δ 1.03 (s, 3H), 1.38-1.61 (m, 3H), 1.64-1.79 (m, 7H), 2.04-2.18 (m, 3H), 2.32 (s, 3H), 3.17-3.97 (m, 11H), 5.17 (s, 1H), 7.06-7.22 (m, 4H), 11.7 (s, 1H); MS: m/e 405.3 (M−18).

Example 51

(5aR,9bS)-3a-Hydroxy-3-((4-(2-methoxyphenyl)piperazin-1-yl)methyl)-5a,9-dimethyl-3,3a,4,5,5a,6,7,8-octahydronaphtho[1,2-b]furan-2(9bH)-one 1-(Methoxyphenyl)piperazine (464.5 mg, 2.42 mmol) and TEA (61.1 mg, 0.60 mmol) were added to the solution of compound of example 1 (500 mg, 2.016 mmol) in ethanol (10 mL). The reaction mixture was stirred at room temperature (25° C.) for 15 hours. The reaction mixture was concentrated and the crude product was purified by column chromatography (silica gel, 4% ethyl acetate in petroleum ether) to obtain the title compound.

Yield: 260 mg (29.31%); $^1$H NMR (CDCl$_3$, 300 MHz): δ 1.03 (s, 3H), 1.27-1.47 (m, 3H), 1.68-1.81 (m, 8H), 2.05-2.18 (m, 3H), 2.9-3.42 (m, 11H), 3.89 (s, 3H), 5.10 (s, 1H), 6.88-7.08 (m, 4H); MS m/e: 441 (M+1).

Example 52

(5aR,9bS)-3-((4-(2-Chlorophenyl)piperazin-1-yl)methyl)-3a-hydroxy-5a,9-dimethyl-3,3a,4,5,5a,6,7,8-octahydronaphtho[1,2-b]furan-2(9bH)-one The solution of compound of example 1 (300 mg, 1.21 mmol) and 1-(2-chloro-phenyl)-piperazine (284.5 mg, 1.45 mmol) in ethanol (5 mL) was stirred at room temperature (25° C.) for 15 hours. Reaction mixture was concentrated and crude product was purified by column chromatography (silica gel, 50% ethyl acetate in petroleum ether) to obtain the title compound.

Yield: 140 mg (26.06%); $^1$H NMR (CDCl$_3$, 300 MHz): δ 1.1 (s, 3H), 1.2-1.5 (m, 8H), 1.8 (s, 3H), 1.9-2.2 (m, 3H), 2.7-2.8 (m, 2H), 2.9-3.2 (m, 8H), 5.05 (s, 1H), 6.98-7.05 (m, 2H), 7.21-7.28 (m, 1H), 7.38 (d, 1H); MS: m/e 445 (M+1).

Example 53

(5aR,9bS)-3a-Hydroxy-5a,9-dimethyl-3-((4-(pyridin-2-yl)piperazin-1-yl)methyl)-3,3a,4,5,5a,6,7,8-octahydronaphtho[1,2-b]furan-2(9bH)-one The solution of compound of example 1 (248 mg, 1 mmol) and 1-(2-pyridyl)piperazine (179.5 mg, 1.1 mmol) in ethanol (5 mL) was stirred at room temperature (25° C.) for 15 hours and was concentrated. The crude product was purified by column chromatography (silica gel, 10% ethyl acetate in petroleum ether). The title compound was obtained by crystallization using ethyl acetate/petroleum ether.

Yield: 200 mg (48.66%); $^1$H NMR (CDCl$_3$, 300 MHz): δ 1.1 (s, 3H), 1.47-1.64 (m, 3H), 1.68-1.72 (m, 3H), 1.79 (m, 4H), 2.07-2.09 (m, 3H), 2.5-2.58 (m, 2H), 2.82-2.97 (m, 4H), 3.12-3.17 (m, 1H), 3.47-3.59 (m, 4H), 5.05 (s, 1H), 6.64-6.68 (m, 2H), 7.47-7.53 (m, 1H), 8.193-8.21 (m, 1H); MS: m/e 412.25 (M+1).

Example 54

(5aS,9bS)-3a-Hydroxy-3-((4-(((5aR,9bS)-3a-hydroxy-5a,9-dimethyl-2-oxo-2,3,3a,4,5,5a,6,7,8,9b-decahydronaphtho[1,2-b]furan-3-yl)methyl)piperazin-1-yl)methyl)-5a,9-dimethyl-3,3a,4,5,5a,6,7,8-octahydronaphtho[1,2-b]furan-2(9bH)-one The solution of compound of example 1 (300 mg, 1.209 mmol) and piperazine (114 mg, 1.33 mmol) in ethanol (5 mL) was stirred at room temperature (25° C.) for 2 hours. The reaction mixture was concentrated and crude product was purified by column chromatography (silica gel, 10% to 50% ethyl acetate in petroleum ether) to obtain the title compound.

Yield: 100 mg (14.19%); $^1$H NMR (CDCl$_3$, 300 MHz): δ 1.06 (s, 6H), 1.40-1.51 (m, 6H), 1.56-1.71 (m, 10H), 1.8 (bs, 8H), 1.91-2.42 (m, 8H), 2.78-2.92 (m, 8H), 3.05-3.10 (m, 2H), 5.03 (s, 2H); MS: m/e 583 (M+1).

Example 55

(5aS,9bR)-3a-Hydroxy-3-((((5aR,9bS)-3a-hydroxy-5a,9-dimethyl-2-oxo-2,3,3a,4,5,5a,6,7,8,9b-decahydronaphtho[1,2-b]furan-3-yl)methylamino)methyl)-5a,9-dimethyl-3,3a,4,5,5a,6,7,8-octahydronaphtho[1,2-b]furan-2(9bH)-one hydrochloride Step 1
(5aS,9bS)-3a-Hydroxy-3-((((5aR,9bS)-3a-hydroxy-5a,9-dimethyl-2-oxo-2,3,3a,4,5,5a,6,7,8,9b-decahydronaphtho[1,2-b]furan-3-yl)methylamino)methyl)-5a,9,9b-trimethyl-3,3a,4,5,5a,6,7,8-octahydronaphtho[1,2-b]furan-2(9bH)-one A solution of saturated ethanolic ammonia (0.5 mL) was added to the solution of compound of example 1 (500 mg, 2.016 mmol) in ethanol (5 mL). The reaction mixture was stirred at room temperature (25° C.) for 3 hours. The reaction mixture was concentrated and crude product was purified by column chromatography (silica gel, 5% methanol in chloroform) to obtain the title compound.

Yield: 190 mg (18.33%).

Step 2
Preparation of Hydrochloride

The compound obtained in step 1 (40 mg, 0.07 mmole) was dissolved in dry methanol (5 mL) and to it methanolic hydrochloric acid was added till pH was about 4. The reaction mixture was stirred at room temperature (25° C.) for 15 minutes and was concentrated. The hydrochloride was crystallized using methanol/dichloromethane to obtain the title compound.

Yield: 40 mg (93.45); $^1$H NMR (CDCl$_3$, 300 MHz): δ 0.86 (s, 6H), 1.22-1.33 (m, 8H), 1.50-1.53 (m, 8H), 1.64 (s, 8H), 1.91-1.99 (m, 5H), 3.29 (bs, 4H), 3.5 (bs, 2H), 4.96 (s, 2H), 9.65 (s, 1H); MS m/e 549 (M$^+$+HCl).

Example 56

N-(((5aR,9bS)-3a-Hydroxy-5a,9-dimethyl-2-oxo-2,3,3a,4,5,5a,6,7,8,9b-decahydronaphtho[1,2-b]furan-3-yl)methyl)-N-(((5aS,9bR)-3a-hydroxy-5a,9-dimethyl-2-oxo-2,3,3a,4,5,5a,6,7,8,9b-decahydronaphtho[1,2-b]furan-3-yl)methyl) acetamide The compound obtained in step 1 of example 55 (200 mg, 0.389 mmole) was dissolved in dry acetonitrile (4 mL) and to it acetic anhydride (43.78 mg, 0.426 mmole) and TEA (59.04 mg, 0.58 mmole) were added. The reaction mixture was stirred at room temperature (25° C.) for 2 hours. Reaction mixture was concentrated and crude product was purified by column chromatography (silica gel, 30% ethyl acetate in petroleum ether) to obtain the title compound.

Yield: 170 mg (78.70%); $^1$H NMR (CDCl$_3$, 300 MHz): δ 0.99 (s, 3H), 1.05 (s, 3H), 1.20-1.27 (m, 3H), 1.41-1.44 (m, 8H), 1.54-1.71 (m, 6H), 1.76 (s, 3H), 1.78 (s, 3H), 2.30 (s, 3H), 2.8 (s, 1H), 3.13 (m, 2H), 3.27 (dd, 2H), 3.53 (dd, 2H), 3.99-4.06 (m, 3H), 5.0 (s, 1H), 5.034 (s, 1H); MS: m/e 556.35 (M+1).

Example 57

3-Ethyl-1-(((5aR,9bS)-3a-hydroxy-5a,9-dimethyl-2-oxo-2,3,3a,4,5,5a,6,7,8,9b-decahydronaphtho[1,2-b]furan-3-yl)methyl)-1-(((5aS,9bR)-3a-hydroxy-5a,9-dimethyl-2-oxo-2,3,3a,4,5,5a,6,7,8,9b-decahydronaphtho[1,2-b]furan-3-yl)methyl)thiourea The compound obtained in step 1 of example 55 (200 mg, 0.389 mmole) was dissolved in dry tetrahydrofuran (10 mL) and to it ethyl isothiocyanate (54.22 mg, 0.62 mmole) was added dropwise. The reaction mixture was stirred at room temperature (25° C.) for 3 hours. Reaction mixture was concentrated and crude product was purified by column chromatography (silica gel, 20% ethyl acetate in petroleum ether) to obtain the title compound.

Yield: 100 mg (42.75%); $^1$H NMR (CDCl$_3$, 300 MHz): δ 1.00 (s, 6H), 1.22-1.29 (m, 8H), 1.38-1.44 (m, 8H), 1.62-1.65 (m, 6H), 1.77-1.80 (m, 10H), 2-07-2.15 (m, 4H), 3.21 (bs, 2H), 3.57-3.65 (m, 2H), 5.08 (s, 2H); MS: m/e 601 (M+1).

Example 58

Methyl 2-(((5aR,9bS)-3a-hydroxy-5a,9-dimethyl-2-oxo-2,3,3a,4,5,5a,6,7,8,9b-decahydronaphtho[1,2-b]furan-3-yl)methylamino)acetate TEA (182.14 mg, 1.8 mmole) was added to the solution of compound of example 1 (300 mg, 1.21 mmol) and glycine methyl ester hydrochloride (151 mg, 1.2 mmol) in ethanol (5 mL). The reaction mixture was stirred at room temperature (25° C.) for 15 hours and was concentrated and crude product was purified by column chromatography (silica gel, 2% methanol in chloroform) to obtain the title compound.

Yield: 220 mg (54%); $^1$H NMR (CDCl$_3$, 300 MHz): δ 1 (s, 3H), 1.3-1.74 (m, 8H), 1.8 (s, 3H), 1.83-1.94 (m, 2H), 2.08-2.18 (m, 2H), 2.96 (s, 2H), 3.21 (d, 1H), 3.47 (s, 2H), 3.75 (s, 3H), 5.01 (s, 1H); MS: m/e 338.19 (M+1).

Example 59

(5aR,9bS)-3a-Hydroxy-5a,9-dimethyl-3-(((2R)-2,4, 5-trihydroxy-6-(hydroxymethyl)tetrahydro-2H-pyran-3-ylamino)methyl)-3,3a,4,5,5a,6,7,8-octahydronaphtho[1,2-b]furan-2(9bH)-one α-D-Glucosamine hydrochloride (261 mg, 1.21 mmol) and TEA (159 mg, 1.57 mmol) were added to the solution of compound of example 1 (300 mg, 1.21 mmol) in ethanol (10 mL). The reaction mixture was stirred for 5 hours at room temperature (25° C.). The reaction mixture was concentrated, dried under vacuum. The title compound was obtained by washing the crude product with water followed by washing with diethyl ether.

Yield: 180 mg (34.83%); $^1$H NMR (CDCl$_3$, 300 MHz): δ 0.95 (s, 3H), 1.24-1.63 (m, 6H), 1.71 (s, 3H), 2.02 (bs, 2H), 2.04 (m, 1H), 2.2-2.3 (m, 1H), 2.29-2.50 (m, 4H), 2.89-3.12 (s, 3H), 3.47-3.64 (m, 3H), 4.93 (s, 1H), 5.28 (s, 2H); 6.17 (bs, 1H) MS: m/e 428 (M+1).

Example 60

(5aR,9bS)-3a-Hydroxy-3-(((2-hydroxy-2-(4-hydroxyphenyl)ethyl)(methyl)amino)methyl)-5a,9-dimethyl-3,3a,4,5,5a,6,7,8-octahydronaphtho[1,2-b]furan-2(9bH)-one dl-Synephrine (572 mg, 3.43 mmol) and TEA (122.27 mg, 1.21 mmol) were added to the solution of compound of example 1 (1000 mg, 4.03 mmol) in ethanol (20 mL), and reaction mixture was stirred at room temperature (25° C.) for 15 hours. The reaction mixture was concentrated, dried and was triturated with petroleum ether. The title compound was crystallized using ethyl acetate/petroleum ether system.

Yield: 275 mg (16.43%); $^1$H NMR (CDCl$_3$, 300 MHz): δ 0.96 (s, 3H), 1.16-1.61 (m, 7H), 1.72 (s, 3H), 1.82-2.4 (m, 6H), 2.31 (s, 3H), 2.49 (s, 3H), 4.49-4.76 (m, 1H), 4.95 (s, 1H), 5.08 (bs, 2H), 6.69 (d, 2H), 7.115 (d, 2H); MS: m/e: 416.2 (M+1).

Example 61

(5aR,9bS)-3a-hydroxy-3-(((2-hydroxy-2-(3-hydroxyphenyl)ethyl)(methyl)amino)methyl)-5a,9-dimethyl-3,3a,4,5,5a,6,7,8-octahydronaphtho[1,2-b]furan-2(9bH)-one L(−)Phenylephrine hydrochloride (689.2 mg, 3.38 mmol) was added to the solution of compound of example 1 (700 mg, 2.82 mmol) in ethanol (20 mL), and TEA (427.2 mg, 4.23 mmol) was added and reaction mixture was stirred at room temperature (25° C.) for 15 hours. The reaction mixture was concentrated and crude product was purified by column chromatography (silica gel, 10% ethyl acetate in petroleum ether) to obtain the title compound.

(Yield: 250 mg; 21.3%); $^1$H NMR (CDCl$_3$, 300 MHz): δ 0.96 (s, 3H), 1.0-1.5 (m, 10H), 1.70 (s, 3H), 1.94-3.11 (m, 8H), 4.57-4.59 (m, 1H), 4.93 (s, 1H), 5.07-5.17 (m, 1H), 6.58-6.61 (m, 1H), 6.71-6.75 (m, 2H), 7.04-7.09 (m, 1H), 9.1-9.5 (broad s, 1H); MS m/e: 416.2 (M+1).

Example 62

4-(1-Acetoxy-2-((((5aR,9bS)-3a-hydroxy-5a,9-dimethyl-2-oxo-2,3,3a,4,5,5a,6,7,8,9b-decahydronaphtho[1,2-b]furan-3-yl)methyl)(methyl)amino)ethyl) phenyl acetate Step 1 dl-Synephrine (465 mg, 2.76 mmol) and TEA (97.7 mg, 0.968 mmol) were added to the solution of compound of example 1 (800 mg, 3.23 mmol) in ethanol (20 mL). The reaction mixture was stirred at room temperature (25° C.) for 15 hours. The reaction mixture was concentrated and the crude product was subjected directly for acetylation reaction as in step 2.

Step 2

Crude product obtained in step 1 (850 mg, 2.05 mmol) was dissolved in dichloromethane (15 mL) and to it pyridine (405 mg, 5.12 mmol) and acetic anhydride (418 mg, 4.1 mmol) and 4-(dimethylamino)pyridine (DMAP) (1 mg) were added and reaction mixture was stirred at room temperature (25° C.) for 15 hours. The reaction mixture was concentrated and the crude product was purified by column chromatography (Silica gel, 4% ethyl acetate in petroleum ether). The title compound was obtained by crystallization using ethyl acetate/petroleum ether.

Yield: 120 mg (11.74%); $^1$H NMR (CDCl$_3$, 300 MHz): δ 1.04 (s, 3H), 1.42-1.51 (m, 7H), 1.57-1.75 (m, 4H) 1.76-1.81 (m, 5H), 2.06-2.18 (m, 5H), 2.31 (s, 3H), 2.49 (s, 3H), 2.78 (d, 1H,), 5.03 (s, 1H), 5.99-6.02 (dd, 1H), 7.09-7.12 (d, 2H), 7.35-7.38 (d, 2H); MS m/e: 500.1 (M+1).

Pharmacology

The efficacy of the compounds of formula 1 and formulations, in inhibiting the activity of TNF-α and interleukins (IL-1β, IL-6 and IL-8) was determined by pharmacological assays well known in the art and described below.

In Vitro Screening to Identify Inhibitors of TNF-α, IL-1β, IL-6 and IL-8

Example 63

Primary Screening—Human Peripheral Blood Mononuclear Cells (hPBMCs)

TNF-α production by lipopolysaccharides (LPS) in hPBMCs was measured according to the method described by Jansky, L. et al (Physiol. Res. 52: 593-598, 2003), incorporated herein by reference. Blood was collected from healthy donors into Potassium EDTA vacutainer tubes (BD vacutainer). The PBMCs were isolated using gradient centrifugation in Histopaque-1077 solution (Sigma). Isolated PBMCs were suspended in RPMI 1640 culture medium (Gibco BRL, Pasley, UK) containing 10% fetal bovine serum (FBS) (Hyclone, Utah, USA), 100 U/ml penicillin (Sigma Chemical Co. St Louis, Mo.) and 100 μg/ml streptomycin (Sigma Chemical Co. St Louis, Mo.). The cell concentration was adjusted to 1×10$^6$ cells/mL. The viability as determined by trypan blue dye exclusion was uniformly ≥98%. The cell suspension (100 μL) was added to the wells of a 96-well culture plate. Following cell plating, 79 μL of the culture medium and 1 μL of eight different concentrations of the test compounds (final concentration 0.03, 0.1, 0.3, 1, 3, 10, 30, 100 μM) dissolved in DMSO (dimethylsulfoxide, Sigma, Mo., USA) were added to the cells. The final concentration of DMSO was adjusted to 0.5%. The vehicle (0.5% DMSO) was used as control. Rolipram (30, 100 μM) was used as a standard compound. The plates were incubated for 30 min at 37° C. in an atmosphere of 5% CO$_2$. Finally, 20 μL (10 μg/mL) per well of LPS, (*Escherchia coli* 0127:B8, Sigma Chemical Co., St. Louis, Mo.) was added, for a final concentration of 1 μg/mL. The plates were incubated at 37° C. for 5 hours in an atmosphere of 5% CO$_2$. To assess the cytotoxic effect of the test compounds, the cellular viability test was performed using MTS (3-(4,5-dimethylthiazol-2-yl)-5-(3-carboxymethoxyphenyl)-2-(4-sulfonyl)-2H-tetrazolium) reagent after 5 hours of incubation. Supernatants were harvested and assayed for TNF-α, IL-1β, IL-6 and IL-8 by ELISA as described by the manufacturer. (OptiEIA ELISA sets, BD Biosciences, Pharmingen). The 50% inhibitory concentration (IC$_{50}$) values were calculated by a nonlinear regression method using GraphPad software (Prism 3.03)

Conclusion: Certain compounds of the present invention were found to inhibit proinflammatory cytokines such as TNF-α and/or interleukins such as IL-1β, IL-6 and, IL-8), released by LPS-stimulated hPBMCs. (Table 1 and Table 2)

TABLE 1

TNF-α inhibition in Human peripheral blood mononuclear cells
IC$_{50}$ values are in μM

| Sr. No. | Compound | IC$_{50}$ |
|---|---|---|
| 01 | Compound of example 3 | 0.5 |
| 02 | Compound of example 17 | 0.7 |
| 03 | Compound of example 18 | 0.4 |
| 05 | Compound of example 22 | 0.7 |
| 06 | Compound of example 25 | 3.3 |
| 07 | Compound of example 27 | 0.3 |
| 08 | Compound of example 30 | 0.8 |
| 09 | Compound of example 33 | 0.3 |
| 10 | Compound of example 36 | 1.1 |
| 11 | Compound of example 38 | 0.8 |
| 12 | Compound of example 48 | 0.7 |
| 13 | Compound of example 53 | 0.8 |
| 14 | Compound of example 54 | 0.6 |
| 15 | Compound of example 55 | 1.2 |
| 16 | Compound of example 58 | 2.0 |
| 17 | Compound of example 59 | 0.4 |
| 18 | Compound of example 60 | 0.2 |

TABLE 2

IC$_{50}$ values for Proinflammatory cytokines released by
LPS-stimulated hPBMCs (IL-1β, IL-6 and IL-8)
IC$_{50}$ values are in μM

| Sr. No. | Compound | IL-1β | IL-6 | IL-8 |
|---|---|---|---|---|
| 01 | Compound of example 17 | 0.26 | 3 | 27.6 |
| 02 | Compound of example 18 | 0.2 | 0.9 | 9.2 |
| 03 | Compound of example 54 | 0.2 | 2.1 | 11.7 |
| 04 | Compound of example 55 | 0.31 | 3.1 | 29 |

In Vivo Assay

Example 64

Lipopolysaccharide (LPS)-Induced Tumor Necrosis Factor (TNF)-α Release in BALB/c Mice The assay was designed as in reference, J. Med. Bio. Res., 1997, 30, 1199-1207, the disclosure of which is incorporated by reference for the teaching of the assay.

Protocol:

Balb/c mice of either sex weighing between 18-22 g were orally administered test compound at doses of 12.5, 50, 75, 100 mg/kg. All suspensions were freshly prepared in 0.5% CMC. One hour later, LPS (1 mg/kg) (*Escherichia coli*, serotype 0127:B8, Sigma Chemical Co., St. Louis, Mo.) dissolved in sterile pyrogen-free saline was administered intraperitoneally to the control group, standard treatment group (Rolipram, 30 mg/kg, p.o.) and test groups except the negative control group, which received normal saline.

Blood samples were collected from anesthetized mice, with heparin as an anti-coagulant (25 IU per sample) 1.5 hours post LPS challenge. These were then centrifuged at 10000 rpm for 10 minutes and plasma samples were analysed for levels of TNF-α by ELISA, as described by the manufacturer (OptiEIA ELISA sets, BD BioSciences Pharmingen).

Percent inhibition of TNF-α release was calculated by comparing the TNF-α levels of the treatment groups with those of the control group.

CONCLUSION

Exemplary compounds of the present invention exhibited 30-98% inhibition of LPS-induced TNF-α release in Balb/c mice at a dose of 100 mg/Kg

We claim:

1. A compound of formula 1 or a pharmaceutically acceptable salt thereof,

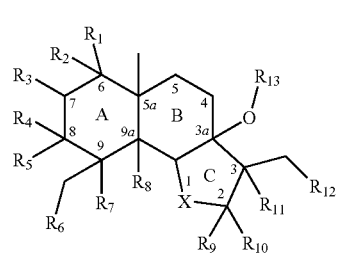

Formula 1 wherein
$R_1$, $R_2$ and $R_3$ are each independently selected from hydrogen, alkyl, halogen, hydroxy, alkoxy, —OC(O)$R_{14}$, and —C(O)$R_{14}$;
optionally $R_1$ is absent and $R_2$ is =O;
$R_4$ and $R_5$ are each independently selected from hydrogen, alkyl, and halogen;
ring A optionally contains one or two double bonds;
$R_5$ is absent when a double bond is formed between carbon numbers 7 and 8;
$R_6$ is selected from hydrogen, alkyl, cycloalkyl, halogen, hydroxy, alkoxy, —OC(O)$R_{14}$, —C(O)$R_{14}$ and —NR$_{15}$R$_{16}$;
$R_7$ and $R_8$ are each hydrogen or may together form an optionally substituted ring, which optionally contains a heteroatom; $R_7$ and $R_8$ are absent when a double bond is formed between carbon numbers 9 and 9a;
ring C optionally contains one double bond between X and carbon number 2;
$R_9$ is absent when the double bond is formed between X and carbon number 2;
$R_9$ and $R_{10}$ are each independently selected from hydrogen, alkyl, halogen, —OR$_{13}$, NHR$_{14}$ and SR$_{14}$; or
$R_9$ is absent and $R_{10}$ is selected from =O;
$R_{11}$ is selected from hydrogen, hydroxy, and alkoxy;
$R_{12}$ is selected from cycloalkyl, aryl, heterocyclyl, —OC(O)$R_{14}$, —C(O)$R_{14}$, azido, —NR$_{15}$R$_{16}$, —S(O)$_m$R$_{17}$, and —OS(O)$_m$R$_{17}$;
X is O;
$R_{13}$ is selected from hydrogen, alkyl and —C(O)$R_{14}$;
$R_{14}$ is substituted alkyl;
$R_{15}$ and $R_{16}$ are each independently selected from hydrogen, alkyl, cycloalkyl, aralkyl, aryl, heterocyclyl, C(O)$R_{14}$ and —C(S)—NHR$_{14}$; or $R_{15}$ and $R_{16}$, together with the N atom to which they are bonded, form a 5-, 6-, or 7-membered heterocyclic ring, optionally having one or more additional heteroatoms selected from: O, N and S;

$R_{17}$ is selected from hydrogen, alkyl, cycloalkyl, aryl and heterocyclyl;

m is an integer from 0 to 2;

where alkyl or cycloalkyl are unsubstituted or substituted by one or two of the same or different groups selected from: alkyl, cycloalkyl, aralkyl, trifluoromethyl, halogen, carboxy, acetoxy, alkoxy, aryloxy, aryl and heterocyclyl;

aryl is unsubstituted or substituted by one or two of the same or different groups selected from: alkyl, trifluoromethyl, hydroxy, alkoxy, halogen, nitro and amino;

heterocyclyl is unsubstituted or substituted by one or two of the same or different groups selected from: alkyl, cycloalkyl, trifluoromethyl, halogen, hydroxy, alkoxy, oxo, amino and aryl;

halogen is selected from fluorine, chlorine, bromine and iodine;

with the proviso that when $R_1$, $R_2$, $R_3$, $R_4$, $R_5$ and $R_6$ are each hydrogen atoms; ring A contains one double bond formed between carbon numbers 9 and 9a, and $R_7$ and $R_8$ are absent; $R_9$ is absent and $R_{10}$ is =O; $R_{11}$ is hydrogen, $R_{12}$ is —$NR_{15}R_{16}$; $R_{13}$ is hydrogen; X is O; then $R_{15}$ and $R_{16}$ together with the N atom to which they are bonded do not form an unsubstituted piperidine ring or unsubstituted morpholine ring.

2. A compound according to claim 1 or a pharmaceutically acceptable salt thereof, wherein $R_1$, $R_2$, $R_3$, $R_4$, $R_5$ and $R_6$ are each hydrogen;

ring A contains one double bond formed between carbon numbers 9 and 9a, and $R_7$ and $R_8$ are absent;

$R_9$ is absent and $R_{10}$ is =O;

$R_{11}$ is hydrogen;

$R_{12}$ is selected from cycloalkyl, aryl, heterocyclyl, —OC(O)$R_{14}$, —C(O)$R_{14}$, azido, —$NR_{15}R_{16}$, —S(O)$_m R_{17}$, and —OS(O)$_m R_{17}$;

$R_{13}$ is selected from hydrogen, alkyl, and —C(O)$R_{14}$;

$R_{14}$ is substituted alkyl;

$R_{15}$ and $R_{16}$ are each independently selected from hydrogen, alkyl, cycloalkyl, aralkyl, aryl, heterocyclyl, —C(O)$R_{14}$, and C(S)—$NHR_{14}$; or $R_{15}$ and $R_{16}$, together with the N atom to which they are bonded, form a 5-, 6-, or 7-membered heterocyclic ring, optionally having one or more additional heteroatoms selected from: O, N and S;

$R_{17}$ is selected from hydrogen, alkyl, cycloalkyl, aryl and heterocyclyl;

m is an integer from 0 to 2;

where alkyl or cycloalkyl are unsubstituted or substituted by one or two of the same or different groups selected from: alkyl, cycloalkyl, aralkyl, trifluoromethyl, halogen, carboxy, acetoxy, alkoxy, aryloxy, aryl and heterocyclyl;

aryl is unsubstituted or substituted by one or two of the same or different groups selected from: alkyl, trifluoromethyl, hydroxy, alkoxy, halogen, nitro and amino;

heterocyclyl is unsubstituted or substituted by one or two of the same or different groups selected from: alkyl, cycloalkyl, trifluoromethyl, halogen, hydroxy, alkoxy, oxo, amino and aryl; halogen is selected from fluorine, chlorine, bromine and iodine;

with the proviso that when $R_{12}$ is —$NR_{15}R_{16}$; $R_{13}$ is hydrogen; X is O; then $R_{15}$ and $R_{16}$ together with the N atom to which they are bonded do not form unsubstituted piperidine or unsubstituted morpholine ring.

3. A compound according to claim 2, or a pharmaceutically acceptable salt thereof, wherein $R_1$, $R_2$, $R_3$, $R_4$, $R_5$ and $R_6$ are each hydrogen;

ring A contains one double bond formed between carbon numbers 9 and 9a; and $R_7$ and $R_8$ are absent;

$R_9$ is absent and $R_{10}$ is =O;

$R_{11}$ is hydrogen;

$R_{12}$ is selected from cycloalkyl, —OC(O)$R_{14}$, —C(O)$R_{14}$, —$NR_{15}R_{16}$, aryl and heterocyclyl;

$R_{13}$ is hydrogen;

$R_{14}$ is substituted alkyl;

$R_{15}$ and $R_{16}$ are each independently selected from hydrogen, alkyl, cycloalkyl, aralkyl, aryl, heterocyclyl, —C(O)$R_{14}$, and C(S)—$NHR_{14}$; or $R_{15}$ and $R_{16}$, together with the N atom to which they are bonded, form a 5-, 6-, or 7-membered heterocyclic ring, optionally having one or more additional heteroatoms selected from: O, N and S;

where alkyl or cycloalkyl are unsubstituted or substituted by one or two of the same or different groups selected from: alkyl, cycloalkyl, aralkyl, trifluoromethyl, halogen, carboxy, acetoxy, alkoxy, aryloxy, aryl and heterocyclyl;

aryl is unsubstituted or substituted by one or two of the same or different groups selected from: alkyl, trifluoromethyl, hydroxy, alkoxy, halogen, nitro and amino; and heterocyclyl is unsubstituted or substituted by one or two of the same or different groups selected from: alkyl, cycloalkyl, trifluoromethyl, halogen, hydroxy, alkoxy, oxo, amino and aryl;

with the proviso that, when $R_{12}$ is —$NR_{15}R_{16}$; then $R_{15}$ and $R_{16}$ together with the N atom to which they are bonded do not form a unsubstituted piperidine or unsubstituted morpholine ring.

4. A compound according to claim 3, or a pharmaceutically acceptable salt thereof, wherein $R_{12}$ is —$NR_{15}R_{16}$;

$R_{15}$ and $R_{16}$, together with the N atom to which they are bonded, form a 5-, 6- or 7-membered heterocyclyl, optionally having one or more additional heteroatoms selected from: O, N and S;

wherein the heterocyclyl is selected from unsubstituted or substituted pyrrolyl, imidazolyl, oxazolyl, isoxazolyl, thiazolyl, isothiazolyl, triazolyl, tetrazolyl, pyrazolyl, pyridinyl, pyrazinyl, pyridazinyl, pyrimidinyl, azepinyl, diazepinyl, triazepinyl, thiomorpholinyl, tetrahydropyranyl, lactam, pyrrolidinyl, azetidinyl, piperazinyl, substituted morpholinyl, and substituted piperidinyl.

5. A compound according to claim 4, or a pharmaceutically acceptable salt thereof, wherein $R_9$ is absent and $R_{10}$ is =O; and $R_{12}$ is selected from 1H-pyrazol-1-yl, 3,5-dimethyl-1H-pyrazol-1-yl, 2-methyl-1H-imidazol-1-yl, 1H-1,2,4-triazol-1-yl, 2-carboxy-pyrrolidin-1-yl, 4-oxo-piperidin-1-yl, 4-hydroxy piperidin-1-yl, 1,4'-bipiperidin-1-yl, thiomorpholin-4-yl, and 1-oxo-thiomorpholin-4-yl.

6. A compound according to claim 3, or a pharmaceutically acceptable salt thereof, wherein $R_{12}$ is unsubstituted or substituted piperazinyl.

7. A compound according to claim 6, or a pharmaceutically acceptable salt thereof, wherein $R_{12}$ is selected from piperazin-1-yl, 4-methylpiperazin-1-yl, 4-benzylpiperazin-1-yl, 4-(2,6-dimethylbenzyl)piperazin-1-yl, 4-(3,5-dimethoxy-2-methylbenzyl)piperazin-1-yl, 4-(2-(hydroxymethyl)-3,5-dimethoxy-6-methylbenzyl)-piperazin-1-yl, 4-(2-fluorobenzyl)piperazin-1-yl, 4-(perfluorobenzyl)piperazin-1-yl, 4-(2-chloro-6-fluorobenzyl)piperazin-1-yl, 4-(2-fluoro-6-(trifluoromethyl)benzyl)piperazin-1-yl, 4-(benzo[d][1,3]dioxol-4-ylmethyl)piperazin-1-yl, 4-(2-(hydroxymethyl)-3,5-dimethoxybenzyl)piperazin-1-yl, 4-phenethyl piperazin-1-yl, 4-acetylpiperazin-1-yl, 4-phenylpiperazin-1-yl, 4-o-tolylpiperazin-1-yl, 4-(2-methoxyphenyl)piperazin-1-yl, 4-(2-chlorophenyl)piperazin-1-yl, 4-(pyridin-2-yl)piperazin-1-yl, and groups of the formula:

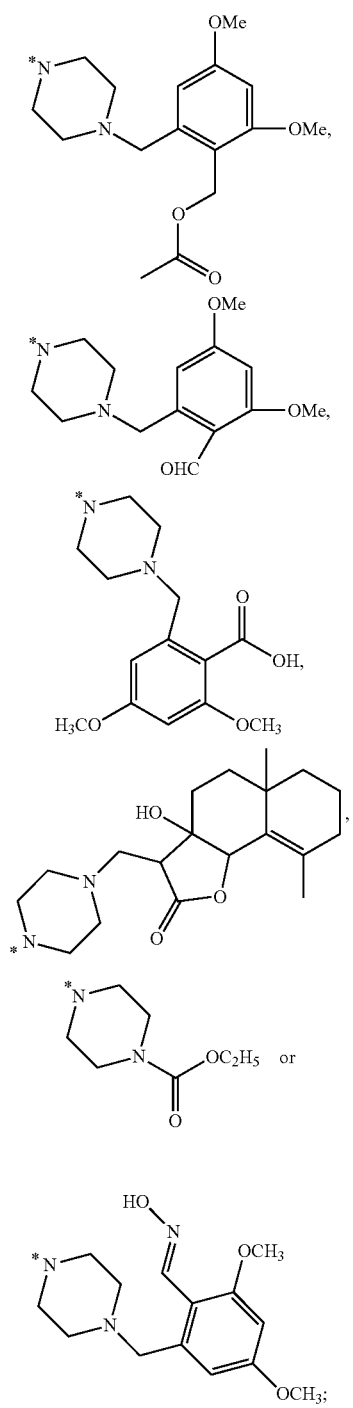

* indicates point of attachment.

8. A compound according to claim 1, or a pharmaceutically acceptable salt thereof, wherein
$R_1$, $R_2$, $R_3$, $R_4$, $R_5$ and $R_6$ are each hydrogen;
ring A contains one double bond formed between carbon numbers 9 and 9a, and $R_7$ and $R_8$ are absent;
$R_9$ is absent and $R_{10}$ is =O;
$R_{11}$ is hydrogen;
$R_{12}$ is —$NR_{15}R_{16}$;
$R_{13}$ is hydrogen;
$R_{15}$ is selected from hydrogen and alkyl;
$R_{16}$ is selected from unsubstituted or substituted alkyl, cycloalkyl, aralkyl and aryl;
where alkyl or cycloalkyl are unsubstituted or substituted by one or two of the same or different groups selected from: alkyl, cycloalkyl, aralkyl, trifluoromethyl, halogen, carboxy, acetoxy, alkoxy, aryloxy, aryl and heterocyclyl;
aryl is unsubstituted or substituted by one or two of the same or different groups selected from: alkyl, trifluoromethyl, hydroxy, alkoxy, halogen, nitro and amino; and
heterocyclyl is unsubstituted or substituted by one or two of the same or different groups selected from: alkyl, cycloalkyl, trifluoromethyl, halogen, hydroxy, alkoxy, oxo, amino and aryl.

9. A compound according to claim 8, or a pharmaceutically acceptable salt thereof, wherein
$R_{12}$ is —$NR_{15}R_{16}$;
$R_{15}$ is selected from hydrogen and methyl; and
$R_{16}$ is selected from the groups of formula:

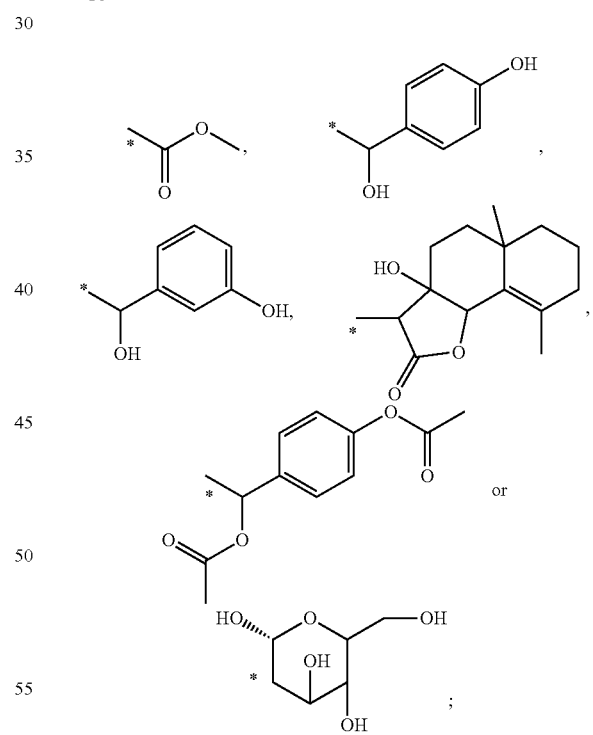

* indicates point of attachment.

10. A compound according to claim 1, or a pharmaceutically acceptable salt thereof, wherein
$R_1$, $R_2$, $R_3$, $R_4$, $R_5$ and $R_6$ are each hydrogen;
ring A contains one double bond formed between carbon numbers 9 and 9a, and $R_7$ and $R_8$ are absent;
$R_9$ is absent and $R_{10}$ is =O;
$R_{11}$ is hydrogen;
$R_{12}$ is —$NR_{15}R_{16}$;
$R_{13}$ is hydrogen;

$R_{14}$ substituted alkyl;
$R_{15}$ is selected from alkyl, —C(O)$R_{14}$ or —C(S)—NH$R_{14}$; and
$R_{16}$ is a group of formula:

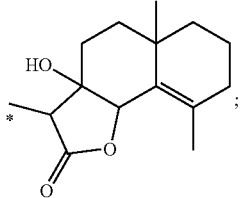

* indicates point of attachment.

11. A compound according to 10, or a pharmaceutically acceptable salt thereof, wherein
$R_{12}$ is —N$R_{15}R_{16}$;
$R_{15}$ is selected from —C(O)CH$_3$ or —C(S)—NHCH$_2$CH$_3$; and
$R_{16}$ is a group of formula:

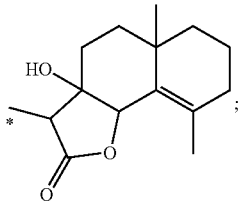

* indicates point of attachment.

12. A compound according to claim 1, or a pharmaceutically acceptable salt thereof, wherein
$R_1$, $R_2$, $R_3$, $R_4$, $R_5$ and $R_6$ are each hydrogen;
ring A contains one double bond formed between carbon numbers 9 and 9a, and $R_7$ and $R_8$ are absent;
$R_9$ is absent and $R_{10}$ is =O;
$R_{11}$ is hydrogen;
$R_{12}$ is —S(O)$_m R_{17}$;
$R_{13}$ is hydrogen;
$R_{17}$ is selected from hydrogen, alkyl, cycloalkyl, aryl and heterocyclyl;
m is an integer from 0 to 2;
where alkyl or cycloalkyl are unsubstituted or substituted by one or two of the same or different groups selected from: alkyl, cycloalkyl, aralkyl, trifluoromethyl, halogen, carboxy, acetoxy, alkoxy, aryloxy, aryl and heterocyclyl;
aryl is unsubstituted or substituted by one or two of the same or different groups selected from: alkyl, trifluoromethyl, hydroxy, alkoxy, halogen, nitro and amino; and
heterocyclyl is unsubstituted or substituted by one or two of the same or different groups selected from: alkyl, cycloalkyl, trifluoromethyl, halogen, hydroxy, alkoxy, oxo, amino and aryl.

13. A compound according to claim 12, or a pharmaceutically acceptable salt thereof, wherein
$R_{12}$ is selected from —S—CH$_2$COOH and —S—C$_6$H$_5$.

14. A compound according to claim 1, or a pharmaceutically acceptable salt thereof, wherein
$R_1$, $R_2$, $R_3$, $R_4$, $R_5$ and $R_6$ are each hydrogen;
$R_7$ and $R_8$ together form an optionally substituted ring, which optionally contains a heteroatom;
$R_9$ is absent and $R_{10}$ is =O;
$R_{11}$ is hydrogen;
$R_{12}$ is —N$R_{15}R_{16}$;
$R_{13}$ is hydrogen;
$R_{15}$ and $R_{16}$ are each independently selected from hydrogen, alkyl, cycloalkyl, aralkyl, aryl or heterocyclyl, or $R_{15}$ and $R_{16}$, together with the N atom to which they are bonded, form a 5-, 6- or 7-membered heterocyclyl, optionally having one or more additional heteroatoms selected from: O, N and S, wherein the heterocyclyl group is selected from unsubstituted or substituted pyrrolyl, pyrazolyl, pyrazinyl, morpholinyl, thiomorpholinyl, pyrrolidinyl, piperidinyl and piperazinyl;
where alkyl or cycloalkyl are unsubstituted or substituted by one or two of the same or different groups selected from: alkyl, cycloalkyl, aralkyl, trifluoromethyl, halogen, carboxy, acetoxy, alkoxy, aryloxy, aryl and heterocyclyl; and
aryl is unsubstituted or substituted by one or two of the same or different groups selected from: alkyl, trifluoromethyl, hydroxy, alkoxy, halogen, nitro and amino.

15. A compound according to 14, or a pharmaceutically acceptable salt thereof, wherein
$R_7$ and $R_8$ together form an optionally substituted ring which contains an oxygen atom;
$R_{15}$ and $R_{16}$ are each independently selected from hydrogen, alkyl, cycloalkyl, aralkyl, aryl or heterocyclyl, or $R_{15}$ and $R_{16}$, together with the N atom to which they are bonded, form a 5-, 6- or 7-membered heterocyclyl, optionally having one or more additional heteroatoms selected from: O, N and S, wherein the heterocyclyl group is selected from unsubstituted or substituted pyrrolyl, pyrazolyl, pyrazinyl, morpholinyl, thiomorpholinyl, pyrrolidinyl, piperidinyl and piperazinyl where alkyl or cycloalkyl are unsubstituted or substituted by one or two of the same or different groups selected from: alkyl, cycloalkyl, aralkyl, trifluoromethyl, halogen, carboxy, acetoxy, alkoxy, aryloxy, aryl and heterocyclyl; and
aryl is unsubstituted or substituted by one or two of the same or different groups selected from: alkyl, trifluoromethyl, hydroxy, alkoxy, halogen, nitro and amino.

16. A compound according to 15, or a pharmaceutically acceptable salt thereof, wherein
$R_7$ and $R_8$ together form an epoxide ring;
$R_{11}$ is hydrogen; and
$R_{12}$ is piperidinyl.

17. A compound according to claim 1, or a pharmaceutically acceptable salt thereof, wherein
$R_1$, $R_2$, $R_3$, $R_4$, $R_5$ and $R_6$ are each hydrogen;
ring A contains a double bond formed between carbon numbers 9 and 9a, and $R_7$ and $R_8$ are absent;
R$_9$ is absent and $R_{10}$ is =O;
$R_{11}$ is hydroxy;
$R_{12}$ is selected from cycloalkyl, aryl, heterocyclyl, —OC(O)$R_{14}$, —C(O)$R_{14}$, azido, —N$R_{15}R_{16}$, —S(O)$_m R_{17}$, and —OS(O)$_m R_{17}$;
$R_{13}$ is hydrogen;
$R_{14}$ is substituted alkyl;
$R_{15}$ and $R_{16}$ are each independently selected from hydrogen, alkyl, cycloalkyl, aralkyl, aryl, heterocyclyl, —C(O)$R_{14}$ and —C(S)—NH$R_{14}$; or $R_{15}$ and $R_{16}$, together with the N atom to which they are bonded, form a 5-, 6-, or 7-membered heterocyclic ring, optionally having one or more additional heteroatoms selected from: O, N and S;

$R_{17}$ is selected from hydrogen, alkyl, cycloalkyl, aryl and heterocyclyl;

m is an integer from 0 to 2 where alkyl or cycloalkyl are unsubstituted or substituted by one or two of the same or different groups selected from: alkyl, cycloalkyl, aralkyl, trifluoromethyl, halogen, carboxy, acetoxy, alkoxy, aryloxy, aryl and heterocyclyl;

aryl is unsubstituted or substituted by one or two of the same or different groups selected from: alkyl, trifluoromethyl, hydroxy, alkoxy, halogen, nitro and amino, and heterocyclyl is unsubstituted or substituted by one or two of the same or different groups selected from: alkyl, cycloalkyl, trifluoromethyl, halogen, hydroxy, alkoxy, oxo, amino and aryl.

18. A compound according claim 17, or a pharmaceutically acceptable salt thereof, wherein, $R_1$, $R_2$, $R_3$, $R_4$, $R_5$ and $R_6$ are each hydrogen; and $R_{12}$ is selected from —OS(O)$_2$—C$_6$H$_5$-4-CH$_3$, azido, piperazin-1-yl, and a group of formula:

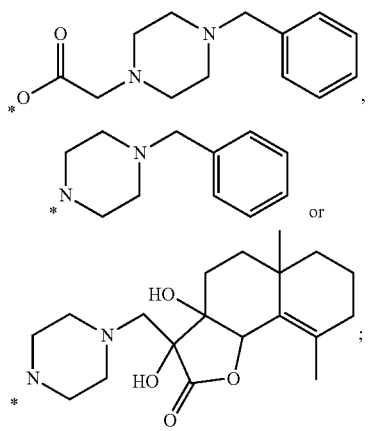

* indicates point of attachment.

19. A compound according to claim 1, or a pharmaceutically acceptable salt thereof, wherein $R_1$, $R_2$, $R_3$, $R_4$, $R_3$, $R_6$, $R_7$ and $R_8$ are each hydrogen;

$R_9$ is absent and $R_{10}$ is =O;

$R_{11}$ is hydrogen;

$R_{12}$ is —NR$_{15}$R$_{16}$;

$R_{13}$ is hydrogen; and $R_{15}$ and $R_{16}$, together with the N atom to which they are bonded, form a 5-, 6- or 7-membered heterocyclyl, optionally having one or more additional heteroatoms selected from: O, N and S;

wherein the heterocyclyl is selected from unsubstituted or substituted pyrrolyl, imidazolyl, oxazolyl, isoxazolyl, thiazolyl, isothiazolyl, triazolyl, tetrazolyl, pyrazolyl, pyridinyl, pyrazinyl, pyridazinyl, pyrimidinyl, azepinyl, diazepinyl, triazepinyl, thiomorpholinyl, tetrahydropyranyl, lactam, pyrrolidinyl, azetidinyl, piperazinyl, morpholinyl, and piperidinyl.

20. A compound according to claim 19, or a pharmaceutically acceptable salt thereof, wherein $R_{12}$ is selected from piperazinyl and morpholinyl.

21. A compound according to claim 1, or a pharmaceutically acceptable salt thereof, wherein $R_1$, $R_2$, $R_3$, $R_4$, $R_5$ and $R_6$ are each hydrogen;

ring A contains a double bond is formed between carbon numbers 9 and 9a, and $R_7$ and $R_8$ are absent;

$R_9$ is hydrogen and $R_{10}$ is selected from hydrogen, hydroxy and —OC(O)R$_{14}$;

$R_{11}$ is hydrogen;

$R_{12}$ is —NR$_{15}$R$_{16}$;

$R_{13}$ is hydrogen;

$R_{14}$ is substituted alkyl; and $R_{15}$ and $R_{16}$, together with the N atom to which they are bonded, form a 5-, 6- or 7-membered heterocyclyl, optionally having one or more additional heteroatoms selected from: O, N and S;

wherein the heterocyclyl is selected from unsubstituted or substituted pyrrolyl, imidazolyl, oxazolyl, isoxazolyl, thiazolyl, isothiazolyl, triazolyl, tetrazolyl, pyrazolyl, pyridinyl, pyrazinyl, pyridazinyl, pyrimidinyl, azepinyl, diazepinyl, triazepinyl, thiomorpholinyl, tetrahydropyranyl, lactam, pyrrolidinyl, azetidinyl, piperazinyl, substituted morpholinyl and substituted piperidinyl.

22. A compound according to claim 21, or a pharmaceutically acceptable salt thereof, wherein $R_{12}$ is substituted piperazinyl.

23. A compound according to claim 1, wherein the compound is:

((5aR,9bS)-3,3a-Dihydroxy-5a,9-dimethyl-2-oxo-2,3,3a, 4,5,5a,6,7,8,9b-decahydro naphtho[1,2-b]furan-3-yl) methyl-4-methylbenzenesulfonate;

(5aR,9bS)-3-(Azidomethyl)-3,3a-dihydroxy-5a,9-dimethyl-3,3a,4,5,5a,6,7,8-octahydro naphtho[1,2-b]furan-2(9bH)-one;

(5aR,9bS)-3,3a-Dihydroxy-5a,9-dimethyl-3-(piperidin-1-ylmethyl)-3,3a,4,5,5a,6,7,8-octahydronaphtho[1,2-b] furan-2(9bH)-one;

(5aR,9bS)-3-((4-Benzylpiperazin-1-yl)methyl)-3,3a-dihydroxy-5a,9-dimethyl-3,3a,4,5,5a,6,7,8-octahydronaphtho[1,2-b]furan-2(9bH)-one;

(5aR,9bS)-3-((4-(((5aR,9bS)-3,3a-dihydroxy-5a,9-dimethyl-2-oxo-2,3,3a,4,5,5a,6,7,8,9b-decahydronaphtho [1,2-b]furan-3-yl)methyl)piperazin-1-yl)methyl)-3,3a-dihydroxy-5a,9-dimethyl-3,3a,4,5,5a,6,7,8-octahydronaphtho[1,2-b]furan-2(9bH)-one;

(5aR,9bS)-3a-Hydroxy-5a,9-dimethyl-3-(phenylthiomethyl)-3,3a,4,5,5a,6,7,8-octahydro naphtho[1,2-b]furan-2(9bH)-one;

2-(((5aR,9bS)-3a-Hydroxy-5a,9-dimethyl-2-oxo-2,3,3a, 4,5,5a,6,7,8,9b-decahydro naphtho[1,2-b]furan-3-yl) methylthio)acetic acid;

(5aR,9bS)-3-((1H-Pyrazol-1-yl)methyl)-3a-hydroxy-5a, 9-dimethyl-3,3a,4,5,5a,6,7,8-octahydronaphtho[1,2-b] furan-2(9bH)-one;

(5aR,9bS)-3-((3,5-Dimethyl-1H-pyrazol-1-yl)methyl)-3a-hydroxy-5a,9-dimethyl-3,3a,4,5,5a,6,7,8-octahydronaphtho[1,2-b]furan-2(9bH)-one;

(5aR,9bS)-3a-Hydroxy-5a,9-dimethyl-3-((2-methyl-1H-imidazol-1-yl)methyl)-3,3a,4,5,5a,6,7,8-octahydronaphtho[1,2-b]furan-2(9bH)-one;

(5aR,9bS)-3-((1H-1,2,4-Triazol-1-yl)methyl)-3a-hydroxy-5a,9-dimethyl-3,3a,4,5,5a,6,7,8-octahydronaphtho[1,2-b]furan-2(9bH)-one;

1-(((5aR,9bS)-3a-Hydroxy-5a,9-dimethyl-2-oxo-2,3,3a, 4,5,5a,6,7,8,9b-decahydro naphtho[1,2-b]furan-3-yl) methyl)pyrrolidine-2-carboxylic acid;

13-(Piperidin-1-yl)-4,5-epoxy-7-hydroxyeudesm-6,12-olide;

1-(((5aR,9bS)-3a-Hydroxy-5a,9-dimethyl-2-oxo-2,3,3a,4,5,5a,6,7,8,9b-decahydro naphtho[1,2-b]furan-3-yl)methyl)piperidin-4-one;

(5aR,9bS)-3a-Hydroxy-3-((4-hydroxypiperidin-1-yl)methyl)-5a,9-dimethyl-3,3a,4,5,5a,6,7,8-octahydronaphtho[1,2-b]furan-2(9bH)-one;

(5aR,9bS)-3-(1,4'-Bipiperidin-1'-ylmethyl)-3a-hydroxy-5a,9-dimethyl-3,3a,4,5,5a,6,7,8-octahydronaphtho[1,2-b]furan-2(9bH)-one;

(5aR,9bS)-3a-hydroxy-5a,9-dimethyl-3-morpholinomethyl)decahydronaphtho[1,2-b]furan-2(9bH)-one;

(5aR,9bS)-3a-Hydroxy-5a,9-dimethyl-3-(thiomorpholinomethyl)-3,3a,4,5,5a,6,7,8-octahydronaphtho[1,2-b]furan-2(9bH)-one;

(5aR,9bS)-3a-Hydroxy-5a,9-dimethyl-3-(thiomorpholino-1-oxide-methyl)-3,3a,4,5,5a,6,7,8-octahydronaphtho[1,2-b]furan-2(9bH)-one;

(5aR,9bS)-3-((4-Benzylpiperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3a-hydroxy-5a,9-dimethyl-3-(piperazin-1-ylmethyl)-3,3a,4,5,5a,6,7,8-octahydronaphtho[1,2-b]furan-2(9bH)-one;

(5aR,9bS)-3a-hydroxy-5a,9-dimethyl-3-(piperazin-1-ylmethyl)decahydronaphtho[1,2-b]furan-2(9bH)-one;

(5aR,9bS)-3-((4-(2,6-dimethylbenzyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3-((4-(3,5-dimethoxy-2-methylbenzyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3a-hydroxy-3-((4-(2-(hydroxymethyl)-3,5-dimethoxy-6-methylbenzyl)piperazin-1-yl)methyl)-5a,9-dimethyl-3,3a,4,5,5a,6,7,8-octahydronaphtho[1,2-b]furan-2(9bH)-one;

(5aR,9bS)-3-((4-(2-fluorobenzyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3a-hydroxy-5a,9-dimethyl-3-((4-(perfluorobenzyl)piperazin-1-yl)methyl)-3,3a,4,5,5a,6,7,8-octahydronaphtho[1,2-b]furan-2(9bH)-one;

(5aR,9bS)-3-((4-(2-chloro-6-fluorobenzyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3-((4-(2-fluoro-6-(trifluoromethyl)benzyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3-((4-(benzo[d][1,3]dioxol-4-ylmethyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3a-hydroxy-3,4(4-(2-(hydroxymethyl)-3,5-dimethoxybenzyl)piperazin-1-yl)methyl)-5a,9-dimethyl-3,3a,4,5,5a,6,7,8-octahydronaphtho[1,2-b]furan-2(9bH)-one 2-(4-(((5aR,9bS)-3a-hydroxy-5a,9-dimethyl-2-oxo-2,3,3a,4,5,5a,6,7,8,9b-decahydro naphtho[1,2-b]furan-3-yl)methyl)piperazin-1-yl)methyl)-4,6-dimethoxybenzyl acetate;

2-(4-(((5aR,9bS)-3a-hydroxy-5a,9-dimethyl-2-oxo-2,3,3a,4,5,5a,6,7,8,9b-decahydro naphtho[1,2-b]furan-3-yl)methyl)piperazin-1-yl)methyl)-4,6-dimethoxybenzaldehyde oxime;

2((4-(((5aR,9bS)-3a-hydroxy-5a,9-dimethyl-2-oxo-2,3,3a,4,5,5a,6,7,8,9b-decahydro naphtho[1,2-b]furan-3-yl)methyl)piperazin-1-yl)methyl)-4,6-dimethoxybenzaldehyde;

2-((4-(((5aR,9bS)-3a-hydroxy-5a,9-dimethyl-2-oxo-2,3,3a,4,5,5a,6,7,8,9b-decahydro naphtho[1,2-b]furan-3-yl)methyl)piperazin-1-yl)methyl)-4,6-dimethoxybenzoic acid;

(5aR,9bS)-3-((4-benzylpiperazin-1-yl)methyl)-5a,9-dimethyl-2,3,3a,4,5,5a,6,7,8,9b-decahydronaphtho[1,2-b]furan-2,3a-diol;

(5aR,9bS)-3-((4-benzylpiperazin-1-yl)methyl)-3a-hydroxy-5a,9-dimethyl-2,3,3a,4,5,5a,6,7,8,9b-decahydronaphtho[1,2-b]furan-2-yl acetate;

(5aR,9bS)-3a-hydroxy-5a,9-dimethyl-3-((4-phenethylpiperazin-1-yl)methyl)-3,3a,4,5,5a,6,7,8-octahydronaphtho[1,2-b]furan-2(9bH)-one;

(5aR,9bS)-3-((4-benzylpiperazin-1-yl)methyl)-5a,9-dimethyl-2,3,3a,4,5,5a,6,7,8,9b-decahydronaphtho[1,2-b]furan-3a-ol;

(5aR,9bS)-3-((4-Acetylpiperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3a-Hydroxy-5a,9-dimethyl-3-((4-phenylpiperazin-1-yl)methyl)-3,3a,4,5,5a,6,7,8-octahydronaphtho[1,2-b]furan-2(9bH)-one;

(5aR,9bS)-3a-Hydroxy-3-((4-(2-methoxyphenyl)piperazin-1-yl)methyl)-5a,9-dimethyl-3,3a,4,5,5a,6,7,8-octahydronaphtho[1,2-b]furan-2(9bH)-one;

(5aR,9bS)-3-((4-(2-Chlorophenyl)piperazin-1-yl)methyl)-3a-hydroxy-5a,9-dimethyl-3,3a,4,5,5a,6,7,8-octahydronaphtho[1,2-b]furan-2(9bH)-one;

(5aR,9bS)-3a-Hydroxy-5a,9-dimethyl-3((4(4-(pyridin-2-yl)piperazin-1-yl)methyl)-3,3a,4,5,5a,6,7,8-octahydronaphtho[1,2-b]furan-2(9bH)-one;

(5aR,9bS)-3a-Hydroxy-3((4(4-(((5aR,9bS)-3a-hydroxy-5a,9-dimethyl-2-oxo-2,3,3a,4,5,5a,6,7,8,9b-decahydronaphtho[1,2-b]furan-3-yl)methyl)piperazin-1-yl)methyl)-5a,9-dimethyl-3,3a,4,5,5a,6,7,8-octahydronaphtho[1,2-b]furan-2(9bH)-one;

3-Ethyl-1-(((5aR,9bS)-3a-hydroxy-5a,9-dimethyl-2-oxo-2,3,3a,4,5,5a,6,7,8,9b-decahydro naphtho[1,2-b]furan-3-yl)methyl)-1-(((5aS,9bR)-3a-hydroxy-5a,9-dimethyl-2-oxo-2,3,3a,4,5,5a,6,7,8,9b-decahydronaphtho[1,2-b]furan-3-yl)methyl)thiourea;

Methyl 2-(((5aR,9bS)-3a-hydroxy-5a,9-dimethyl-2-oxo-2,3,3a,4,5,5a,6,7,8,9b-decahydro naphtho[1,2-b]furan-3-yl)methylamino)acetate;

(5aR,9bS)-3a-Hydroxy-5a,9-dimethyl-3-(((2R)-2,4,5-trihydroxy-6-(hydroxymethyl)tetrahydro-2H-pyran-3-ylamino)methyl)-3,3a,4,5,5a,6,7,8-octahydro naphtho[1,2-b]furan-2(9bH)-one;

(5aR,9bS)-3a-Hydroxy-3-(((2-hydroxy-2-(4-hydroxyphenyl)ethyl)(methyl)amino)methyl)-5a,9-dimethyl-3,3a,4,5,5a,6,7,8-octahydronaphtho[1,2-b]furan 2 (9bH)-one;

(5aR,9bS)-3a-Hydroxy-3-(((2-hydroxy-2-(3-hydroxyphenyl)ethyl)(methyl)amino)methyl)-5a,9-dimethyl-3,3a,4,5,5a,6,7,8-octahydronaphtho[1,2-b]furan-2(9bH)-one; or 4-(1-Acetoxy-2-((((5aR,9bS)-3a-hydroxy-5a,9-dimethyl-2-oxo-2,3,3a,4,5,5a,6,7,8,9b-decahydronaphtho[1,2-b]furan-3-yl)methyl)(methyl)amino)ethyl)phenyl acetate, or a pharmaceutically acceptable salt thereof.

24. A process for the preparation of a compound of formula (A 3):

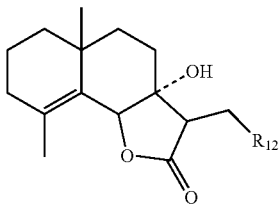

(A 3)

wherein
$R_{12}$ is —$NR_{15}R_{16}$;
$R_{15}$ and $R_{16}$ together with the N atom to which they are bonded, form a 5-, 6- or 7-membered heterocyclyl, optionally having one or more additional heteroatoms selected from: O, N and S;
which comprises reacting a compound of formula (A):

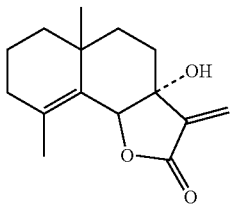

(A)

with an amine (H—$NR_{15}R_{16}$) wherein $R_{15}$ and $R_{16}$ are as defined above; in presence of a base selected from triethylamine, sodium carbonate and potassium carbonate in an alcoholic solvent selected from methanol, ethanol and propanol; at a temperature in the range of 20° C. to 30° C. under stirring over a time period ranging from 2 hours to 20 hours to obtain a compound of general formula (A3); and optionally, converting the resulting compound into a pharmaceutically acceptable salt.

25. A process for the preparation of a compound of formula (B2):

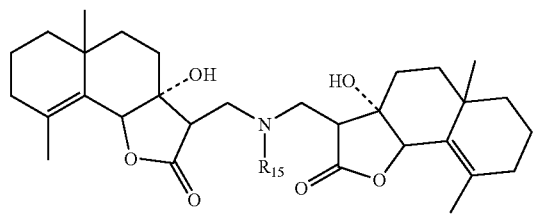

(B 2)

wherein
$R_{15}$ is selected from hydrogen, alkyl or —C(S)—$NHR_{14}$; wherein $R_{14}$ is substituted alkyl which comprises:
a) reacting a compound of formula (A):

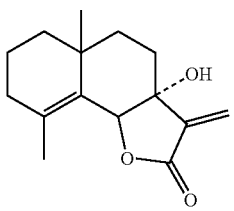

(A)

with ammonia, in presence of an alcoholic solvents selected from methanol, ethanol and propanol; at a temperature in the ranging from 20° C. to 30° C. under stirring over a time period ranging from 3 hours to 10 hours to obtain the compound of formula (B1);

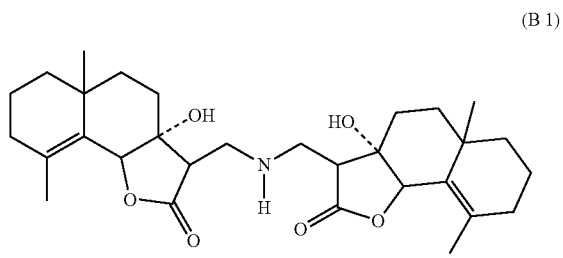 [SMILES: CC1=C2C3OC(=O)C(CNCC4C(=O)OC5C6=C(C)CCCC6(C)CC[C@]45O)[C@]3(O)CCC2(C)CCC1]

(B 1)

b) reacting the compound of formula (B1) wherein $R_{15}$ is H, with $R_{15}$-halide reagent, wherein $R_{15}$ is selected from alkyl, —C(O)$R_{14}$, and —C(S)—$NHR_{14}$; wherein $R_{14}$ is substituted alkyl, in presence of a base selected from pyridine, triethylamine, sodium carbonate and potassium carbonate, and a solvent selected from acetonitrile, tetrahydrofuran or dioxane; at a temperature ranging from 20° C. to 30° C. under stirring over a time period ranging from 2 hours to 20 hours, to obtain a compound of general formula (B2), wherein $R_{15}$ is selected from alkyl, —C(O)$R_{14}$, and —C(S)—$NHR_{14}$; wherein $R_{14}$ is substituted alkyl;

c) optionally, converting the resulting compound obtained in step (b) into a pharmaceutically acceptable salt.

26. A pharmaceutical composition, comprising a therapeutically effective amount of a compound of formula 1 as defined in claim 1, or a pharmaceutically acceptable salt thereof, and a pharmaceutically acceptable carrier or diluent.

27. A pharmaceutical composition, comprising a therapeutically effective amount of a compound as defined in claim 23, or a pharmaceutically acceptable salt thereof, and a pharmaceutically acceptable carrier or diluent.

28. A compound according to claim 1, wherein the compound is (5aR,9bS)-3a-hydroxy-5a,9-dimethyl-3-((4-methylpiperazin-1-yl)methyl)-3,3a,4,5,5a,6,7,8-octahydronaphtho[1,2-b]furan-2(9bH)-one hydrochloride;

Ethyl 4-(((5aR,9bS)-3a-hydroxy-5a,9-dimethyl-2-oxo-2,3,3a,4,5,5a,6,7,8,9b-decahydro naphtha[1,2-b]furan-3-yl)methyl)piperazine-1-carboxylate hydrochloride;

(5aR,9bS)-3a-Hydroxy-5a,9-dimethyl-3-((4-o-tolylpiperazin-1-yl)methyl)-3,3a,4,5,5a,6,7,8-octahydronaphtho[1,2-b]furan-2(9bH)-one hydrochloride; or (5aR,9bR)-3a-Hydroxy-3-((((5aR,9bS)-3a-hydroxy-5a,9-dimethyl-2-oxo-2,3,3a,4,5,5a,6,7,8,9b-decahydronaphtho[1,2-b]furan-3-yl)methylamino)methyl)-5a,9-dimethyl-3,3a,4,5,5a,6,7,8-octahydronaphtho[1,2-b]furan-2(9bH)-one hydrochloride.

29. A pharmaceutical composition comprising a therapeutically effective amount of a compound of claim 28, and a pharmaceutically acceptable carrier or diluent.

* * * * *